US009321797B2

(12) United States Patent
Sauve et al.

(10) Patent No.: US 9,321,797 B2
(45) Date of Patent: Apr. 26, 2016

(54) NICOTINOYL RIBOSIDE COMPOSITIONS AND METHODS OF USE

(71) Applicant: Cornell University, Ithaca, NY (US)

(72) Inventors: Anthony A. Sauve, New Rochelle, NY (US); Tianle Yang Redanz, Astoria, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 14/543,439

(22) Filed: Nov. 17, 2014

(65) Prior Publication Data

US 2015/0072950 A1    Mar. 12, 2015

Related U.S. Application Data

(60) Continuation of application No. 13/351,411, filed on Jan. 17, 2012, now Pat. No. 9,000,147, which is a division of application No. 11/601,714, filed on Nov. 17, 2006, now Pat. No. 8,106,184.

(60) Provisional application No. 60/738,081, filed on Nov. 18, 2005.

(51) Int. Cl.
    *A61K 31/351*    (2006.01)
    *A61K 31/706*    (2006.01)
    *A61K 45/06*     (2006.01)
    *C07H 19/048*    (2006.01)

(52) U.S. Cl.
    CPC ............ *C07H 19/048* (2013.01); *A61K 31/351* (2013.01); *A61K 31/706* (2013.01); *A61K 45/06* (2013.01)

(58) Field of Classification Search
    None
    See application file for complete search history.

(56) References Cited

U.S. PATENT DOCUMENTS

| | | | |
|---|---|---|---|
| 3,783,137 | A | 1/1974 | Gerber |
| 4,735,966 | A | 4/1988 | Wu et al. |
| 8,106,184 | B2 | 1/2012 | Suave et al. |
| 2003/0049323 | A1 | 3/2003 | Hitt et al. |
| 2003/0229033 | A1 | 12/2003 | Sauve et al. |
| 2006/0229265 | A1 | 10/2006 | Milburn et al. |
| 2007/0117765 | A1 | 5/2007 | Sauve et al. |
| 2012/0172584 | A1 | 7/2012 | Sauve et al. |

FOREIGN PATENT DOCUMENTS

WO    WO 01/94370 A1    12/2001

OTHER PUBLICATIONS

Araki et al., *Science*, 305: 1010-1013 (Aug. 13, 2004).
Atkinson et al., *J. Chem. Soc.*, 610-615 (1965).
Davies et al., *Nucleosides and Nucleotides*, 14(3-5): 311-312 (1995).
Esmans et al., *Biomed. Mass Spectrom.*, 7 (9): 377-380 (1980).
Franchetti et al., *Bioorg. Med. Chem. Lett.*, 14: 4655-4658 (2004).
Franchetti et al., *Bioorg. Med. Chem.*, 13: 2045-2053 (2005).
Freyne et al., *Carbohydr. Res.*, 78: 235-242 (1980).
Freyne et al., *J. Carbohydr. Nucleos. Nucleot.*, 3 (3): 113-128 (1976).
Friedlos et al., *Biochem. Pharmacol.* 44(1) : 25-31 (1992).
Greene, Protective Groups in Organic Synthesis, Third Edition (John Wiley & Sons, Inc., 1999), Protection for the Carboxyl Group, pp. 369-394.
Greene, Protective Groups in Organic Synthesis, Third Edition (John Wiley & Sons, Inc., 1999), Protection for the Hydroxyl Group, pp. 150-160.
Han et al., *Journal American Chemical Society*, 127(28): 10039-10044 (2005).
Huntley, *Nucleosides, Nucleotides & Nucleic Acids*, 20(4-7): 731-733 (2001).
Jarman et al., *J. Chem. Soc. (C)*, pp. 199-203 (1960).
Mel'nikova et al., *Zhurnal Obshchei Khimii*, 37(7) : 1507-1511 (1967).
Plasman et al., *J. Nat. Prod.*1, 63 : 1261-1264 (2000).
Tanimori et al., *Bioorg. Med. Chem. Lett.*, 12: 1135-1137 (2002).
Testa et al., *Hydrolysis in Drug and Prodrug Metabolism*, Chapter 4 (pp. 81-162) and Chapter 8 (pp. 419-534), John Wiley & Sons (Sep. 2003).
Riemschneider et al., *Bochu Kagaku Kekyusho*, 41(3): 99-106 (1976).
Wang et al., *J. Cell Biol.*, 170 (3): 349-355 (Aug. 1, 2005).
Yalowitz et al., *Curr. Med. Chem.*, 9: 749-758 (2002).
Yang, *J. Med. Chem.* 50: 6458-6646 (2007).
U.S. Patent and Trademark Office, International Search Report in International Patent Application No. PCT/US2006/044580 (May 24, 2007).
U.S. Patent and Trademark Office, Written Opinion in International Patent Application No. PCT/US2006/044580 (May 24, 2007).

*Primary Examiner* — Layla Bland
(74) *Attorney, Agent, or Firm* — Leydig, Voit & Mayer, Ltd.

(57) ABSTRACT

The invention relates to compositions of nicotinoyl ribosides and nicotinamide riboside derivatives and their methods of use. In some embodiments, the invention relates to methods of making nicotinoyl ribosides. In some embodiments, the invention relates to pharmaceutical compositions and nutritional supplements containing a nicotinoyl riboside. In further embodiments, the invention relates to methods of using nicotinoyl ribosides and nicotinamide riboside derivatives that promote the increase of intracellular levels of nicotinamide adenine dinucleotide (NAD+) in cells and tissues for improving cell and tissue survival.

21 Claims, 20 Drawing Sheets

-20°C: kinetically controlled reaction
4°C: thermodynamically controlled reaction ANR : N-allyl-nicotinamide riboside DMNR:
Dimethyl
nicotinamide
riboside

NICOTINOYL RIBOSIDE COMPOSITIONS AND METHODS OF USE

CROSS-REFERENCE TO RELATED APPLICATIONS

This patent application is a continuation of copending U.S. patent application Ser. No. 13/351,411, filed Jan. 17, 2012, which is a divisional of U.S. patent application Ser. No. 11/601,714, filed Nov. 17, 2006, now issued as U.S. Pat. No. 8,106,184, which claims the benefit of U.S. Provisional Application No. 60/738,081, filed Nov. 18, 2005, the disclosures of which are hereby incorporated by reference in their entireties and for all purposes.

FIELD OF INVENTION

The invention relates to compositions of nicotinoyl ribosides and nicotinamide riboside derivatives and their methods of use. In some embodiments, the invention relates to methods of making nicotinoyl ribosides. In some embodiments, the invention relates to pharmaceutical compositions and nutritional supplements containing a nicotinoyl riboside. In further embodiments, the invention relates to methods of using nicotinoyl ribosides and nicotinamide riboside derivatives that promote the increase of intracellular levels of nicotinamide adenine dinucleotide (NAD+) in cells and tissues for improving cell and tissue survival.

BACKGROUND

Nicotinamide adenine dinucleotide (NAD+) is a natural coenzyme that functions as an intermediary in cellular oxidation and reduction reactions as well as an ADP-ribosyltransferase substrate. Altering intracellular NAD+ levels can improve the health of a cell, but introduction of compounds that enter NAD+ metabolic pathways can also prove toxic to cells. For example, benzamide riboside (BAR) is a well-known antitumor agent. BR is a prodrug that can be phosphorylated to its 5'-monophosphate and then converted to its active metabolite benzamide adenine dinucleotide (BAD). That metabolite is an active analogue of NAD+ and an inhibitor of inosine 5'-monophosphate dehydrogenase (IMPHD). IMPDH is linked to malignant transformations. BAR shows selective sensitivity to central nervous system and leukemic cell lines. However, BAD also inhibits other dehydrogenases, such as malate dehydrogenase and glutamic acid dehydrogenase which may cause adverse effects if used as a therapeutic. Thus, there is a need to identify compositions that are capable of improving the health of damaged or diseased cells preferably by altering intracellular NAD+ levels and that do not have adverse effects if the compositions are given therapeutically.

SUMMARY OF INVENTION

The invention relates to compositions of nicotinoyl ribosides and nicotinamide riboside derivatives and their methods of use. In some embodiments, the invention relates to methods of making nicotinoyl ribosides including nicotinamide riboside. In some embodiments, the invention relates to pharmaceutical compositions and nutritional supplements containing a nicotinoyl riboside. In further embodiments, the invention relates to methods of using nicotinoyl ribosides and nicotinamide riboside derivatives that promote the increase of intracellular levels nicotinamide adenine dinucleotide (NAD+) in cells and tissues for improving cell and tissue survival.

In some embodiments, the invention relates to a compound having the formula:

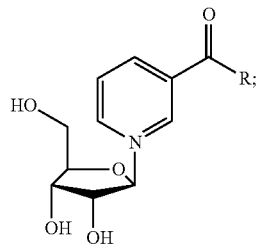

and salt complexes thereof wherein R is selected from the group consisting of alkylamino, substituted alkylamino, dialkylamino, substituted dialkylamino, alkyloxy, substituted alkyloxy, aryloxy, substituted aryloxy, hydroxylamino, substituted hydroxylamino, O-alkyloxyamino, substituted O-alkyloxyamino, aminooxy, substituted aminoxy, N-alkylaminooxy, substituted N-alkylaminoxy, hydrazino, substituted hydrazino, alkylhydrazino, and substituted alkylhydrazino.

In additional embodiments, the invention relates to a compound having the following formula:

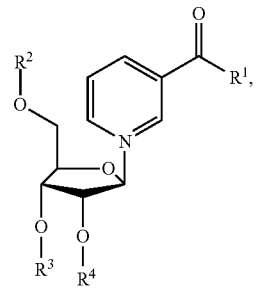

and salt complexes thereof wherein, $R^1$ is alkyloxy, substituted alkyloxy, aryloxy, substituted aryloxy, arylthio, substituted arylthio, alkylthio, substituted alkylthio, aminooxy, substituted aminoxy, N-alkylaminooxy, and substituted N-alkylaminooxy; and $R^2$, $R^3$, and $R^4$ are the same or different and, at each occurrence, independently acyl or substituted acyl.

In further embodiments, the invention relates to a compound having the following formula:

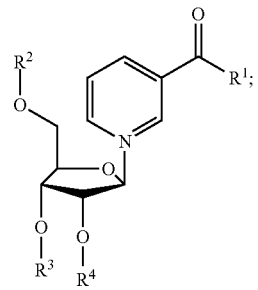

and salt complexes thereof wherein, $R^1$ is alkylamino, substituted alkylamino, dialkylamino, substituted dialkylamino, hydrazine, substituted hydrazino, N-alkylaminohydrazino, hydroxylamino, substituted hydroxylamino, O-alkyloxyamino, or substituted O-alkyloxyamino; $R^2$, $R^3$, and $R^4$ are the same or different and, at each occurrence, independently acyl or substituted acyl.

In additional embodiments, the invention relates to a method of making a compound having Formula I:

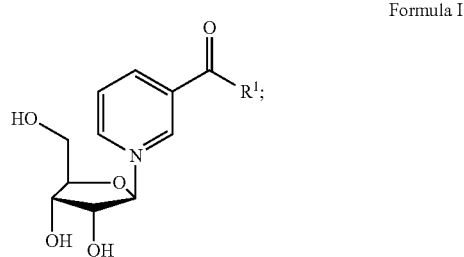

Formula I wherein, $R^1$ is amino, alkylamine, substituted alkylamino, dialkylamino, substituted dialkylamino, alkyloxy, substituted alkyloxy, aryloxy, substituted aryloxy, hydroxylamino, substituted hydroxylamino, O-alkyloxyamino, substituted O-alkyloxyamino, aminooxy, substituted aminoxy, N-alkylaminooxy, substituted N-alkylaminoxy, hydrazino, substituted hydrazino, alkylhydrazino, and substituted alkylhydrazino comprising: i) mixing a) tetra-acyl or substituted acyl ribofuranose and b) a compound having formula II:

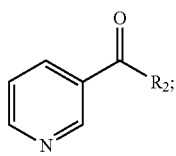

Formula II wherein, $R^2$ is alkyloxy, substituted alkyloxy, aryloxy, substituted aryloxy, alkylthiol, substituted alkylthiol, arylthiol, substituted arylthiol, aminooxy, substituted aminooxy, N-alkylaminooxy or substituted N-alkylaminooxy; under conditions such that a compound of formula III:

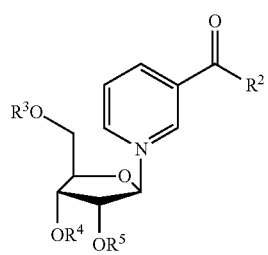

Formula III wherein, $R^2$ is alkyloxy, substituted alkyloxy, aryloxy, substituted aryloxy, alkylthiol, substituted alkylthiol, arylthiol, substituted arylthiol, aminooxy, substituted aminooxy, N-alkylaminooxy or substituted N-alkyl aminooxy, and $R^3$, $R^4$ and $R^5$ are the same or different and, at each occurrence, independently acyl or substituted acyl is formed; and ii) mixing the compound of formula III with ammonia, hydrazine, substituted hydrazine, alkylhydrazine, substituted alkylhydrazine, hydroxylamine, substituted hydroxylamine, O-alkyloxyamine, substituted O-alkyloxyamine, N-alkylaminohydroxide, substituted N-alkylaminohydroxide, alkylamine, substituted alkylamine, dialkylamine, substituted dialkylamine, alkoxide, or substituted alkoxide under conditions such that a compound of formula I is formed. In further embodiments, the conditions of making compound I from compound III are in a halogenated alkyl alcohol solvent at a temperature below room temperature. In further embodiments, said solvent is trifluoromethanol.

In some embodiments, the invention relates to a compound having the following formula:

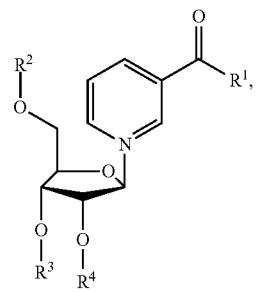

and salt complexes thereof wherein, $R^1$ is alkyloxy, substituted alkyloxy, aryloxy, substituted aryloxy, arylthio, substituted arylthio, alkylthio, or substituted alkylthio; and $R^2$, $R^3$, and $R^4$ are the same or different and, at each occurrence, independently acyl or substituted acyl.

In some embodiments, the invention relates to a method of making a compound having Formula I:

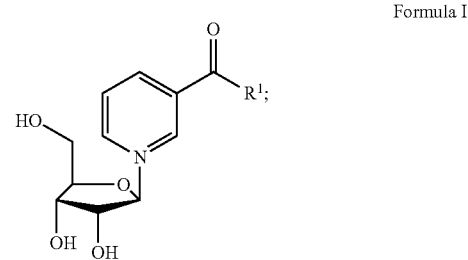

Formula I wherein, $R^1$ is amine, substituted amine, alkylamine, substituted alkylamine, dialkylamine, substituted dialkylamine, alkyloxy, or substituted alkyloxy, comprising: i) mixing a) tetra-acyl or substituted acyl ribofuranose, preferably tetra-acetyl ribofuranose, and b) a compound having formula II:

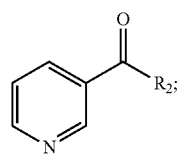

Formula II wherein, $R^2$ is alkyloxy, substituted alkyloxy, aryloxy, substituted aryloxy, alkylthiol, substituted alkylthiol, arylthiol or substituted arylthiol under conditions such that a compound of formula III:

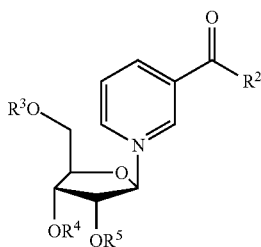

Formula III wherein, $R^2$ is alkyloxy, substituted alkyloxy, aryloxy, substituted aryloxy, alkylthiol, substituted alkylthiol, arylthiol or substituted arylthiol, and $R^3$, $R^4$ and $R^5$ are the same or different and, at each occurrence, independently acyl or substituted acyl is formed; and ii) mixing the compound of formula III with ammonia, substituted ammonia alkylamine, substituted alkylamine, dialkylamine, substituted dialkylamine, alkoxide, or substituted alkoxide under conditions such that a compound of formula I is formed.

In some embodiments, the invention relates to a compound having the formula:

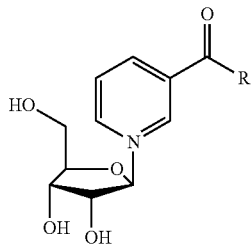

and salt complexes thereof wherein R is selected from the group consisting of alkylamine, substituted alkylamine, dialkylamine, substituted dialkylamine, alkyloxy, and substituted alkyloxy.

In additional embodiments, the invention relates to a compound having the following formula:

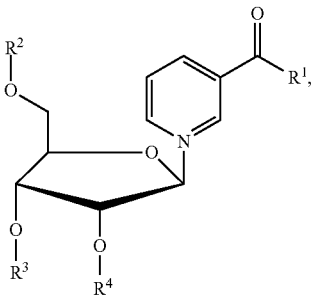

and salt complexes thereof wherein, $R^1$ is alkyloxy or substituted alkyloxy, or aryloxy or alkylthio or arylthio; and $R^2$, $R^3$, and $R^4$ are the same or different and, at each occurrence, independently acyl or substituted acyl.

In some embodiments, the invention relates to a compound having the following formula:

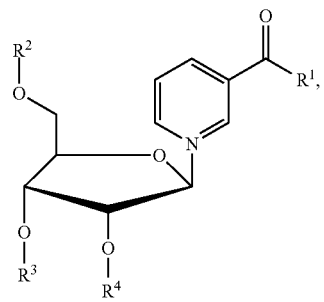

and salt complexes thereof wherein, $R^1$ is aminoalkyl, substituted amino alkyl, diaminoalkyl, or substituted diaminoalkyl and $R^2$, $R^3$, and $R^4$ are the same or different and, at each occurrence, independently acyl or substituted acyl.

In some embodiments, the invention relates to a method of making a compound having Formula I:

Formula I

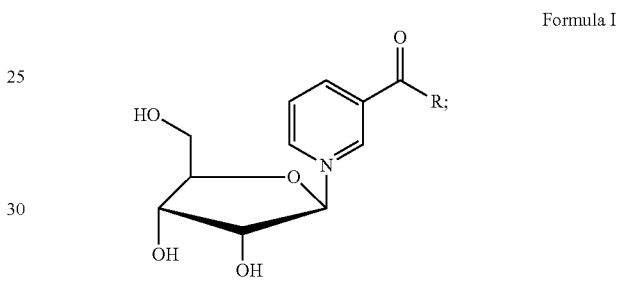

wherein, R is $NH_2$, alkylamino, substituted alkylamino, dialkylamino, substituted dialkylamino, alkyloxy, and substituted alkyloxy, comprising: i) mixing tetra-acyl ribofuranose, preferably tetra-acetyl ribofuranose, and alkyl or aryl pyridine-3-carboxylate ester or thioester compound under conditions such that a compound of formula II:

Formula II is formed where $R^2$ is —O-alkyl, —O-aryl, —S-alkyl or —S-aryl and, $R^3$, $R^4$ and $R^5$ are the same or different and, at each occurrence, independently acyl and iii) mixing the compound of formula II with an alkylamine, substituted alkylamine, dialkylamine, substituted dialkylamine, alkoxide, and substituted alkoxide under conditions such that a compound of formula I is formed.

In some embodiments, the invention relates to making alkyl 1-[3,4-diacetyloxy-5-(acetyloxymethyl)oxolan-2-yl]-pyridine-3-carboxylate, preferably alkyl 1-[3,4-diacetyloxy-5-(acetyloxymethyl)oxolan-2-yl]-pyridine-3-carboxylate, comprising mixing a composition consisting essentially of 1,2,3,5-tetra-O-acetyl-beta-D-ribofuranose, alkyl pyridine- 3-carboxylate, and trimethylsilyl trifluoromethanesulfonate under conditions such that alkyl 1-[3,4-diacetyloxy-5-(acetyloxymethyl)oxolan-2-yl]-pyridine-3-carboxylate is formed.

In some embodiments, the invention relates to a method of making N-alkyl or N,N dialkyl 1-[3,4-dihydroxy-5-(hydroxymethyl)oxolan-2-yl]pyridine-5-carboxamide comprising mixing alkyl 1-[3,4-diacetyloxy-5-(acetyloxymethyl)oxolan-2-yl]-pyridine-3-carboxylate with an primary or secondary amine under conditions such that N-alkyl or N,N dialkyl 1-[3,4-dihydroxy-5-(hydroxymethyl)oxolan-2-yl] pyridine-5-carboxamide is formed.

In some embodiments, the invention relates to a method of making O-Alkyl$^2$ 1-[3,4-dihydroxy-5-(hydroxymethyl)oxolan-2-yl]pyridine-5-carboxylate comprising mixing O-Alkyl$^1$ 1-[3,4-dihydroxy-5-(hydroxymethyl)oxolan-2-yl] pyridine-5-carboxylate and sodium alkyl$^2$ oxide under conditions such that O-Alkyl$^2$ 1-[3,4-dihydroxy-5-(hydroxymethyl)oxolan-2-yl]pyridine-5-carboxylate is formed.

In some embodiments, the invention relates to a substituted or unsubstituted compound capable of inhibiting inosine 5'-monophosphate dehydrogenase having the formula:

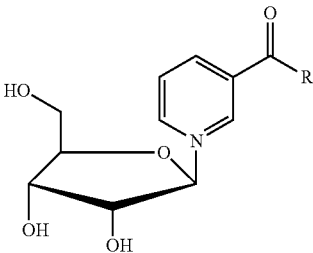

wherein, R is alkylamino, substituted alkylamino, dialkylamino, substituted dialkylamino, alkyloxy, and substituted alkyloxy. In further embodiments, R is —OMe, —OEt, —OCH$_2$CH$_2$OH, —NHMe, —NHEt, —NHCH$_2$CH$_2$OH, —NHCH$_2$CH═CH$_2$, —NHCH(CH$_3$)$_2$, —NHCH$_2$CH$_2$NH$_2$, —NHcyclopropyl, —N(CH$_3$)$_2$, or N substituted pyrrolidinyl. In further embodiments, the compound is obtained in a purified form.

In some embodiments, the invention relates to a compound having the following formula:

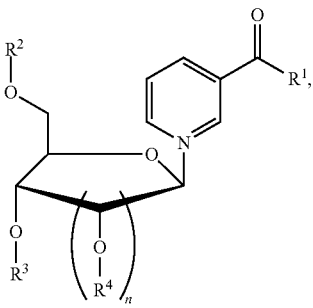

wherein, R$^1$ is alkylamino, substituted alkylamino, dialkylamino, or substituted dialkylamino; n is 1 or 2; and R$^2$, R$^3$, and R$^4$ are the same or different and, at each occurrence, independently acyl or substituted acyl. In additional embodiments, R$^1$ is not —NHMe, —NHEt, or —NEt$_2$.

In some embodiments, the invention relates to a purified compound having the following formula:

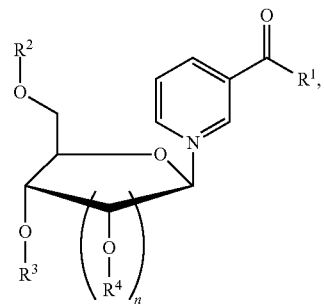

wherein, R$^1$ is alkyloxy or substituted alkyloxy, preferably methoxy and ethoxy and R$^2$, n is one or two; and R$^3$, and R$^4$ are the same or different and, at each occurrence, independently acyl or substituted acyl, preferably acetyl and benzoyl. In additional embodiments, R$^1$ is not —OMe or —OEt.

In some embodiments, the invention relates to a method of making an nicotinamide derivative comprising: i) mixing tetra-acyl ribofuranose, preferably tetra-acetyl ribofuranose and alkyl or aryl pyridine-3-carboxylate ester or thioester compound under conditions such that a second compound having the following formula:

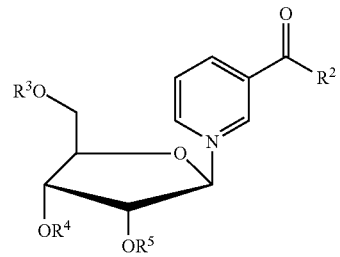

is formed wherein R$^2$ is —O-alkyl, —O-aryl, —S-alkyl or —S-aryl and, R$^3$, R$^4$ and R$^5$ are the same or different and, at each occurrence, independently acyl and iii) mixing said second compound with H—R, wherein R is —OMe, —OEt, —OCH$_2$CH$_2$OH, —NHMe, —NHEt, —NHCH$_2$CH$_2$OH, —NHCH$_2$CH═CH$_2$, —NHCH(CH$_3$)$_2$, —NHCH$_2$CH$_2$NH$_2$, —NHcyclopropyl, —N(CH$_3$)$_2$, or N substituted pyrrolidinyl; under conditions such that a compound having the following formula:

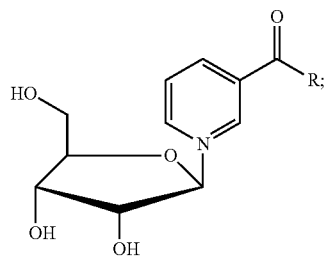

is formed.

In some embodiments, the invention relates to compounds disclosed herein and salt complexes thereof. In further embodiment, said salt complexes are pharmaceutical preparations or nutritional supplement.

In other embodiments, the composition comprises a nicotinoyl riboside component comprising greater than 80%, or greater than 90%, 95% or 99% of a nicotinoyl riboside compound disclosed herein.

In some embodiments, the invention relates to a method of managing or improving the health of cells, preferably stem cells, more preferably embryonic stem cells comprising: i) providing a) a composition comprising nicotinoyl riboside substituted through the carbonyl to form a substituted or unsubstituted ester or alkyl or dialkyl amide disclosed herein and b) a cell; and ii) mixing said composition and said cell under conditions such that the heath of said cell is managed or improved.

In some embodiments, the invention relates to a growth medium containing a nicotinoyl riboside or a nicotinamide derivative disclosed herein. In further embodiments, the invention relates to methods of using nicotinoyl ribosides and nicotinamide riboside derivatives for increasing NAD+ levels in cells and tissues and for improving cell and tissue survival. In further embodiments said cells are embryonic stem cells and said tissue is a blastocyst comprising embryonic stem cells.

In some embodiment, the invention relates to a method of managing, preventing or treating cancer preferably leukemia comprising i) providing a) a subject having symptoms of cancer preferably leukemia and b) a nicotinoyl riboside derivative disclosed herein and ii) administering said derivative to said subject. In further embodiments, a nicotinoyl riboside or nicotinamide derivatives that inhibits inosine 5'-monophosphate dehydrogenase.

In some embodiments, the invention relates to a method of managing or improving the health of cells, preferably stem cells, more preferably embryonic stem cells comprising: i) providing a) a composition comprising compound having the following formula:

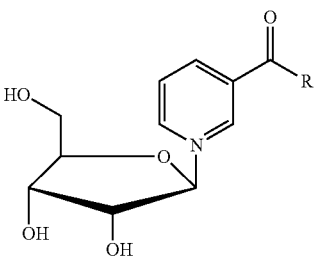

wherein R is —OMe, —OEt, —OCH$_2$CH$_2$OH, —NHMe, —NHEt, —NHCH$_2$CH$_2$OH, —NHCH$_2$CH=CH$_2$, —NHCH(CH$_3$)$_2$, —NHCH$_2$CH$_2$NH$_2$, —NHcyclopropyl, —N(CH$_3$)$_2$, or N substituted pyrrolidinyl and b) a cell; and ii) mixing said composition and said cell under conditions such that the heath of said cell is managed or improved.

In additional embodiments, the invention relates to a growth medium containing a compound having the following formula:

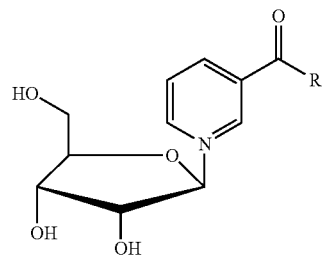

wherein R is —OMe, —OEt, —OCH$_2$CH$_2$OH, —NHMe, —NHEt, —NHCH$_2$CH$_2$OH, —NHCH$_2$CH=CH$_2$, —NHCH(CH$_3$)$_2$, —NHCH$_2$CH$_2$NH$_2$, —NHcyclopropyl, —N(CH$_3$)$_2$, or N substituted pyrrolidinyl.

In some embodiment, the invention relates to a method of managing, preventing or treating cancer preferably leukemia comprising i) providing a) a subject having symptoms of cancer preferably leukemia and b) containing a compound having the following formula:

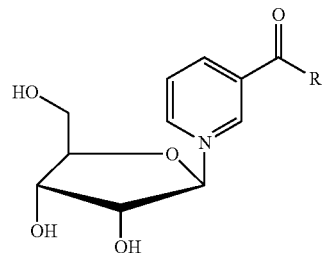

wherein R is —OMe, —OEt, —OCH$_2$CH$_2$OH, —NHMe, —NHEt, —NHCH$_2$CH$_2$OH, —NHCH$_2$CH=CH$_2$, —NHCH(CH$_3$)$_2$, —NHCH$_2$CH$_2$NH$_2$, —NHcyclopropyl, —N(CH$_3$)$_2$, or N substituted pyrrolidinyl and ii) administering said derivative to said subject. In further embodiments, nicotinoyl riboside and derivatives that inhibit inosine 5'-monophosphate dehydrogenase.

In some embodiments, the invention relates to a method of managing, preventing or treating neurodegenerative diseases comprising i) providing a) a subject having symptoms of a neurodegenerative disease and b) a composition comprising a nicotinyl riboside derivative disclosed herein and ii) administering said derivative to said subject. In further embodiments, said composition comprises a compound having the following formula:

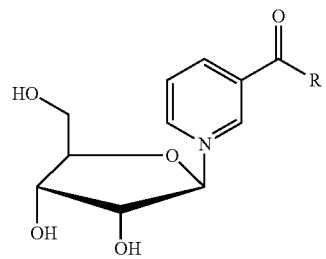

wherein R is —OMe, —OEt, —OCH$_2$CH$_2$OH, —NHMe, —NHEt, —NHCH$_2$CH$_2$OH, —NHCH$_2$CH=CH$_2$, —NHCH(CH$_3$)$_2$, —NHCH$_2$CH$_2$NH$_2$, —NHcyclopropyl, —N(CH$_3$)$_2$, or N substituted pyrrolidinyl.

In one aspect, the invention relates to the use of chemical intermediates disclosed herein to make nicotinic acid riboside, nicotinoyl riboside, or nicotinamide riboside, or derivatives.

In another aspect, the invention relates the use of nicotinoyl ribosides or derivatives for increasing the lifespan of a cell, and treating and/or preventing a wide variety of diseases and disorders including, for example, diseases or disorders related to aging or stress, diabetes, obesity, neurodegenerative diseases, cardiovascular disease, blood clotting disorders, inflammation, cancer, eye disorders, and/or flushing.

A method for treating or preventing one or more of cataracts, retinopathy, retinitis pigmentosa, ocular neuritis or a vascular disease of the capillary beds of the eye, comprising administering to a subject a therapeutically effective amount of nicotinoyl ribosides or derivative.

A method for reducing the weight of a subject, or preventing weight gain in a subject, comprising administering to a subject in need thereof a therapeutically effective amount of a nicotinoyl ribosides or derivative.

A method for prolonging the lifespan of a subject comprising administering to a subject a therapeutically effective amount of a nicotinoyl ribosides or derivative.

In further embodiments, the invention relates to a method of reducing drug toxicity comprising: i) providing: a) a subject, b) a drug, c) a composition comprising a nicotinyl riboside derivative; ii) administering said drug to said subject under conditions such that said drug produces an adverse reaction; and iii) administering said composition under conditions such that said adverse reaction is reduced. In further embodiment, said drug is a statin. In further embodiment, said subject is a human In further embodiments, said composition comprises a compound having the following formula:

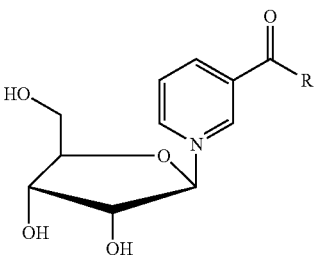

wherein R is —OMe, —OEt, —OCH$_2$CH$_2$OH, —NHMe, —NHEt, —NHCH$_2$CH$_2$OH, —NHCH$_2$CH=CH$_2$, —NHCH(CH$_3$)$_2$, —NHCH$_2$CH$_2$NH$_2$, —NHcyclopropyl, —N(CH$_3$)$_2$, or N substituted pyrrolidinyl.

In further embodiment, the invention relates to a method of preventing drug toxicity comprising: i) providing: a) a subject, b) a drug, c) a composition comprising a nicotinamide riboside derivative; ii) administering said drug in a concentration that typically produces toxicity in said subject and said nicotinamide riboside composition to said subject under conditions such that drug toxicity is prevented.

In some embodiments, the invention relates to a method in which the health of a cell is managed comprising: i) providing a) a composition comprising a compound having the following formula:

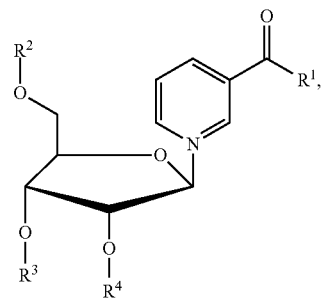

and salt complexes thereof wherein, R$^1$ is amine, alkylamine, substituted alkylamine, dialkylamino, substituted dialkylamino, alkyloxy, substituted alkyloxy, aryloxy, substituted aryloxy, arylthio, substituted arylthio, alkylthio, or substituted alkylthio; and R$^3$, R$^4$ and R$^5$ are the same or different and, at each occurrence hydrogen, independently acyl or substituted acyl; and b) cells in growth media; and ii) mixing said composition and said cells in growth media under conditions such that the heath of said cells is managed. In further embodiments, said cells are stem cells. In further embodiments, the composition increases the amount of NAD+ in the cells.

In some embodiments, the invention relates to a method of reducing an adverse drug reaction comprising: i) providing: a) a subject, b) a drug, and c) a composition comprising a nicotinoyl riboside or derivative; ii) administering said drug to said subject under conditions such that said drug produces an adverse reaction; and iii) administering said composition under conditions such that said adverse reaction is reduced. In further embodiments, said drug is a statin. In further embodiments, said subject is a human.

In some embodiments, the invention relates to a method of preventing an adverse drug reaction comprising: i) providing: a) a subject, b) a drug, and c) a composition comprising a nicotinoyl riboside or derivative; ii) administering said drug in a concentration that typically produces an adverse drug reaction in said subject and iii) administering said composition to said subject under conditions such that an adverse drug reaction is prevented. In further embodiments, said drug is a statin. In further embodiments, said subject is a human.

In some embodiments, the invention relates to using nicotinoyl ribosides or derivatives for increasing cellular sensitivity to stress (including increasing radiosensitivity and/or chemosensitivity), increasing the amount and/or rate of apoptosis, treatment of cancer (optionally in combination another chemotherapeutic agent), stimulation of appetite, and/or stimulation of weight gain.

In some embodiments, the invention relates to a method of treating cancer comprising i) providing a) a subject diagnosed with cancer and b) a nicotinoyl riboside or derivative; and ii) administering said derivative to said subject under conditions such that said cancer is reduced. In additional embodiments, the invention relates to a method of preventing cancer comprising i) providing a) a subject at risk for cancer and b) a nicotinoyl riboside or derivative; and ii) administering said derivative to said subject under conditions such that said cancer is prevented. In further embodiments, said nicotinoyl riboside or nicotinamide derivatives inhibits inosine 5′-monophosphate dehydrogenase. In further embodiments, said nicotinoyl riboside or nicotinamide derivatives reduce the amount of NAD+ in the cells comprising the cancer. In further embodiments, said subject is a human. In further embodiments, said cancer is selected from pancreatic cancer, endometrial cancer, small cell and non-small cell cancer of the lung (including squamous, adenocarcinoma and large cell types), squamous cell cancer of the head and neck, bladder, ovarian, cervical, breast, renal, CNS, and colon cancers, myeloid and lymphocytic leukemia, lymphoma, hepatic tumors, medullary thyroid carcinoma, multiple myeloma, melanoma, retinoblastoma, and sarcomas of the soft tissue and bone.

In additional embodiments, the invention relates to a method of treating or preventing neurodegenerative diseases neurodegenerative or condition comprising i) providing a) a subject diagnosed with, at risk for, or having symptoms of a neurodegenerative disease or neurodegenerative condition and b) a composition comprising a nicotinoyl riboside or derivative; and ii) administering said derivative to said subject under conditions such that said neurodegenerative disease or neurodegenerative condition is reduced. In further embodiments, said subject is a human. In further embodiments, said neurodegenerative disease or neurodegenerative condition is essential tremor, parkinson disease, alzheimer disease, huntington disease, ataxia, catatonia, epilepsy, neuroleptic malignant syndrome, dystonia, mental retardation, neuroacanthocytosis, Pelizaeus-Merzbacher, progressive supranuclear palsy, Striatonigral degeneration, Tardive dyskinesias, damage following stroke or trauma, or a lysosomal storage disorder, including lipid storage disorders (including Gaucher's and Niemann-Pick diseases), gangliosidosis (including Tay-Sachs disease), leukodystrophies, mucopolysaccharidoses, glycoprotein storage disorders, and mucolipidoses.

In some embodiments, the invention relates to a method of increasing intracellular concentrations of NAD+ comprising: a) providing i) a cell and ii) a nicotinoyl riboside or derivative; and b) mixing said cell and nicotinamide riboside or derivative under conditions such that intracellular concentrations of NAD+ increase. In additional embodiments, the invention relates to a method of decreasing intracellular concentrations of NAD+ comprising: a) providing i) a cell and ii) a nicotinoyl riboside or derivative; and b) mixing said cell and nicotinamide riboside or derivative under conditions such that intracellular concentrations of NAD+ decrease. In further embodiments said nicotinamide riboside is a compound having the following formula:

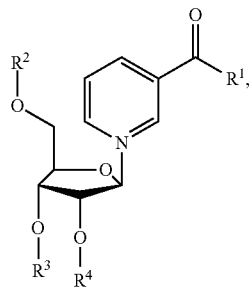

and salt complexes thereof wherein, $R^1$ is amine, alkylamine, substituted alkylamine, dialkylamino, substituted dialkylamino, alkyloxy, substituted alkyloxy, aryloxy, substituted aryloxy, arylthio, substituted arylthio, alkylthio, or substituted alkylthio; and $R^3$, $R^4$ and $R^5$ are the same or different and, at each occurrence hydrogen, independently acyl or substituted acyl.

In some embodiments, the invention relates to a method of preventing diabetes comprising i) providing a) a subject at risk for type I or type II diabetes and b) a composition comprising a nicotinoyl riboside or derivative; and ii) administering said composition to said subject under conditions such that said diabetes is prevented. In further embodiments, said subject is a human. In further embodiments, said subject is obese. In additional embodiments, the invention relates to a method of treating diabetes comprising i) providing a) a subject diagnosed with or with symptoms of type I or type II diabetes and b) a composition comprising a nicotinoyl riboside or derivative; and ii) administering said composition to said subject under conditions such that said symptoms are reduced. In further embodiments, said subject is a human. In further embodiments, said subject is obese.

In some embodiments, the invention relates to a method of preventing a subject from acquiring insulin insensitivity comprising i) providing a) a subject and b) a composition comprising a nicotinoyl riboside or derivative; and ii) administering said composition to said subject under conditions such that insulin insensitivity is prevented. In further embodiments, said subject is a human. In further embodiments, subject is obese.

In other embodiments, the invention relates to a method of treating or preventing insulin resistance disorders by administering a nicotinoyl riboside or derivative disclosed herein.

In further embodiments, the invention relates to a method of preventing a subject from growing an abnormally large organ comprising i) providing a) a subject and b) a composition comprising a nicotinoyl riboside or derivative; and ii) administering said composition to said subject under conditions such that the growth of an abnormally large organ is prevented. In further embodiments, said subject is a human. In further embodiments, said organ is the liver. In further embodiments, said subject is obese.

In some embodiments, the invention relates to a method of increasing the number of cellular mitochondria in a subject comprising i) providing a) a subject and b) a composition comprising a nicotinoyl riboside or derivative; and ii) administering said composition to said subject under conditions such that the number of cellular mitochondria increase in an organ of said subject increase. In further embodiments, said subject is a human. In further embodiments, said organ is the liver. In further embodiments, said subject is obese.

In further embodiments, the invention relates to a method of preventing heart disease in a subject comprising i) providing a) a subject and b) a composition comprising a nicotinoyl riboside or derivative; and ii) administering said composition to said subject under conditions such that heart disease is decreased. In further embodiments, said subject is a human. In further embodiments, said subject is obese.

In another embodiment, the invention relates to a nicotinoyl riboside or derivative administered with one or more therapeutic agents for the treatment or prevention of various diseases, including, for example, cancer, diabetes, neurodegenerative diseases, cardiovascular disease, blood clotting, inflammation, flushing, obesity, aging, stress, for example, administered with one or more of the following compounds: resveratrol, butein, fisetin, piceatannol, or quercetin. In an exemplary embodiment, nicotinoyl riboside or derivative may be administered in combination with nicotinic acid. In another embodiment, nicotinoyl riboside or derivative that decreases the level and/or activity of a sirtuin protein may be administered with one or more of the following compounds: nicotinamide (NAM), suranim; NF023 (a G-protein antagonist); NF279 (a purinergic receptor antagonist); Trolox (6-hydroxy-2,5,7,8,tetramethylchroman-2-carboxylic acid); (−)-epigallocatechin (hydroxy on sites 3,5,7,3',4',5'); (−)-epigallocatechin gallate (Hydroxy sites 5,7,3',4',5' and gallate ester on 3); cyanidin chloride (3,5,7,3',4'-pentahydroxyflavylium chloride); delphinidin chloride (3,5,7,3',4',5'-hexahydroxyflavylium chloride); myricetin (cannabiscetin; 3,5,7,3',4',5'-hexahydroxyflavone); 3,7,3',4',5'-pentahydroxyflavone; gossypetin (3,5,7,8,3',4'-hexahydroxyflavone), sirtinol; and splitomicin.

In further embodiments, the inventions relates to a nicotinoyl riboside or derivative administered to subjects within the Kingdom Monera, including the true bacteria (eubacteria) and cyanobacteria (blue-green algae). Such administration may be to control the growth and/or morphology of such subjects, for instance in the context of biotechnology production processes, or it may be in the context of treatment of another subject or object that is infected with subjects within the Kingdom Monera.

In further embodiments, the invention relates to a nicotinoyl riboside or derivative administered to subjects within the Kingdom Protista. Such administration may be in the context of treatment of another subject or object that is infected with subjects within the Kingdom Protista.

In further embodiments, the invention relates to a nicotinoyl riboside or derivative administered to subjects within the Kingdom Fungi. Such administration may be to control the growth and/or morphology of such subjects, for instance in the context of biotechnology production processes, or it may be in the context of treatment of another subject or object that is infected with subjects within the Kingdom Fungi.

In further embodiments, the invention relates to a nicotinoyl riboside or derivative administered to subjects within the Kingdom Plantae. Such administration may be to control the growth and/or morphology of such subjects, for instance in the context of biotechnology, agricultural, or horticultural production processes. Such administration may be to promote the growth of such subjects, or to prevent the growth or kill such subjects.

In further embodiments, the invention relates to a nicotinoyl riboside or derivative marketed in compliance with the United States Federal Food, Drug, and Cosmetic Act (21 U.S.C. 321) as a dietary supplement.

In further embodiments, the invention relates to a nicotinoyl riboside or derivative marketed in compliance with the United States Federal Food, Drug, and Cosmetic Act (21 U.S.C. 321) as a dietary supplement with antioxidant properties.

In further embodiments, the invention relates to a nicotinoyl riboside or derivative marketed in compliance with the United States Federal Food, Drug, and Cosmetic Act (21 U.S.C. 321) as a dietary supplement with health claims.

In further embodiments, the invention relates to a nicotinoyl riboside or derivative marketed in compliance with the United States Federal Food, Drug, and Cosmetic Act (21 U.S.C. 321) as a dietary supplement with health claims for reducing the risk of or preventing a disease.

In further embodiments, the invention relates to a nicotinoyl riboside or derivative marketed in compliance with the United States Federal Food, Drug, and Cosmetic Act (21 U.S.C. 321) as a dietary supplement with health claims for reducing the risk of or preventing any of the diseases described herein.

In further embodiments, the invention relates to a nicotinoyl riboside or derivative marketed in compliance with the United States Federal Food, Drug, and Cosmetic Act (21 U.S.C. 321) as a dietary supplement with structure/function claims.

In further embodiments, the invention relates to methods to synthesize a nicotinoyl riboside or derivative that is to be marketed as a dietary supplement.

DETAILED DESCRIPTION OF THE INVENTION

Figure 1:
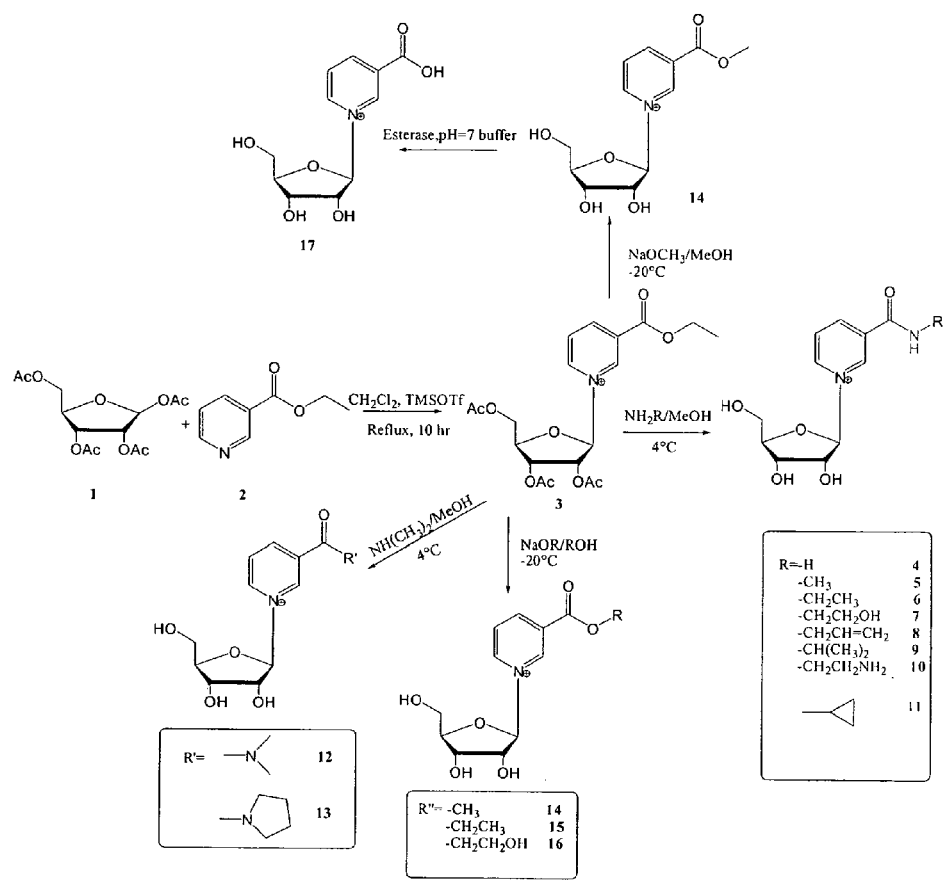
FIG. 1 shows a scheme of preferred methods of for preparing preferred compositions.

The invention relates to compositions of nicotinoyl ribosides and nicotinamide riboside derivatives and their methods of use. In some embodiments, the invention relates to methods of making nicotinoyl ribosides. In some embodiments, the invention relates to pharmaceutical compositions and nutritional supplements containing a nicotinoyl riboside. In further embodiments, the invention relates to methods of using nicotinoyl ribosides and nicotinamide riboside derivatives that promote the increase of intracellular levels of nicotinamide adenine dinucleotide (NAD+) in cells and tissues for improving cell and tissue survival.

A "nicotinoyl riboside" compound means a substituted or unsubstituted compound of the following formula:

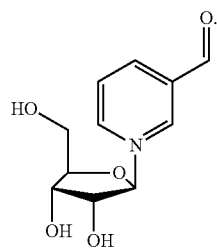

Nicotinoyl riboside "salts" refers to salts which make up the composition which specifically include the nicotinoyl riboside salt having the partial formula

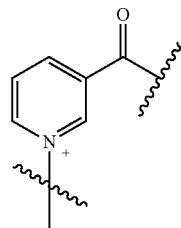

Z$^-$, and Z is a counter ion, including chloride, bromide, iodide, alkoxide, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

As used herein, the term "nicotinoyl riboside component" refers that part of a composition that contains all of the nicotinoyl riboside molecules in a given composition, including all conformational and stereomeric forms. In preferred embodiments, a given compound (e.g. designated by a structure) makes up a large percentage (e.g. by number of molecules and/or by weight) of the nicotinoyl riboside component. For example, a given nicotinoyl riboside molecule may be present in an aqueous composition at a level where 70% of all the nicotinoyl riboside molecules are of that given compound, while most of the composition itself is composed of water.

"Acyl" means an —C(=O)alkyl or —C(=O)aryl group.

"Adverse drug reaction" means any response to a drug that is noxious and unintended and occurs in doses for prophylaxis, diagnosis, or therapy including side effects, toxicity, hypersensitivity, drug interactions, complications, or other idiosyncrasy. Side effects are often adverse symptom produced by a therapeutic serum level of drug produced by its pharmacological effect on unintended organ systems (e.g., blurred vision from anticholinergic antihistamine). A toxic side effect is an adverse symptom or other effect produced by an excessive or prolonged chemical exposure to a drug (e.g., digitalis toxicity, liver toxicity). Hypersensitivities are immune-mediated adverse reactions (e.g., anaphylaxis, allergy). Drug interactions are adverse effects arising from interactions with other drugs, foods or disease states (e.g., warfarin and erythromycin, cisapride and grapefruit, loperamide and *Clostridium difficile* colitis). Complications are diseases caused by a drug (e.g., NSAID-induced gastric ulcer, estrogen-induced thrombosis). The adverse drug reaction may be mediated by known or unknown mechanisms (e.g., Agranulocytosis associated with chloramphenicol or clozapine). Such adverse drug reaction can be determined by subject observation, assay or animal model well-known in the art.

"Alkyl" means a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. The term "higher alkyl" has the same meaning as alkyl but contains from 2 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as a "homocycles" or "homocyclic rings." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Alkylamino" and "dialkylamino" mean one or two alkyl moiety attached through a nitrogen bridge (i.e., —N-alkyl) such as methylamino, ethylamino, dimethylamino, diethylamino, and the like.

"Alkylthiol" means an alkyl moiety attached through a sulfur bridge (i.e., —S-alkyl).

"Alkyloxy" means an alkyl moiety attached through an oxygen bridge (i.e., —O-alkyl) such as methoxy, ethoxy, and the like.

"Alkoxide" means an alkyl moiety attached to a negatively charged oxygen atom (i.e., $^-$Oalkyl) such as methoxide or ethoxide.

Within the context of certain embodiment, an "amine" means —NH$_2$ or "ammonia" the gas NH$_3$.

"Aryl" means an aromatic carbocyclic moiety such as phenyl or naphthyl.

"Aryloxy" means an aryl moiety attached through an oxygen bridge (i.e., —O-aryl).

"Arylthio" means an alkyl moiety attached through a sulfur bridge (i.e., —S-aryl).

"Aminooxy" means an amino moiety attached through an oxygen bridge (i.e., —O—NH$_2$).

"Hydroxylamino" means hydroxyl moiety attached through an amine bridge (i.e., —NH—OH).

"O-alkyloxyamino" means an alkyloxy moiety attached through an amine bridge (i.e., —NH—O-alkyl).

"N-alkylaminooxy" means an alkylamino moiety attached through an oxygen bridge (i.e., —O—NH-alkyl).

"Hydrazino" means an amino moiety attached through a nitrogen bridge (i.e., —NH—NH$_2$) depending on the context.

"Alkylhydrazino" means an alkyl moiety attached through a hydrazine bridge (i.e., —NH—NH-alkyl).

"Cancer" means any of various cellular diseases with malignant neoplasms characterized by the proliferation of an aplastic cells. It is not intended that the diseased cells must actually invade surrounding tissue and metastasize to new body sites. Cancer can involve any tissue of the body and have many different forms in each body area. Most cancers are named for the type of cell or organ in which they start.

Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, her2 for breast cancer, or others. For example, reduction of cancer may be identified in vitro using the following conditions for evaluation of apoptosis: i) Jurkat human T-cell leukemia cells are passed into flasks (250 mL, 75 cm$^2$) with 20 mL of supporting media; ii) after incubation at 37° C. with 5% CO$_2$, sample compound (or absent control) is added to a flask to make final concentration at 1 mM, and cells are incubated for another day; iii) cells are treated with 10 μM camptothecin and incubated with SYTOX Green reagent and annexin V allophycocyanin (APC) conjugate (invitrogen) and iv) Flow cytometry at 488 nm and 633 nm excitation. In cells undergoing apoptosis, phosphatidylserine (PS) is transferred from the cytoplasmic surface of the cell membrane to the outer leaflet. Annexin V has a high affinity for PS and dye conjugates provide indication of apoptosis by phosphatidylserine exposure and membrane integrity.

"Cells" means the structural unit of an organism consisting of one or more nuclei, cytoplasm, and various organelles, all surrounded by a semipermeable cell membrane.

"Growth media" are compositions used to grow microorganisms or cells in culture. There are different sorts of media for growing different sorts of cells. The biggest difference in growth media are between those used for growing cells in culture (cell culture uses specific cell types derived from plants or animals) and those used for growing microorganisms (usually bacteria or yeast). These differences arise due to the fact that cells derived from whole organisms and grown in culture are often incapable of growth without the provision of certain requirements, such as hormones or growth factors which usually occur in vivo. In the case of animal cells these requirements are often provided by the addition of blood serum to the medium. These media are often red or pink due to the inclusion of pH indicators. Growth media for embryonic stem cells preferably contains minimal essential medium, i.e., Eagle's: amino acids, salts (Ferric nitrate nonahydrate, Potassium chloride, Magnesium sulfate, Sodium chloride, Sodium dihydrogen phosphate), vitamins, (Ascorbic acid, Folic acid, Nicotinamide, Riboflavin, B-12) or Dulbecco's: additionally iron, glucose; non-essential amino acids, sodium pyruvate, β-mercaptoethanol, L-glutamine, fetal bovine serum and Leukemia Inhibitory Factor (LIF). In the case of microorganisms, there are no such limitations as they are often single cell organisms. One other major difference is that animal cells in culture are often grown on a flat surface to which they attach, and the medium is provided in a liquid form, which covers the cells. Bacteria such as *Escherichia coli* (*E. coli*, the most commonly used microbe in laboratories) may be grown on solid media or in liquid media, liquid nutrient medium is commonly called nutrient broth. The preferred growth media for microorganisms are nutrient broth or Luria-Bertani medium (L-B medium). Bacteria grown in liquid cultures often form colloidal suspensions. When agar (a substance which sets into a gel) is added to a liquid medium it can be poured into petri dishes where it will solidify (these are called agar plates) and provide a solid medium on which microbes may be cultured.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —CH$_2$pyridinyl, —CH$_2$pyrimidinyl, and the like.

"Heterocycle" (also referred to herein as a "heterocyclic ring") means a 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydropyranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH$_2$morpholinyl, and the like.

"Homocycle" (also referred to herein as "homocyclic ring") means a saturated or unsaturated (but not aromatic) carbocyclic ring containing from 3-7 carbon atoms, such as cyclopropane, cyclobutane, cyclopentane, cyclohexane, cycloheptane, cyclohexene, and the like.

"Isomers" means any of two or more substances that are composed of the same elements in the same proportions but differ in the three dimensional arrangement of atoms including enantiomeric (i.e., mirror images) and diastereomeric isomers.

"Methylene" means —CH$_2$—.

The term "derivative" when used in relation to a chemical compound refers to a similar structure that upon application, e.g., administration to a subject, is capable of providing, directly or indirectly, the function said chemical compound is disclosed to have. In the context of certain embodiments, a "nicotinamide riboside (NAR) derivative" is understood to not include the compound NAR.

A "tumor" means an abnormal mass of tissue growth that may be classified as benign or malignant.

The term "manage" when used in connection with a disease or condition means to provide beneficial effects to a subject being administered with a prophylactic or therapeutic agent, which does not result in a cure of the disease. In certain embodiments, a subject is administered with one or more prophylactic or therapeutic agents to manage a disease so as to prevent the progression or worsening of the disease.

Within the context of certain embodiments, the "health of a cell is managed" if more than a 3% increase in cell survival is observed for a sample compound compared to a control without the compound under the following conditions: i) cells are passed into flasks (250 mL, 75 cm$^2$) with 20 mL of media; ii) after 2 days incubation at 37° C. with 5% CO$_2$, sample compound (or absent control) is added to a flask to make final concentration at 1 mM, and cells are incubated for another day; iii) the agent methyl methanesulfonate (mms) (200 mM) is added to flask to make final concentration of 1 mM; iv) after 3 hrs incubation, the cells are harvested and the living ones are counted for the percentage of death with trypan blue (count cells on hemacytometer: dead cells stain blue, while live cells exclude trypan blue).

As used herein, the terms "prevent" and "preventing" include the prevention of the recurrence, spread or onset. It is not intended that the present invention be limited to complete prevention. In some embodiments, the onset is delayed, or the severity of the disease is reduced.

As used herein, the terms "purified isomer" and "purified isomer composition" are meant to indicate a composition (e.g. derived from a racemic mixture or synthesized de novo) wherein one isomer has been enriched (e.g., alpha-isomer) over the other (e.g., beta-isomer), and more preferably, wherein the other isomer represents less than 10%, and more preferably less than 7%, and still more preferably, less than 2% of the preparation.

Purified compositions in accordance with the invention preferably contain less than 5% mass/mass (m/m), advantageously less than 3% m/m, of impurities. It is to be understood that references herein to "impurities" are to be understood as to include unwanted reaction products that are not isomers formed during synthesis and does not include residual solvents remaining from the process used in the preparation of the composition or excipients used in pharmaceutical preparations.

The expression "essentially free" of a molecule means that the molecule is present in a composition only as an unavoidable impurity.

"Subject" means any animal, preferably a human patient, livestock, or domestic pet.

A "stem cell" is a cell that has the ability to divide (self replicate) and given the right signals, stem cells can give rise (differentiate) to several different cell types that make up a living organism. Many of the terms used to define stem cells depend on the behavior of the cells in the intact organism (in vivo), under specific laboratory conditions (in vitro), or after transplantation in vivo. For example, the fertilized egg is said to be totipotent because it has the potential to generate all the cells and tissues that make up an embryo and that support its development in utero. The fertilized egg divides and differentiates until it produces a mature organism. Other cells, which are important for embryonic development but are not incorporated into the body of the embryo, include the extraembryonic tissues, placenta, and umbilical cord. All of these cells are generated from a single, totipotent cell—the zygote, or fertilized egg.

"Pluripotent" cells have the potential to give rise to any type of cell, a property observed in the natural course of embryonic development. Unipotent stem cell, a term that is applied to a cell in adult organisms, means that the cells in question are capable of differentiating along only one lineage. The adult stem cells in many differentiated, undamaged tissues are typically unipotent and give rise to just one cell type under normal conditions. This process allows for a steady state of self-renewal for the tissue. However, if the tissue becomes damaged and the replacement of multiple cell types is required, pluripotent stem cells may become activated to repair the damage.

The "embryonic stem cell" (ES) is defined by its origin—that is from one of the earliest stages of the development of the embryo, called the blastocyst. Specifically, embryonic stem cells are derived from the inner cell mass of the blastocyst at a stage before it would implant in the uterine wall. At this stage, the preimplantation embryo of the mouse is made up of 150 cells and consists of a sphere made up of an outer layer of cells (the trophectoderm), a fluid-filled cavity (the blastocoel), and a cluster of cells on the interior (the inner cell mass). Pluripotent ES cells can give rise to differentiated cell types that are derived from all three primary germ layers of the embryo (endoderm, mesoderm, and ectoderm).

The "adult" stem cell is an undifferentiated (unspecialized) cell that is found in a differentiated (specialized) tissue; it can renew itself and become specialized to yield all of the specialized cell types of the tissue from which it originated. Adult stem cells are capable of self-renewal for the lifetime of the organism. Sources of adult stem cells have been found in the bone marrow, blood stream, cornea and retina of the eye, the dental pulp of the tooth, liver, skin, gastrointestinal tract, and pancreas. Unlike embryonic stem cells, there are no identifiable adult stem cells that are capable of forming all cells of the body. However, blood stem cells (derived from mesoderm) are able to generate a number of differentiated cells including both skeletal muscle (also derived from mesoderm) and neurons (derived from ectoderm).

The term "substituted" as used herein means any of the above groups (i.e., alkyl, aryl, arylalkyl, heteroaryl, heteroarylalkyl, homocycle, heterocycle and/or heterocyclealkyl) wherein at least one hydrogen atom is replaced with a substituent. In the case of an oxo substituent ("=O"), two hydrogen atoms are replaced. When substituted, one or more of the above groups are "substituents." Substituents within the context of this invention include halogen, deuterium, tritium, borono, hydroxy, oxo, cyano, nitro, amino, alkylamino, dialkylamino, alkyl, alkoxy, alkylthio, haloalkyl, aryl, arylalkyl, heteroaryl, heteroarylalkyl, heterocycle and heterocyclealkyl, as well as a saccharide, —NR$_a$R$_b$, —NR$_a$C(=O)R$_b$, —NR$_a$C(=O)NR$_a$NR$_b$, —NR$_a$C(=O)OR$_b$—NR$_a$SO$_2$R$_b$, —C(=O)R$_a$, C(=O)OR$_a$, —C(=O)NR$_a$R$_b$, —OC(=O) NR$_a$R$_b$, —OR$_a$, —SR$_a$, —SOR$_a$, —S(=O)$_2$R$_a$, —OS(=O)$_2$R$_a$ and —S(=O)$_2$OR$_a$. In addition, the above substituents may be further substituted with one or more of the above substituents, such that the substituent substituted alky, substituted aryl, substituted arylalkyl, substituted heterocycle or substituted heterocyclealkyl. R$_a$ and R$_b$ in this context may be the same or different and independently hydrogen, alkyl, haloalkyl, substituted alkyl, aryl, substituted aryl, arylalkyl, substituted arylalkyl, heterocycle, substituted heterocycle, heterocyclealkyl or substituted heterocyclealkyl. In the context of certain embodiments, a compound may be described as "unsubstituted" meaning that the compound does not contain extra substituents attached to the compound. An unsubstituted compound refers to the chemical makeup of the compound without extra substituents, e.g., the compound does not contain protecting group(s). For example, unsubstituted proline is the proline amino acid even though the amino group of proline may be considered disubstituted with alkyl groups.

As used herein, the terms "treat" and "treating" are not limited to the case where the subject (e.g. patient) is cured and the disease is eradicated. Rather, the present invention also contemplates treatment that merely reduces symptoms, and/or delays disease progression. "Diabetes" refers to high blood sugar or ketoacidosis, as well as chronic, general metabolic abnormalities arising from a prolonged high blood sugar status or a decrease in glucose tolerance. "Diabetes" encompasses both the type I and type II (Non Insulin Dependent Diabetes Mellitus or NIDDM) forms of the disease. The risk factors for diabetes may include but are not limited to the following factors: waistline of more than 40 inches for men or 35 inches for women, blood pressure of 130/85 mmHg or higher, triglycerides above 150 mg/dl, fasting blood glucose greater than 100 mg/dl or high-density lipoprotein of less than 40 mg/dl in men or 50 mg/dl in women.

The term "hyperinsulinemia" refers to a state in an individual in which the level of insulin in the blood is higher than normal.

The term "insulin resistance" refers to a state in which a normal amount of insulin produces a subnormal biologic response relative to the biological response in a subject that does not have insulin resistance.

An "insulin resistance disorder," as discussed herein, refers to any disease or condition that is caused by or contributed to by insulin resistance. Examples include: diabetes, obesity, metabolic syndrome, insulin-resistance syndromes, syndrome X, insulin resistance, high blood pressure, hypertension, high blood cholesterol, dyslipidemia, hyperlipidemia, dyslipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, peripheral neuropathy, nephropathy, glomerulonephritis, glomerulosclerosis, nephrotic syndrome, hypertensive nephrosclerosis some types of cancer (such as endometrial, breast, prostate, and colon), complications of pregnancy, poor female reproductive health (such as menstrual irregularities, infertility, irregular ovulation, polycystic ovarian syndrome (PCOS)), lipodystrophy, cholesterol related disorders, such as gallstones, cholescystitis and cholelithiasis, gout, obstructive sleep apnea and respiratory problems, osteoarthritis, and prevention and treatment of bone loss, e.g. osteoporosis.

"Obese" individuals or individuals suffering from obesity are generally individuals having a body mass index (BMI) of at least 25 or greater. Obesity may or may not be associated with insulin resistance.

The term "prophylactic" or "therapeutic" treatment is art-recognized and refers to administration of a drug to a host. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

Nicotinamide Adenine Dinucleotide Pathway

Figure 7:
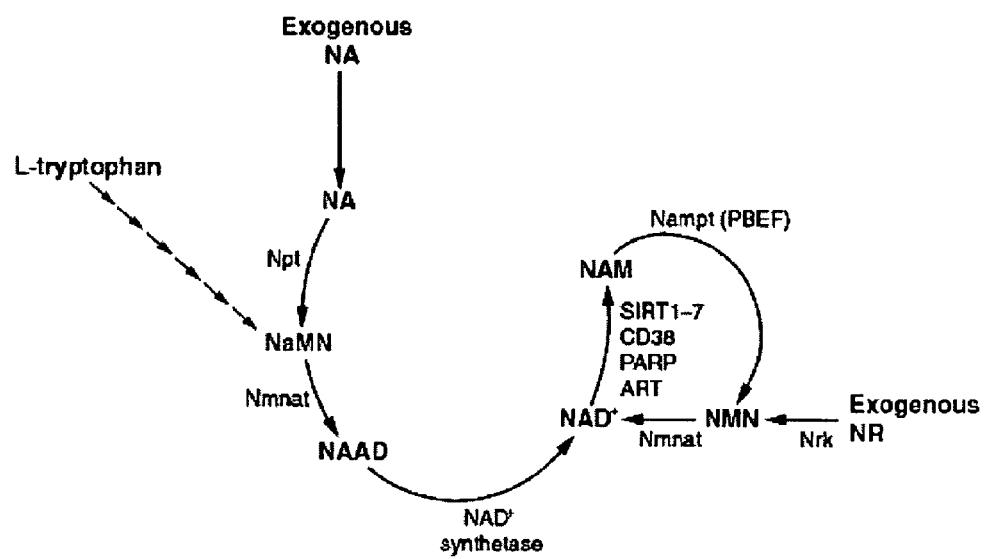
FIG. 7 shows NAD+ biosynthetic pathway in mammals. Abbreviations: NA, nicotinic acid; Npt, nicotinic acid phosphoribosyltransferase; NaMN, nicotinic acid mononucleotide; Nmnat, nicotinamide mononucleotide adenylyltransferase; NAAD, nicotinic acid adenine dinucleotide; NAM, nicotinamide; NMN, nicotinamide mononucleotide; NR, nicotinamide riboside; Nrk, nicotinamide riboside kinase; ART, ADP-ribosyl transferase; PARP, poly-ADP-polymerases; Nampt, nicotinamide phosphoribosyltransferase also known as pre-B cell colony-enhancing factor (PBEF).

Nicotinamide adenine dinucleotide (NAD or NAD+) is important as a co-enzyme for different enzymes. Recent studies depicted that being the co-substrate of SIR2 (silent information regulator 2), NAD+ has a role in regulating multiple biological processes, such as p53 regulated apoptosis, fat storage, stress resistance, and gene silencing. Without limiting the potential uses of the compositions described herein by any single theory, there are various pathways through which NAR is currently thought to be metabolized. Nicotinamide riboside (NAR) is known as a NAD+ precursor for both human and yeast. It is able to enter a salvage pathway that leads to biological synthesis of NAD+ under the action of the enzyme nicotinamide riboside kinase (Nrk). NAR is converted to NMN by Nrk, which is then converted to NAD+ by the enzyme nicotinamide mononucleotide adenylyltransferase (Nmnat). (see FIG. 7). Alternatively, nicotinamide riboside can enter NAD metabolism by means of other metabolic paths, which would include action from enzymes that separate the nicotinamide moiety from the sugar. Such a path would include the action of phosphorylases that have been shown to degrade NAR in cells to form nicotinamide and ribose-1-phosphate. Nicotinamide is competent to enter NAD+ metabolism and is converted to NAD+ by the action of the enzyme nicotinamide pyrophosphoribosyltransferase.

Sirtuins are class III histone deacetylases (HDACs) and are ADP-ribosyl transferases also. They deacetylate lysine residues in a novel chemical reaction that consumes nicotinamide adenine dinucleotide (NAD+), releasing nicotinamide, O-acetyl-ADPribose (AADPR), and the deacetylated substrate. Altering intracellular NAD+ levels can improve the health of a cell, but introduction of compounds that enter NAD+ metabolic pathways can also prove toxic to cells. In some embodiments, the invention relates to the use of compounds disclosed herein to manipulate NAD+ levels, to modulate the activity of sirtuins and other ADP-ribosyl transferases, and to modulate IMPHD. These embodiments are used to destroy or weaken the defenses of cancer cells, or to promote survival of neurons, myocytes, or stem cells via addition to growth media.

Nicotinic acid is an effective agent in controlling low-density lipoprotein cholesterol, increasing high-density lipoprotein cholesterol, and reducing triglyceride and lipoprotein (a) levels in humans. Though nicotinic acid treatment affects all of the key lipids in the desirable direction and has been shown to reduce mortality in target populations, its use is limited because of a side effect of heat and redness termed flushing. Further, nicotinamide protects against stroke injury in model systems, presumably due to multiple mechanisms including increasing mitochondrial NAD+ levels.

Accordingly, one embodiment, of the invention relates to the use of compositions comprising compounds disclosed herein that work through the nicotinamide riboside kinase pathway or other pathways of NAD+ biosynthesis which have nutritional and/or therapeutic value in improving plasma lipid profiles, prevention of stroke, and/or prolonging life and well-being. For example, nicotinamide riboside or nicotinic acid riboside or derivatives may be bioavailable but ultimately convertible by metabolism to nicotinic acid or nicotinamide, thereby providing the benefits of these compounds on lowering cholesterol or enhancing tissue protection from conditions of oxidative stress, such as is seen in stroke. This pathway of metabolism would predictably increase NAD metabolism in cells, besides providing effects observed for nicotinamide or nicotinic acid in therapy. Another aspect of the invention relates to a method for prevention or treating a disease or condition associated with the nicotinamide riboside kinase pathway or other pathways of NAD+ biosynthesis (see FIG. 7) by administering a composition comprising compounds disclosed herein. Diseases or conditions which typically have altered levels of NAD+ or precursors which can be prevented or treated by supplementing a diet or therapeutic treatment regime with a composition comprising compounds disclosed herein include, but are not limited to, lipid disorders, (e.g., dyslipidemia, hypercholesterolaemia or hyperlipidemia), stroke, type I and II diabetes, cardiovascular disease, and other physical problems associated with obesity.

In some embodiments, the invention relates to the use of compounds disclosed herein as agonist and antagonist of enzymes in the pathway of NAD+ biosynthesis. In further embodiments, the NAR derivatives disclosed herein are agonist, i.e., stimulates activities normally stimulated by naturally occurring substances, of one or more surtuins, preferably SIRT1 in humans or Sir2p in yeast. In further embodiments, the NAR derivatives are antagonist of one or surtuins.

Although the applicant does not intend that the invention be limited by any particular mechanism, this is believed to be useful because SIRT1 deacetylates transcription factors such as FOXOs, p53, and nuclear factor Kappa B (NFKB), that provide stress resistance, apoptosis, and inflammatory responses improving organism survival. The sirtuin SIRT1 upregulates stress-protective pathways by deacetylation of FOXO transcription factors, leading to increased transcription of GADD45 (DNA repair) and MnSOD (reactive oxygen detoxification). SIRT1 concomitantly downregulates FOXO transcription of the proapoptotic factors Fas and Bcl-2 interacting mediator of cell death. (BIM).

For example, the p53 network in normal, non-activated situations is non-functional, but is activated in cells as a response to various signals by inhibiting the abnormal growth of cells and triggering of programmed cell death. SIRT1 interacts with p53 and deacetylates the C-terminal regulatory domain. This activity downregulates effects of p53 transcriptional activation on target genes.

Neurodegenerative Diseases

Axon degeneration occurs frequently in neurodegenerative diseases and peripheral neuropathies. The degeneration of transected axons is delayed in Wallerian degeneration slow (Wlds) mice with the overexpression of a fusion protein with the nicotinamide adenine dinucleotide (NAD+) synthetic enzyme, nicotinamide mononucleotide adenylyltransferase (Nmnat1). Both Wld(s) and Nmnat1 themselves are functional in preventing axon degeneration in neuronal cultures.

NAD+ levels decrease in injured, diseased, or degenerating neural cells and preventing this NAD+ decline efficiently protects neural cells from cell death. Araki & Milbrandt "Increased nuclear NAD+ biosynthesis and SIRT1 activation prevent axonal degeneration" Science. 2004 Aug. 13; 305 (5686):1010-3 and Wang et al., "A local mechanism mediates NAD-dependent protection of axon degeneration" J Cell Biol. 170(3):349-55 (2005) hereby incorporated by reference. As a number of nicotinoyl riboside compounds disclosed herein are capable of increasing intracellular levels of NAD+, these compounds are useful as a therapeutic or nutritional supplement in managing injuries, diseases, and disorders effecting the central nervous system and the peripheral nervous system, including but not limited to trauma or injury to neural cells, diseases or conditions that harm neural cells, and neurodegenerative diseases or syndromes. Some neurodegenerative diseases, neurodegenerative syndromes, diseases and conditions that harm neural cells, and injury to neural cells are described below.

Essential tremor (ET) is the most common movement disorder. It is a syndrome characterized by a slowly progressive postural and/or kinetic tremor, usually affecting both upper extremities.

Parkinson disease (PD) is a progressive neurodegenerative disorder associated with a loss of dopaminergic nigrostriatal neurons.

Alzheimer disease (AD) is the most common form of dementia. It is a progressive degenerative disease of the brain, strongly associated with advanced age. Over time, people with the disease lose their ability to think and reason clearly, judge situations, solve problems, concentrate, remember useful information, take care of themselves, and even speak. A number of neurodegenerative disease such as Alzheimer's disease execute their biological impact in the brain. It is preferred that nicotinoyl riboside compounds disclosed herein are capable of passing the blood-brain-barrier (BBB).

Huntington disease (HD) is an incurable, adult-onset, autosomal dominant inherited disorder associated with cell loss within a specific subset of neurons in the basal ganglia and cortex.

Ataxia is defined as an inability to maintain normal posture and smoothness of movement. Neurologic symptoms and signs such as seizures and movement disorders (eg, dystonia, chorea) may accompany ataxia.

Catatonia is a state of apparent unresponsiveness to external stimuli in a person who is apparently awake. Epilepsy is defined as a chronic condition characterized by spontaneous, recurrent seizures; seizure is defined as a clinical event associated with a transient, hypersynchronous neuronal discharge.

Neuroleptic malignant syndrome (NMS) refers to the combination of hyperthermia, rigidity, and autonomic dysregulation that can occur as a serious complication of the use of antipsychotic drugs.

Chorea is an involuntary abnormal movement, characterized by abrupt, brief, nonrhythmic, nonrepetitive movement of any limb, often associated with nonpatterned facial grimaces. Chorea gravidarum (CG) is the term given to chorea occurring during pregnancy.

Cortical basal ganglionic degeneration (CBGD) clinical characteristic include progressive dementia, parkinsonism, and limb apraxia. Dysfunction of the central or peripheral nervous system pathways may cause autonomic dysfunction.

Dystonia is a syndrome of sustained muscle contractions, usually producing twisting and repetitive movements or abnormal postures. Writer's cramp is a form of task-specific focal dystonia.

Mental retardation (MR) is a condition in which intellectual capacity is limited significantly. Developmental disability describes a condition that limits an individual's ability to perform activities and roles as expected in a certain social environment. Frequently, MR and developmental disabilities are present simultaneously as a consequence of brain damage.

Neuroacanthocytosis is a progressive neurologic disease characterized by movement disorders, personality changes, cognitive deterioration, axonal neuropathy, and seizures. Most patients have acanthocytosis on peripheral blood smear at some point during the course of the disease.

Pelizaeus-Merzbacher disease (PMD) and X-linked spastic paraplegia type 2 (SPG2) are at opposite ends of a clinical spectrum of X-linked diseases caused by mutations of the same gene, the proteolipid protein 1 (PLP1) gene, and resulting in defective central nervous system (CNS) myelination. Clinical signs usually include some combination of nystagmus, stridor, spastic quadriparesis, hypotonia, cognitive impairment, ataxia, tremor, and diffuse leukoencephalopathy on MRI scans.

Progressive supranuclear palsy (PSP), also known as Steele-Richardson-Olszewski syndrome, is a neurodegenerative disease that affects cognition, eye movements, and posture.

Striatonigral degeneration (SND) is a neurodegenerative disease that represents a manifestation of multiple system atrophy (MSA). The other manifestations are Shy-Drager syndrome (eg, autonomic failure predominates) and sporadic olivopontocerebellar degeneration (sOPCA, cerebellum predominates).

Tardive dyskinesias (TDs) are involuntary movements of the tongue, lips, face, trunk, and extremities that occur in patients treated with long-term dopaminergic antagonist medications. Although they are associated with the use of neuroleptics, TDs apparently existed before the development of neuroleptics. People with schizophrenia appear especially vulnerable to developing TDs after exposure to neuroleptics, toxins, and other agents. TDs are most common in patients with schizophrenia, schizoaffective disorder, or bipolar disorder who have been treated with antipsychotic medication for long periods, but TDs occasionally occur in other patients as well.

The lysosomal storage diseases are a group of which over forty disorders are currently known that result from defects in lysosomal function. Lysosomes are cytoplasmic organelles that contain enzymes (specifically, acid hydrolases) that break macromolecules down to peptides, amino acids, monosaccharides, nucleic acids and fatty acids. The lysosomal storage diseases are classified by the nature of the primary stored material involved, and can be broadly broken into the following: (ICD-10 codes are provided where available)
- (E75) lipid storage disorders (including Gaucher's and Niemann-Pick diseases)
- (E75.0-E75.1) gangliosidosis (including Tay-Sachs disease)
- (E75.2) leukodystrophies
- (E76.0) mucopolysaccharidoses
- (E77) glycoprotein storage disorders
- (E77.0-E77.1) mucolipidoses Ischemic stroke occurs due to a loss of blood supply to part of the brain, initiating the ischemic cascade. Brain tissue ceases to function if deprived of oxygen for more than 60 to 90 seconds and after a few hours will suffer irreversible injury possibly leading to death of the tissue, i.e., infarction. Atherosclerosis may disrupt the blood supply by narrowing the lumen of blood vessels leading to a reduction of blood flow, by causing the formation of blood clots within the vessel, or by releasing showers of small emboli through the disintegration of atherosclerotic plaques. Embolic infarction occurs when emboli formed elsewhere in the circulatory system, typically in the heart as a consequence of atria fibrillation, or in the carotid arteries. These break off, enter the cerebral circulation, then lodge in and occlude brain blood vessels.

Due to collateral circulation, within the region of brain tissue affected by ischemia there is a spectrum of severity. Thus, part of the tissue may immediately die while other parts may only be injured and could potentially recover. The ischemia area where tissue might recover is referred to as the ischemic penumbra.

As oxygen or glucose becomes depleted in ischemic brain tissue, the production of high energy phosphate compounds such as adenine triphosphate (ATP) fails leading to failure of energy dependent processes necessary for tissue cell survival. This sets off a series of interrelated events that result in cellular injury and death. These include the failure of mitochondria, which can lead further toward energy depletion and may trigger cell death due to apoptosis. Other processes include the loss of membrane ion pump function leading to electrolyte imbalances in brain cells. There is also the release of excitatory neurotransmitters, which have toxic effects in excessive concentrations.

Ischaemia also induces production of oxygen free radicals and other reactive oxygen species. These react with and damage a number of cellular and extracellular elements. Damage to the blood vessel lining or endothelium is particularly important. In fact, many antioxidant neuroprotectants such as uric acid and NXY-059 work at the level of the endothelium and not in the brain per se. Free radicals also directly initiate elements of the apoptosis cascade by means of redox signaling.

These processes are the same for any type of ischemic tissue and are referred to collectively as the ischemic cascade. However, brain tissue is especially vulnerable to ischemia since it has little respiratory reserve and is completely dependent on aerobic metabolism, unlike most other organs.

Spinal cord injury, or myelopathy, is a disturbance of the spinal cord that results in loss of sensation and mobility. The two common types of spinal cord injury are:
- Trauma: automobile accidents, falls, gunshots, diving accidents, etc.
- Disease: polio, spina bifida, tumors, Friedreich's ataxia, etc.

It is important to note that the spinal cord does not have to be completely severed for there to be a loss of function. In fact, the spinal cord remains intact in most cases of spinal cord injury.

About 450,000 people in the United States live with spinal cord injury, and there are about 11,000 new spinal cord injuries every year. The majority of them (78%) involve males between the ages of 16-30 and result from motor vehicle accidents (42%), violence (24%), or falls (22%).

In a complete injury, there is no function below the level of the injury. Voluntary movement is impossible and physical sensation is impossible. Complete injuries are always bilateral, that is, both sides of the body are affected equally.

A person with an incomplete injury retains some sensation below the level of the injury. Incomplete injuries are variable, and a person with such an injury may be able to move one limb more than another, may be able to feel parts of the body that cannot be moved, or may have more functioning on one side of the body than the other.

In addition to a loss of sensation and motor function below the point of injury, individuals with spinal cord injuries will often experience other changes. Bowel and bladder function is associated with the sacral region of the spine, so it is very common to experience dysfunction of the bowel and bladder. Sexual function is also associated with the sacral region, and is also affected very often. Injuries very high on the spinal cord (C-1, C-2) will often result in a loss of many involuntary functions, such as breathing, necessitating mechanical ventilators or phrenic nerve pacing. Other effects of spinal cord injury can include an inability to regulate heart rate (and therefore blood pressure), reduced control of body temperature, inability to sweat below the level of injury, and chronic pain. Physical therapy and orthopedic instruments (e.g., wheelchairs, standing frames) are often necessary, depending on the location of the injury. Between about three weeks and twelve years after lesions above T10 autonomic dysreflexia may occur.

The injury may be located anywhere along the spinal cord; injuries are usually classified by location: Cervical injuries;

Thoracic injuries; Lumbar and Sacral injuries; and Central Cord Syndrome. Central Cord Syndrome is associated with ischemia, hemorrhage, or necrosis involving the central portions of the spinal cord (the large nerve fibers that carry information directly from the cerebral cortex). Corticospinal fibers destined for the legs are spared due to their more external location in the spinal cord.

Traumatic brain injury (TBI), traumatic injuries to the brain, also called intracranial injury, or simply head injury, occurs when a sudden trauma causes brain damage. TBI can result from a closed head injury or a penetrating head injury and is one of two subsets of acquired brain injury (ABI). The other subset is non-traumatic brain injury (i.e. stroke, meningitis, anoxia). Parts of the brain that can be damaged include the cerebral hemispheres, cerebellum, and brain stem. Symptoms of a TBI can be mild, moderate, or severe, depending on the extent of the damage to the brain. Outcome can be anything from complete recovery to permanent disability or death. A coma can also affect a child's brain. The damage from TBI can be focal, confined to one area of the brain, or diffuse, involving more than one area of the brain. Diffuse trauma to the brain is frequently associated with concussion (a shaking of the brain in response to sudden motion of the head), diffuse axonal injury, or coma. Localized injuries may be associated with neurobehavioral manifestations, hemiparesis or other focal neurologic deficits.

Types of focal brain injury include bruising of brain tissue called a contusion and intracranial hemorrhage or hematoma, heavy bleeding in the skull. Hemorrhage, due to rupture of a blood vessel in the head, can be extra-axial, meaning it occurs within the skull but outside of the brain, or intra-axial, occurring within the brain. Extra-axial hemorrhages can be further divided into subdural hematoma, epidural hematoma, and subarachnoid hemorrhage. An epidural hematoma involves bleeding into the area between the skull and the dura. With a subdural hematoma, bleeding is confined to the area between the dura and the arachnoid membrane. A subarachnoid hemorrhage involves bleeding into the space between the surface of the brain and the arachnoid membrane that lies just above the surface of the brain, usually resulting from a tear in a blood vessel on the surface of the brain. Bleeding within the brain itself is called an intracerebral hematoma. Intra-axial bleeds are further divided into intraparenchymal hemorrhage which occurs within the brain tissue itself and intraventricular hemorrhage which occurs into the ventricular system.

TBI can result from a closed head injury or a penetrating head injury. A closed injury occurs when the head suddenly and violently hits an object but the object does not break through the skull. A penetrating injury occurs when an object pierces the skull and enters brain tissue.

As the first line of defense, the skull is particularly vulnerable to injury. Skull fractures occur when the bone of the skull cracks or breaks. A depressed skull fracture occurs when pieces of the broken skull press into the tissue of the brain. A penetrating skull fracture occurs when something pierces the skull, such as a bullet, leaving a distinct and localized traumatic injury to brain tissue. Skull fractures can cause cerebral contusion.

Another insult to the brain that can cause injury is anoxia. Anoxia is a condition in which there is an absence of oxygen supply to an organ's tissues, even if there is adequate blood flow to the tissue. Hypoxia refers to a decrease in oxygen supply rather than a complete absence of oxygen, and ischemia is inadequate blood supply, as is seen in cases in which the brain swells. In any of these cases, without adequate oxygen, a biochemical cascade called the ischemic cascade is unleashed, and the cells of the brain can die within several minutes. This type of injury is often seen in near-drowning victims, in heart attack patients (particularly those who have suffered a cardiac arrest, or in people who suffer significant blood loss from other injuries that then causes a decrease in blood flow to the brain due to circulatory (hypovolemic) shock.

Sometimes, health complications occur in the period immediately following a TBI. These complications are not types of TBI, but are distinct medical problems that arise as a result of the injury. Although complications are rare, the risk increases with the severity of the trauma. Complications of TBI include immediate seizures, hydrocephalus or post-traumatic ventricular enlargement, cerebrospinal fluid leaks, infections, vascular injuries, cranial nerve injuries, pain, bed sores, multiple organ system failure in unconscious patients, and polytrauma (trauma to other parts of the body in addition to the brain).

About 25% of patients with brain contusions or hematomas and about 50% of patients with penetrating head injuries will develop immediate seizures, seizures that occur within the first 24 hours of the injury. These immediate seizures increase the risk of early seizures—defined as seizures occurring within 1 week after injury—but do not seem to be linked to the development of post-traumatic epilepsy (recurrent seizures occurring more than 1 week after the initial trauma). Generally, medical professionals use anticonvulsant medications to treat seizures in TBI patients only if the seizures persist.

Hydrocephalus or post-traumatic ventricular enlargement occurs when cerebrospinal fluid (CSF) accumulates in the brain resulting in dilation of the cerebral ventricles (cavities in the brain filled with CSF) and an increase in ICP. This condition can develop during the acute stage of TBI or may not appear until later. Generally it occurs within the first year of the injury and is characterized by worsening neurological outcome, impaired consciousness, behavioral changes, ataxia (lack of coordination or balance), incontinence, or signs of elevated ICP. The condition may develop as a result of meningitis, subarachnoid hemorrhage, intracranial hematoma, or other injuries. Treatment includes shunting and draining of CSF as well as any other appropriate treatment for the root cause of the condition.

Skull fractures can tear the membranes that cover the brain, leading to CSF leaks. A tear between the dura and the arachnoid membranes, called a CSF fistula, can cause CSF to leak out of the subarachnoid space into the subdural space; this is called a subdural hygroma. CSF can also leak from the nose and the ear. These tears that let CSF out of the brain cavity can also allow air and bacteria into the cavity, possibly causing infections such as meningitis. Pneumocephalus occurs when air enters the intracranial cavity and becomes trapped in the subarachnoid space.

Infections within the intracranial cavity are a dangerous complication of TBI. They may occur outside of the dura mater, below the dura, below the arachnoid (meningitis), or within the brain itself (abscess). Most of these injuries develop within a few weeks of the initial trauma and result from skull fractures or penetrating injuries. Standard treatment involves antibiotics and sometimes surgery to remove the infected tissue. Meningitis may be especially dangerous, with the potential to spread to the rest of the brain and nervous system.

Any damage to the head or brain usually results in some damage to the vascular system, which provides blood to the cells of the brain. The body's immune system can repair damage to small blood vessels, but damage to larger vessels can result in serious complications. Damage to one of the major arteries leading to the brain can cause a stroke, either through bleeding from the artery (hemorrhagic stroke) or through the formation of a clot at the site of injury, called a thrombus or thrombosis, blocking blood flow to the brain (ischemic stroke). Blood clots also can develop in other parts of the head. Symptoms such as headache, vomiting, seizures, paralysis on one side of the body, and semiconsciousness developing within several days of a head injury may be caused by a blood clot that forms in the tissue of one of the sinuses, or cavities, adjacent to the brain. Thrombotic-ischemic strokes are treated with anticoagulants, while surgery is the preferred treatment for hemorrhagic stroke. Other types of vascular injuries include vasospasm and the formation of aneurysms.

Skull fractures, especially at the base of the skull, can cause cranial nerve injuries that result in compressive cranial neuropathies. All but three of the 12 cranial nerves project out from the brainstem to the head and face. The seventh cranial nerve, called the facial nerve, is the most commonly injured cranial nerve in TBI and damage to it can result in paralysis of facial muscles.

Pain, especially headache, is commonly a significant complication for conscious patients in the period immediately following a TBI. Serious complications for patients who are unconscious, in a coma, or in a vegetative state include bed or pressure sores of the skin, recurrent bladder infections, pneumonia or other life-threatening infections, and progressive multiple organ failure.

Drug Toxicity

In some embodiments, the invention relates to the use of a nicotinoyl riboside or derivative to prevent adverse effects and protect cells from toxicity. Toxicity may be an adverse effect of radiation or external chemicals on the cells of the body. Examples of toxins are pharmaceuticals, drugs of abuse, and radiation, such as UV or X-ray light. Both radiative and chemical toxins have the potential to damage biological molecules such as DNA. This damage typically occurs by chemical reaction of the exogenous agent or its metabolites with biological molecules, or indirectly through stimulated production of reactive oxygen species (eg, superoxide, peroxides, hydroxyl radicals). Repair systems in the cell excise and repair damage caused by toxins.

Enzymes that use NAD+ play an part in the DNA repair process. Specifically, the poly(ADP-ribose) polymerases (PARPs), particularly PARP-1, are activated by DNA strand breaks and affect DNA repair. The PARPs consume NAD+ as an adenosine diphosphate ribose (ADPR) donor and synthesize poly(ADP-ribose) onto nuclear proteins such as histones and PARP itself. Although PARP activities facilitate DNA repair, overactivation of PARP can cause significant depletion of cellular NAD+, leading to cellular necrosis. The apparent sensitivity of NAD+ metabolism to genotoxicity has led to pharmacological investigations into the inhibition of PARP as a means to improve cell survival. Numerous reports have shown that PARP inhibition increases NAD+ concentrations in cells subject to genotoxicity, with a resulting decrease in cellular necrosis. Nevertheless, cell death from toxicity still occurs, presumably because cells are able to complete apoptotic pathways that are activated by genotoxicity. Thus, significant cell death is still a consequence of DNA/macromolecule damage, even with inhibition of PARP. This consequence suggests that improvement of NAD+ metabolism in genotoxicity can be partially effective in improving cell survival but that other players that modulate apoptotic sensitivity, such as sirtuins, may also play important roles in cell responses to genotoxins.

Physiological and biochemical mechanisms that determine the effects of chemical and radiation toxicity in tissues are complex, and evidence indicates that NAD+ metabolism is an important player in cell stress response pathways. For example, upregulation of NAD+ metabolism, via nicotinamide/nicotinic acid mononucleotide (NMNAT) overexpression, has been shown to protect against neuron axonal degeneration, and nicotinamide used pharmacologically has been recently shown to provide neuron protection in a model of fetal alcohol syndrome and fetal ischemia. Such protective effects could be attributable to upregulated NAD+ biosynthesis, which increases the available NAD+ pool subject to depletion during genotoxic stress. This depletion of NAD+ is mediated by PARP enzymes, which are activated by DNA damage and can deplete cellular NAD+, leading to necrotic death. Another mechanism of enhanced cell protection that could act in concert with upregulated NAD+ biosynthesis is the activation of cell protection transcriptional programs regulated by sirtuin enzymes.

Examples of cell and tissue protection linked to NAD+ and sirtuins include the finding that SIRT1 is required for neuroprotection associated with trauma and genotoxicity. SIRT1 can also decrease microglia-dependent toxicity of amyloid-beta through reduced NFKB signaling. SIRT1 and increased NAD+ concentrations provide neuroprotection in a model of Alzheimer's disease. Sirtuins are NAD+-dependent enzymes that have protein deacetylase and ADP-ribosyltransferase activities that upregulate stress response pathways. Evidence indicates that SIRT1 is upregulated by calorie restriction and in humans could provide cells with protection against apoptosis via downregulation of p53 and Ku70 functions. In addition, SIRT1 upregulates FOXO-dependent transcription of proteins involved in reactive oxygen species (ROS) detoxification, such as MnSOD. The sirtuin SIRT6 has been shown to participate in DNA repair pathways and to help maintain genome stability.

It seems likely that pharmacological agents that target both NAD+ metabolism and sirtuins could provide tools to elucidate the involvement of these factors in modulating toxicity-induced tissue damage. Moreover, therapeutic options for treatment of acute and chronic tissue-degenerative conditions could emerge if sirtuins and NAD+ metabolism can be validated as providing enhanced tissue protection. Agents such as the plant polyphenols (eg, resveratrol), the niacin vitamins, and the compound nicotinamide riboside may enhance cell survival outcomes by increasing NAD+ biosynthesis, reducing NAD+ depletion, and/or activating sirtuin enzymes.

Statins, more mechanistically known as 3-hydroxy-3-methyglutaryl coenzyme A reductase inhibitors (or HMG-CoA inhibitors) are some of the world's most widely prescribed drugs. While statins are well tolerated at therapeutic doses, at higher doses and often in combination with other hypolipidaemic agents some potentially severe adverse effects have arisen. Most notably, cerivastatin (Baycol) was removed from the market in 2000 after 31 deaths in the United States from drug-associated rhabdomyolysis (breakdown of muscle fibers resulting in the release of muscle fiber contents into the circulation; some of these are toxic to the kidney) and associated acute renal failure in patients taking cerivastatin. Statins are also known to have severe interactions with fibric acid derivatives, especially with gemfibrozil. Of the 31 people who died taking cerivastatin, 12 were also taking gemfibrozil.

The most serious adverse effects of statins appear to occur in liver and muscle cells, although it could be predicted that because of their lipophilicity, cerebral effects might also be seen in some patients.

The exact mechanism of statin toxicities is unknown. The fact that toxicities are dose-dependent makes plausible the hypothesis that toxicities result from exaggeration of the drug's intended effect: in other words, cells die from lack of the downstream products of HMG-CoA.

HMG-CoA is the rate limiting enzyme in the mevalonate pathway, which, through three branches, leads to the synthesis of cholesterol, dolichol (the precursor to dolichol pyrophosphate, which is the first thing added to proteins in post-translational glycosylation), and to ubiquinone, also known as Coenzyme Q (found in the membranes of endoplasmic reticulum, peroxisomes, lysosomes, vesicles and notably the inner membrane of the mitochondrion where it is an important part of the electron transport chain; it is also has important antioxidant activities).

However, it is likely that depletion of CoQ leads to a breakdown in the electron transport chain, leading in turn to a buildup in NADH, and a depletion in NAD+. Further, the reduced form of CoQ10, CoQ10H2, has an important cellular antioxidant function, which is to protect membranes and plasma lipoproteins against free radical-induced oxidation.

Aging/Stress

In one embodiment, the invention provides a method extending the lifespan of a cell, extending the proliferative capacity of a cell, slowing aging of a cell, promoting the survival of a cell, delaying cellular senescence in a cell, mimicking the effects of calorie restriction, increasing the resistance of a cell to stress, or preventing apoptosis of a cell, by contacting the cell with nicotinoyl riboside or derivative compound. In an exemplary embodiment, the methods comprise contacting the cell with a nicotinoyl riboside or derivative.

The methods described herein may be used to increase the amount of time that cells, particularly primary cells (i.e., cells obtained from an organism, e.g., a human), may be kept alive in a cell culture. Embryonic stem (ES) cells and pluripotent cells, and cells differentiated therefrom, may also be treated with nicotinoyl riboside or derivative compound to keep the cells, or progeny thereof, in culture for longer periods of time. Such cells can also be used for transplantation into a subject, e.g., after ex vivo modification.

In one embodiment, cells that are intended to be preserved for long periods of time may be treated with a nicotinoyl riboside or derivative compound. The cells may be in suspension (e.g., blood cells, serum, biological growth media, etc.) or in tissues or organs. For example, blood collected from an individual for purposes of transfusion may be treated with a nicotinoyl riboside or derivative compound to preserve the blood cells for longer periods of time. Additionally, blood to be used for forensic purposes may also be preserved using a nicotinoyl riboside or derivative compound. Other cells that may be treated to extend their lifespan or protect against apoptosis include cells for consumption, e.g., cells from non-human mammals (such as meat) or plant cells (such as vegetables).

Nicotinoyl riboside or derivative compounds may also be applied during developmental and growth phases in mammals, plants, insects or microorganisms, in order to, e.g., alter, retard or accelerate the developmental and/or growth process.

In another embodiment, a nicotinoyl riboside or derivative compounds may be used to treat cells useful for transplantation or cell therapy, including, for example, solid tissue grafts, organ transplants, cell suspensions, stem cells, bone marrow cells, etc. The cells or tissue may be an autograft, an allograft, a syngraft or a xenograft. The cells or tissue may be treated with the a nicotinoyl riboside or derivative compound prior to administration/implantation, concurrently with administration/implantation, and/or post administration/implantation into a subject. The cells or tissue may be treated prior to removal of the cells from the donor individual, ex vivo after removal of the cells or tissue from the donor individual, or post implantation into the recipient. For example, the donor or recipient individual may be treated systemically with a nicotinoyl riboside or derivative compound or may have a subset of cells/tissue treated locally with a nicotinoyl riboside or derivative compound. In certain embodiments, the cells or tissue (or donor/recipient individuals) may additionally be treated with another therapeutic agent useful for prolonging graft survival, such as, for example, an immunosuppressive agent, a cytokine, an angiogenic factor, etc.

In yet other embodiments, cells may be treated with a nicotinoyl riboside or derivative compound that increases the level of NAD+ in vivo, e.g., to increase their lifespan or prevent apoptosis. For example, skin can be protected from aging (e.g., developing wrinkles, loss of elasticity, etc.) by treating skin or epithelial cells with a nicotinoyl riboside or derivative compound that increases the level intracellular NAD+. In an exemplary embodiment, skin is contacted with a pharmaceutical or cosmetic composition comprising a nicotinoyl riboside or derivative compound that increases the level of intracellular NAD+. Exemplary skin afflictions or skin conditions that may be treated in accordance with the methods described herein include disorders or diseases associated with or caused by inflammation, sun damage or natural aging. For example, the compositions find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In another embodiment, a nicotinoyl riboside or derivative compound that increases the level of intracellular NAD+ may be used for the treatment of wounds and/or burns to promote healing, including, for example, first-, second- or third-degree burns and/or thermal, chemical or electrical burns. The formulations may be administered topically, to the skin or mucosal tissue, as an ointment, lotion, cream, microemulsion, gel, solution or the like, as further described herein, within the context of a dosing regimen effective to bring about the desired result.

Topical formulations comprising one or more a nicotinoyl riboside or derivative compound that increases the level of intracellular NAD+ may also be used as preventive, e.g., chemopreventive, compositions. When used in a chemopreventive method, susceptible skin is treated prior to any visible condition in a particular individual.

In another embodiment, a nicotinoyl riboside or derivative compound that increases the level of intracellular NAD+ may be used for treating or preventing a disease or condition induced or exacerbated by cellular senescence in a subject; methods for decreasing the rate of senescence of a subject, e.g., after onset of senescence; methods for extending the lifespan of a subject; methods for treating or preventing a disease or condition relating to lifespan; methods for treating or preventing a disease or condition relating to the proliferative capacity of cells; and methods for treating or preventing a disease or condition resulting from cell damage or death. In certain embodiments, the method does not act by decreasing the rate of occurrence of diseases that shorten the lifespan of a subject. In certain embodiments, a method does not act by reducing the lethality caused by a disease, such as cancer.

In yet another embodiment, a nicotinoyl riboside or derivative compound that increases the level of intracellular NAD+ may be administered to a subject in order to generally increase the lifespan of its cells and to protect its cells against stress and/or against apoptosis. It is believed that treating a subject with a compound described herein is similar to subjecting the subject to hormesis, i.e., mild stress that is beneficial to organisms and may extend their lifespan.

A nicotinoyl riboside or derivative compound that increases the level of intracellular NAD+ can also be administered to subjects for treatment of diseases, e.g., chronic diseases, associated with cell death, in order to protect the cells from cell death. Exemplary diseases include those associated with neural cell death, neuronal dysfunction, or muscular cell death or dysfunction, such as Parkinson's disease, Alzheimer's disease, multiple sclerosis, amyotropic lateral sclerosis, and muscular dystrophy; AIDS; fulminant hepatitis; diseases linked to degeneration of the brain, such as Creutzfeld-Jakob disease, retinitis pigmentosa and cerebellar degeneration; myelodysplasis such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections. Cell death can also be caused by surgery, drug therapy, chemical exposure or radiation exposure.

A nicotinoyl riboside or derivative compound that increases the level of intracellular NAD+ can also be administered to a subject suffering from an acute disease, e.g., damage to an organ or tissue, e.g., a subject suffering from stroke or myocardial infarction or a subject suffering from a spinal cord injury. A nicotinoyl riboside or derivative compound that increases the level of intracellular NAD+ may also be used to repair an alcoholic's liver.

Cardiovascular Disease

In another embodiment, the invention provides a method for treating and/or preventing a cardiovascular disease by administering to a subject in need thereof a nicotinoyl riboside or derivative compound that increases the level of intracellular NAD+.

Cardiovascular diseases that can be treated or prevented a nicotinoyl riboside or derivative compound that increases the level of intracellular NAD+ include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable or preventable using compounds and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated or prevented include those related to platelet aggregation, the retinal arterioles, the glomerular arterioles, the vasa nervorum, cardiac arterioles, and associated capillary beds of the eye, the kidney, the heart, and the central and peripheral nervous systems. The a nicotinoyl riboside or derivative compound that increases the level of intracellular NAD+ may also be used for increasing HDL levels in plasma of an individual.

Yet other disorders that may be treated with a nicotinoyl riboside or derivative compound that increases the level of intracellular NAD+ include restenosis, e.g., following coronary intervention, and disorders relating to an abnormal level of high density and low density cholesterol.

In one embodiment, a nicotinoyl riboside or derivative compound that increases the level of intracellular NAD+ may be administered as part of a combination therapeutic with another cardiovascular agent including, for example, an antiarrhythmic agent, an antihypertensive agent, a calcium channel blocker, a cardioplegic solution, a cardiotonic agent, a fibrinolytic agent, a sclerosing solution, a vasoconstrictor agent, a vasodilator agent, a nitric oxide donor, a potassium channel blocker, a sodium channel blocker, statins, or a natriuretic agent.

In one embodiment, a nicotinoyl riboside or derivative compound that increases the level of intracellular NAD+ may be administered as part of a combination therapeutic with an anti-arrhythmia agent. Anti-arrhythmia agents are often organized into four main groups according to their mechanism of action: type I, sodium channel blockade; type II, beta-adrenergic blockade; type III, repolarization prolongation; and type IV, calcium channel blockade. Type I anti-arrhythmic agents include lidocaine, moricizine, mexiletine, tocainide, procainamide, encainide, flecanide, tocainide, phenytoin, propafenone, quinidine, disopyramide, and flecainide. Type II anti-arrhythmic agents include propranolol and esmolol. Type III includes agents that act by prolonging the duration of the action potential, such as amiodarone, artilide, bretylium, clofilium, isobutilide, sotalol, azimilide, dofetilide, dronedarone, ersentilide, ibutilide, tedisamil, and trecetilide. Type IV anti-arrhythmic agents include verapamil, diltaizem, digitalis, adenosine, nickel chloride, and magnesium ions.

In another embodiment, a nicotinoyl riboside or derivative compound that increases the level of intracellular NAD+ may be administered as part of a combination therapeutic with another cardiovascular agent. Examples of cardiovascular agents include vasodilators, for example, hydralazine; angiotensin converting enzyme inhibitors, for example, captopril; anti-anginal agents, for example, isosorbide nitrate, glyceryl trinitrate and pentaerythritol tetranitrate; anti-arrhythmic agents, for example, quinidine, procainaltide and lignocaine; cardioglycosides, for example, digoxin and digitoxin; calcium antagonists, for example, verapamil and nifedipine; diuretics, such as thiazides and related compounds, for example, bendrofluazide, chlorothiazide, chlorothalidone, hydrochlorothiazide and other diuretics, for example, fursemide and triamterene, and sedatives, for example, nitrazepam, flurazepam and diazepam.

Other exemplary cardiovascular agents include, for example, a cyclooxygenase inhibitor such as aspirin or indomethacin, a platelet aggregation inhibitor such as clopidogrel, ticlopidene or aspirin, fibrinogen antagonists or a diuretic such as chlorothiazide, hydrochlorothiazide, flumethiazide, hydroflumethiazide, bendroflumethiazide, methylchlorthiazide, trichloromethiazide, polythiazide or benzthiazide as well as ethacrynic acid tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, angiotensin II antagonists such as losartan, irbesartan or valsartan, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or animal salivary gland plasminogen activators, calcium channel blocking agents such as verapamil, nifedipine or diltiazem, thromboxane receptor antagonists such as ifetroban, prostacyclin mimetics, or phosphodiesterase inhibitors. Such combination products if formulated as a fixed dose employ the compounds of this invention within the dose range described above and the other pharmaceutically active agent within its approved dose range.

Yet other exemplary cardiovascular agents include, for example, vasodilators, e.g., bencyclane, cinnarizine, citicoline, cyclandelate, cyclonicate, ebumamonine, phenoxyezyl, flunarizine, ibudilast, ifenprodil, lomerizine, naphlole, nikamate, nosergoline, nimodipine, papaverine, pentifylline, nofedoline, vincamin, vinpocetine, vichizyl, pentoxifylline, prostacyclin derivatives (such as prostaglandin E1 and prostaglandin I2), an endothelin receptor blocking drug (such as bosentan), diltiazem, nicorandil, and nitroglycerin. Examples of the cerebral protecting drug include radical scavengers (such as edaravone, vitamin E, and vitamin C), glutamate antagonists, AMPA antagonists, kainate antagonists, NMDA antagonists, GABA agonists, growth factors, opioid antagonists, phosphatidylcholine precursors, serotonin agonists, $Na^+/Ca^{2+}$ channel inhibitory drugs, and $K^+$ channel opening drugs. Examples of the brain metabolic stimulants include amantadine, tiapride, and gamma-aminobutyric acid. Examples of the anticoagulant include heparins (such as heparin sodium, heparin potassium, dalteparin sodium, dalteparin calcium, heparin calcium, parnaparin sodium, reviparin sodium, and danaparoid sodium), warfarin, enoxaparin, argatroban, batroxobin, and sodium citrate. Examples of the antiplatelet drug include ticlopidine hydrochloride, dipyridamole, cilostazol, ethyl icosapentate, sarpogrelate hydrochloride, dilazep hydrochloride, trapidil, a nonsteroidal antiinflammatory agent (such as aspirin), beraprostsodium, iloprost, and indobufene. Examples of the thrombolytic drug include urokinase, tissue-type plasminogen activators (such as alteplase, tisokinase, nateplase, pamiteplase, monteplase, and rateplase), and nasaruplase. Examples of the antihypertensive drug include angiotensin converting enzyme inhibitors (such as captopril, alacepril, lisinopril, imidapril, quinapril, temocapril, delapril, benazepril, cilazapril, trandolapril, enalapril, ceronapril, fosinopril, imadapril, mobertpril, perindopril, ramipril, spirapril, and randolapril), angiotensin II antagonists (such as losartan, candesartan, valsartan, eprosartan, and irbesartan), calcium channel blocking drugs (such as aranidipine, efonidipine, nicardipine, bamidipine, benidipine, manidipine, cilnidipine, nisoldipine, nitrendipine, nifedipine, nilvadipine, felodipine, amlodipine, diltiazem, bepridil, clentiazem, phendilin, galopamil, mibefradil, prenylamine, semotiadil, terodiline, verapamil, cilnidipine, elgodipine, isradipine, lacidipine, lercanidipine, nimodipine, cinnarizine, flunarizine, lidoflazine, lomerizine, bencyclane, etafenone, and perhexiline), .beta.-adrenaline receptor blocking drugs (propranolol, pindolol, indenolol, carteolol, bunitrolol, atenolol, acebutolol, metoprolol, timolol, nipradilol, penbutolol, nadolol, tilisolol, carvedilol, bisoprolol, betaxolol, celiprolol, bopindolol, bevantolol, labetalol, alprenolol, amosulalol, arotinolol, befunolol, bucumolol, bufetolol, buferalol, buprandolol, butylidine, butofilolol, carazolol, cetamolol, cloranolol, dilevalol, epanolol, levobunolol, mepindolol, metipranolol, moprolol, nadoxolol, nevibolol, oxprenolol, practol, pronetalol, sotalol, sufinalol, talindolol, tertalol, toliprolol, xybenolol, and esmolol), .alpha.-receptor blocking drugs (such as amosulalol, prazosin, terazosin, doxazosin, bunazosin, urapidil, phentolamine, arotinolol, dapiprazole, fenspiride, indoramin, labetalol, naftopidil, nicergoline, tamsulosin, tolazoline, trimazosin, and yohimbine), sympathetic nerve inhibitors (such as clonidine, guanfacine, guanabenz, methyldopa, and reserpine), hydralazine, todralazine, budralazine, and cadralazine. Examples of the antianginal drug include nitrate drugs (such as amyl nitrite, nitroglycerin, and isosorbide), .beta.-adrenaline receptor blocking drugs (such as propranolol, pindolol, indenolol, carteolol, bunitrolol, atenolol, acebutolol, metoprolol, timolol, nipradilol, penbutolol, nadolol, tilisolol, carvedilol, bisoprolol, betaxolol, celiprolol, bopindolol, bevantolol, labetalol, alprenolol, amosulalol, arotinolol, befunolol, bucumolol, bufetolol, buferalol, buprandolol, butylidine, butofilolol, carazolol, cetamolol, cloranolol, dilevalol, epanolol, levobunolol, mepindolol, metipranolol, moprolol, nadoxolol, nevibolol, oxprenolol, practol, pronetalol, sotalol, sufinalol, talindolol, tertalol, toliprolol, andxybenolol), calcium channel blocking drugs (such as aranidipine, efonidipine, nicardipine, bamidipine, benidipine, manidipine, cilnidipine, nisoldipine, nitrendipine, nifedipine, nilvadipine, felodipine, amlodipine, diltiazem, bepridil, clentiazem, phendiline, galopamil, mibefradil, prenylamine, semotiadil, terodiline, verapamil, cilnidipine, elgodipine, isradipine, lacidipine, lercanidipine, nimodipine, cinnarizine, flunarizine, lidoflazine, lomerizine, bencyclane, etafenone, and perhexiline) trimetazidine, dipyridamole, etafenone, dilazep, trapidil, nicorandil, enoxaparin, and aspirin. Examples of the diuretic include thiazide diuretics (such as hydrochlorothiazide, methyclothiazide, trichlormethiazide, benzylhydrochlorothiazide, and penflutizide), loop diuretics (such as furosemide, etacrynic acid, bumetanide, piretanide, azosemide, and torasemide), $K^+$ sparing diuretics (spironolactone, triamterene, and potassium canrenoate), osmotic diuretics (such as isosorbide, D-mannitol, and glycerin), nonthiazide diuretics (such as meticrane, tripamide, chlorthalidone, and mefruside), and acetazolamide. Examples of the cardiotonic include digitalis formulations (such as digitoxin, digoxin, methyldigoxin, deslanoside, vesnarinone, lanatoside C, and proscillaridin), xanthine formulations (such as aminophylline, choline theophylline, diprophylline, and proxyphylline), catecholamine formulations (such as dopamine, dobutamine, and docarpamine), PDE III inhibitors (such as amrinone, olprinone, and milrinone), denopamine, ubidecarenone, pimobendan, levosimendan, aminoethylsulfonic acid, vesnarinone, carperitide, and colforsin daropate. Examples of the antiarrhythmic drug include ajmaline, pirmenol, procainamide, cibenzoline, disopyramide, quinidine, aprindine, mexiletine, lidocaine, phenyloin, pilsicainide, propafenone, flecainide, atenolol, acebutolol, sotalol, propranolol, metoprolol, pindolol, amiodarone, nifekalant, diltiazem, bepridil, and verapamil. Examples of the antihyperlipidemic drug include atorvastatin, simvastatin, pravastatin sodium, fluvastatin sodium, clinofibrate, clofibrate, simfibrate, fenofibrate, bezafibrate, colestimide, and colestyramine. Examples of the immunosuppressant include azathioprine, mizoribine, cyclosporine, tacrolimus, gusperimus, and methotrexate.

Cell Death/Cancer

Tiazofurin and benzamide riboside, analogs of NAR, have been used clinically as anticancer agents, since in vivo they could be metabolized to form NAD+ analogs, which inhibit IMP dehydrogenase, the rate-limiting enzyme for guanine nucleotide biosynthesis. Treatment of cultured cells has shown that tiazofurin reduces cancer cells by induction of apoptosis.

A nicotinoyl riboside or derivative compound that increases the level of intracellular NAD+ may be administered to subjects who have recently received or are likely to receive a dose of radiation or toxin. In one embodiment, the dose of radiation or toxin is received as part of a work-related or medical procedure, e.g., working in a nuclear power plant, flying an airplane, an X-ray, CAT scan, or the administration of a radioactive dye for medical imaging; in such an embodiment, the compound is administered as a prophylactic measure. In another embodiment, the radiation or toxin exposure is received unintentionally, e.g., as a result of an industrial accident, habitation in a location of natural radiation, terrorist act, or act of war involving radioactive or toxic material. In such a case, the compound is preferably administered as soon as possible after the exposure to inhibit apoptosis and the subsequent development of acute radiation syndrome.

A nicotinoyl riboside or derivative compound may also be used for treating and/or preventing cancer. In certain embodiments, a nicotinoyl riboside or derivative compound that increases the level of intracellular NAD+ may be used for treating and/or preventing cancer. Calorie restriction has been linked to a reduction in the incidence of age-related disorders including cancer A nicotinoyl riboside or derivative compound may also be used to reduce the adverse effects of drugs that are used to treat and/or prevent cancer. In certain embodiments, a nicotinoyl riboside or derivative compound that increases the level of intracellular NAD+ may be used to reduce the adverse effects of drugs that are used to treat and/or prevent cancer. Calorie restriction has been linked to a reduction in the incidence of age-related disorders including cancer In other embodiments, a nicotinoyl riboside or derivative compound that decrease the level of intracellular NAD+ may be used for treating or preventing cancer. For example, inhibitory compounds may be used to stimulate acetylation of substrates such as p53 and thereby increase apoptosis, as well as to reduce the lifespan of cells and organisms, render them more sensitive to stress, and/or increase the radiosensitivity and/or chemosensitivity of a cell or organism. Thus, inhibitory compounds may be used, e.g., for treating cancer. Exemplary are those of the brain and kidney; hormone-dependent cancers including breast, prostate, testicular, and ovarian cancers; lymphomas, and leukemias. In cancers associated with solid tumors, a modulating compound may be administered directly into the tumor. Cancer of blood cells, e.g., leukemia, can be treated by administering a modulating compound into the blood stream or into the bone marrow. Benign cell growth can also be treated, e.g., warts. Other diseases that can be treated include autoimmune diseases, e.g., systemic lupus erythematosus, scleroderma, and arthritis, in which autoimmune cells should be removed. Viral infections such as herpes, HIV, adenovirus, and HTLV-1 associated malignant and benign disorders can also be treated. Alternatively, cells can be obtained from a subject, treated ex vivo to remove certain undesirable cells, e.g., cancer cells, and administered back to the same or a different subject.

Chemotherapeutic agents that may be coadministered with modulating compounds described herein as having anti-cancer activity (e.g., compounds that induce apoptosis, compounds that reduce lifespan or compounds that render cells sensitive to stress) include: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouraci I, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine. These chemotherapeutic agents may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes—dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, COX-2 inhibitors, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors, epidermal growth factor (EGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; chromatin disruptors.

These chemotherapeutic agents may be used by themselves with a nicotinoyl riboside or derivative compound described herein as inducing cell death or reducing lifespan or increasing sensitivity to stress and/or in combination with other chemotherapeutics agents. Exemplary combinatorial therapies for the treatment of cancer. Name Therapeutic agents ABV Doxorubicin, Bleomycin, Vinblastine ABVD Doxorubicin, Bleomycin, Vinblastine, Dacarbazine AC (Breast) Doxorubicin, Cyclophosphamide AC (Sarcoma) Doxorubicin, Cisplatin AC (Neuro-Cyclophosphamide, Doxorubicin blastoma) ACE Cyclophosphamide, Doxorubicin, Etoposide ACe Cyclophosphamide, Doxorubicin AD Doxorubicin, Dacarbazine AP Doxorubicin, Cisplatin ARAC-DNR Cytarabine, Daunorubicin B-CAVe Bleomycin, Lomustine, Doxorubicin, Vinblastine BCVPP Carmustine, Cyclophosphamide, Vinblastine, Procarbazine, Prednisone BEACOPP Bleomycin, Etoposide, Doxorubicin, Cyclophosphamide, Vincristine, Procarbazine, Prednisone, Filgrastim BEP Bleomycin, Etoposide, Cisplatin BIP Bleomycin, Cisplatin, Ifosfamide, Mesna BOMP Bleomycin, Vincristine, Cisplatin, Mitomycin CA Cytarabine, Asparaginase CABO Cisplatin, Methotrexate, Bleomycin, Vincristine CAF Cyclophosphamide, Doxorubicin, Fluorouracil CAL-G Cyclophosphamide, Daunorubicin, Vincristine, Prednisone, Asparaginase CAMP Cyclophosphamide, Doxorubicin, Methotrexate, Procarbazine CAP Cyclophosphamide, Doxorubicin, Cisplatin CaT Carboplatin, Paclitaxel CAV Cyclophosphamide, Doxorubicin, Vincristine CAVE ADD CAV and Etoposide CA-VP16 Cyclophosphamide, Doxorubicin, Etoposide CC Cyclophosphamide, Carboplatin CDDPNP-16 Cisplatin, Etoposide CEF Cyclophosphamide, Epirubicin, Fluorouracil CEPP(B) Cyclophosphamide, Etoposide, Prednisone, with or without/Bleomycin CEV Cyclophosphamide, Etoposide, Vincristine CF Cisplatin, Fluorouracil or Carboplatin Fluorouracil CHAP Cyclophosphamide or Cyclophosphamide, Altretamine, Doxorubicin, Cisplatin ChlVPP Chlorambucil, Vinblastine, Procarbazine, Prednisone CHOP Cyclophosphamide, Doxorubicin, Vincristine, Prednisone CHOP-BLEO Add Bleomycin to CHOP CISCA Cyclophosphamide, Doxorubicin, Cisplatin CLD-BOMP Bleomycin, Cisplatin, Vincristine, Mitomycin CMF Methotrexate, Fluorouracil, Cyclophosphamide CMFP Cyclophosphamide, Methotrexate, Fluorouracil, Prednisone CMFVP Cyclophosphamide, Methotrexate, Fluorouracil, Vincristine, Prednisone CMV Cisplatin, Methotrexate, Vinblastine CNF Cyclophosphamide, Mitoxantrone, Fluorouracil CNOP Cyclophosphamide, Mitoxantrone, Vincristine, Prednisone COB Cisplatin, Vincristine, Bleomycin CODE Cisplatin, Vincristine, Doxorubicin, Etoposide COMLA Cyclophosphamide, Vincristine, Methotrexate, Leucovorin, Cytarabine COMP Cyclophosphamide, Vincristine, Methotrexate, Prednisone Cooper Cyclophosphamide, Methotrexate, Fluorouracil, Regimen Vincristine, Prednisone COP Cyclophosphamide, Vincristine, Prednisone COPE Cyclophosphamide, Vincristine, Cisplatin, Etoposide COPP Cyclophosphamide, Vincristine, Procarbazine, Prednisone CP (Chronic Chlorambucil, Prednisone lymphocytic leukemia) CP (Ovarian Cyclophosphamide, Cisplatin Cancer) CT Cisplatin, Paclitaxel CVD Cisplatin, Vinblastine, Dacarbazine CVI Carboplatin, Etoposide, Ifosfamide, Mesna CVP Cyclophosphamide, Vincristine, Prednisome CVPP Lomustine, Procarbazine, Prednisone CYVADIC Cyclophosphamide, Vincristine, Doxorubicin, Dacarbazine DA Daunorubicin, Cytarabine DAT Daunorubicin, Cytarabine, Thioguanine DAV Daunorubicin, Cytarabine, Etoposide DCT Daunorubicin, Cytarabine, Thioguanine DHAP Cisplatin, Cytarabine, Dexamethasone DI Doxorubicin, Ifosfamide DTIC/Dacarbazine, Tamoxifen Tamoxifen DVP Daunorubicin, Vincristine, Prednisone EAP Etoposide, Doxorubicin, Cisplatin EC Etoposide, Carboplatin EFP Etoposie, Fluorouracil, Cisplatin ELF Etoposide, Leucovorin, Fluorouracil EMA 86 Mitoxantrone, Etoposide, Cytarabine EP Etoposide, Cisplatin EVA Etoposide, Vinblastine FAC Fluorouracil, Doxorubicin, Cyclophosphamide FAM Fluorouracil, Doxorubicin, Mitomycin FAMTX Methotrexate, Leucovorin, Doxorubicin FAP Fluorouracil, Doxorubicin, Cisplatin F-CL Fluorouracil, Leucovorin FEC Fluorouracil, Cyclophosphamide, Epirubicin FED Fluorouracil, Etoposide, Cisplatin FL Flutamide, Leuprolide FZ Flutamide, Goserelin acetate implant HDMTX Methotrexate, Leucovorin Hexa-CAF Altretamine, Cyclophosphamide, Methotrexate, Fluorouracil ICE-T Ifosfamide, Carboplatin, Etoposide, Paclitaxel, Mesna IDMTX/6-MP Methotrexate, Mercaptopurine, Leucovorin IE Ifosfamide, Etoposie, Mesna IfoVP Ifosfamide, Etoposide, Mesna IPA Ifosfamide, Cisplatin, Doxorubicin M-2 Vincristine, Carmustine, Cyclophosphamide, Prednisone, Melphalan MAC-III Methotrexate, Leucovorin, Dactinomycin, Cyclophosphamide MACC Methotrexate, Doxorubicin, Cyclophosphamide, Lomustine MACOP-B Methotrexate, Leucovorin, Doxorubicin, Cyclophosphamide, Vincristine, Bleomycin, Prednisone MAID Mesna, Doxorubicin, Ifosfamide, Dacarbazine m-BACOD Bleomycin, Doxorubicin, Cyclophosphamide, Vincristine, Dexamethasone, Methotrexate, Leucovorin MBC Methotrexate, Bleomycin, Cisplatin MC Mitoxantrone, Cytarabine MF Methotrexate, Fluorouracil, Leucovorin MICE Ifosfamide, Carboplatin, Etoposide, Mesna MINE Mesna, Ifosfamide, Mitoxantrone, Etoposide mini-BEAM Carmustine, Etoposide, Cytarabine, Melphalan MOBP Bleomycin, Vincristine, Cisplatin, Mitomycin MOP Mechlorethamine, Vincristine, Procarbazine MOPP Mechlorethamine, Vincristine, Procarbazine, Prednisone MOPP/ABV Mechlorethamine, Vincristine, Procarbazine, Prednisone, Doxorubicin, Bleomycin, Vinblastine MP Melphalan, Prednisone (multiple myeloma) MP (prostate Mitoxantrone, Prednisone cancer) MTX/6-MO Methotrexate, Mercaptopurine MTX/6-MPNP Methotrexate, Mercaptopurine, Vincristine, Prednisone MTX-CDDPAdr Methotrexate, Leucovorin, Cisplatin, Doxorubicin MV (breast Mitomycin, Vinblastine cancer) MV (acute Mitoxantrone, Etoposide myelocytic leukemia) M-VAC Vinblastine, Doxorubicin, Cisplatin Methotrexate MVP Vinblastine, Cisplatin Mitomycin MVPP Mechlorethamine, Vinblastine, Procarbazine, Prednisone NFL Mitoxantrone, Fluorouracil, Leucovorin NOVP Mitoxantrone, Vinblastine, Vincristine OPA Vincristine, Prednisone, Doxorubicin OPPA Add Procarbazine to OPA. PAC Cisplatin, Doxorubicin PAC-I Cisplatin, Doxorubicin, Cyclophosphamide PA-CI Cisplatin, Doxorubicin PC Paclitaxel, Carboplatin or Paclitaxel, Cisplatin PCV Lomustine, Procarbazine, Vincristine PE Paclitaxel, Estramustine PFL Cisplatin, Fluorouracil, Leucovorin POC Prednisone, Vincristine, Lomustine ProMACE Prednisone, Methotrexate, Leucovorin, Doxorubicin, Cyclophosphamide, Etoposide ProMACE/Prednisone, Doxorubicin, Cyclophosphamide, cytaBOM Etoposide, Cytarabine, Bleomycin, Vincristine, Methotrexate, Leucovorin, Cotrimoxazole PRoMACE/Prednisone, Doxorubicin, Cyclophosphamide, MOPP Etoposide, Mechlorethamine, Vincristine, Procarbazine, Methotrexate, Leucovorin PtNM Cisplatin, Teniposide PVA Prednisone, Vincristine, Asparaginase PVB Cisplatin, Vinblastine, Bleomycin PVDA Prednisone, Vincristine, Daunorubicin, Asparaginase SMF Streptozocin, Mitomycin, Fluorouracil TAD Mechlorethamine, Doxorubicin, Vinblastine, Vincristine, Bleomycin, Etoposide, Prednisone TCF Paclitaxel, Cisplatin, Fluorouracil TIP Paclitaxel, Ifosfamide, Mesna, Cisplatin TTT Methotrexate, Cytarabine, Hydrocortisone Topo/CTX Cyclophosphamide, Topotecan, Mesna VAB-6 Cyclophosphamide, Dactinomycin, Vinblastine, Cisplatin, Bleomycin VAC Vincristine, Dactinomycin, Cyclophosphamide VACAdr Vincristine, Cyclophosphamide, Doxorubicin, Dactinomycin, Vincristine VAD Vincristine, Doxorubicin, Dexamethasone VATH Vinblastine, Doxorubicin, Thiotepa, Flouxymesterone VBAP Vincristine, Carmustine, Doxorubicin, Prednisone VBCMP Vincristine, Carmustine, Melphalan, Cyclophosphamide, Prednisone VC Vinorelbine, Cisplatin VCAP Vincristine, Cyclophosphamide, Doxorubicin, Prednisone VD Vinorelbine, Doxorubicin VelP Vinblastine, Cisplatin, Ifosfamide, Mesna VIP Etoposide, Cisplatin, Ifosfamide, Mesna VM Mitomycin, Vinblastine VMCP Vincristine, Melphalan, Cyclophosphamide, Prednisone VP Etoposide, Cisplatin V-TAD Etoposide, Thioguanine, Daunorubicin, Cytarabine 5+2 Cytarabine, Daunorubicin, Mitoxantrone 7+3 Cytarabine with/, Daunorubicin or Idarubicin or Mitoxantrone "8 in 1" Methylprednisolone, Vincristine, Lomustine, Procarbazine, Hydroxyurea, Cisplatin, Cytarabine, Dacarbazine.

In addition to conventional chemotherapeutics, the a nicotinoyl riboside or derivative compound described herein as capable of inducing cell death or reducing lifespan can also be used with antisense RNA, RNAi or other polynucleotides to inhibit the expression of the cellular components that contribute to unwanted cellular proliferation that are targets of conventional chemotherapy. Such targets are, merely to illustrate, growth factors, growth factor receptors, cell cycle regulatory proteins, transcription factors, or signal transduction kinases.

Chemical Synthesis of Nicotinoyl Ribosides

Due to its biological significance, a number of chemical approaches have been used to prepare nicotinamide riboside (NAR). See Franchetti et al., Bioorganic & Medicinal Chemistry Letters 14, 4655-4568 (2004) and Tanimori et al., Bioorganic & Medicinal Chemistry Letters 12, 1135-1137 (2002) both hereby incorporated by reference. However, there is still no systematical way to synthesize NAR analogs. One embodiment of the invention relates to an efficient method to stereoselectively synthesize β-NAR and its various derivatives in one pot with high yield. Compared to the previous methods, this stereoselective method is more efficient and gives more possibilities to form various NAD+ analogs with a similar procedure.

The synthesis of nicotinoyl riboside compounds was initiated with the preparation of a preferred intermediate, ethyl 1-[3,4-diacetyloxy-5-(acetyloxymethyl)oxolan-2-yl]-pyridine-3-carboxylate. Nicotinic acid riboside O-alkyl derivatives were prepared from there. Refluxing of the protected sugar, 1,2,3,5-tetra-O-acetyl-β-D-ribofuranose with ethyl nicotinate (1.2 equiv.) in methylene chloride under the catalysis of TMSOTf (1 equiv.) stereoselectively formed β-isomer in good yield (>90%). One of the advantages for this method is that there is no need to go through the silylation of nicotinamide. After evaporation of the solvent, ethyl 1-[3,4-diacetyloxy-5-(acetyloxymethyl)oxolan-2-yl]-pyridine-3-carboxylate could be used directly for the next step. The β-NAR and its derivatives are extremely water-soluble. Extraction of ethyl acetate from water layer could get rid of most non-polar side products and give 95% of pure products according to TLC. Ethyl 1-[3,4-diacetyloxy-5-(acetyloxymethyl)oxolan-2-yl]-pyridine-3-carboxylate was also treated with NaOCH$_3$/MeOH at −20° C. to form O-methyl nicotinate riboside. Other O-alkyl nicotinate ribosides were prepared similarly. O-Alkyl nicotinate ribosides can be hydrolyzed with esterase (from porcine liver, sigma) at pH=7.0 to afford clean nicotinic acid riboside. Reverse HPLC was used to detect and purify products.

Thermodynamic study showed the reaction of ethyl 1-[3,4-diacetyloxy-5-(acetyloxymethyl)oxolan-2-yl]-pyridine-3-carboxylate and NH$_3$/MeOH at −20° C. gave product methyl 1-[3,4-diacetyloxy-5-(acetyloxymethyl)oxolan-2-yl]-pyridine-3-carboxylate, instead of β-NAR. However, without worked up, the reaction could go further to finally form β-NAR after it was restored at 4° C. This could be explained thermodynamically. Since amide is thermodynamically more stable than ester, at higher temperature, the more stable β-NAR would be the primary product. However, the reaction with NaOCH$_3$ at lower temperature, −20° C., kinetically favors the formation of O-methyl nicotinate riboside.

Figure 5:
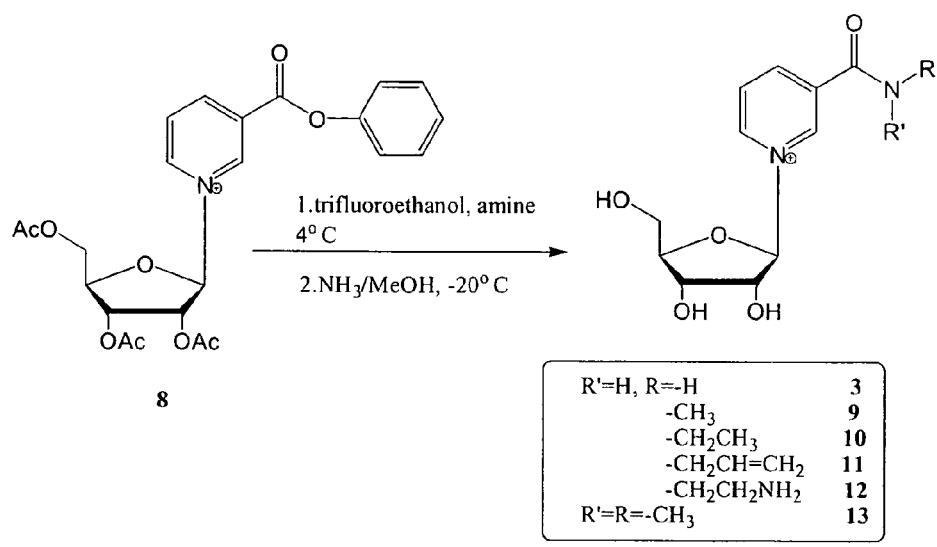
FIG. 5 illustrates the preparation of N-alkyl nicotinamide ribosides.
Figure 6:
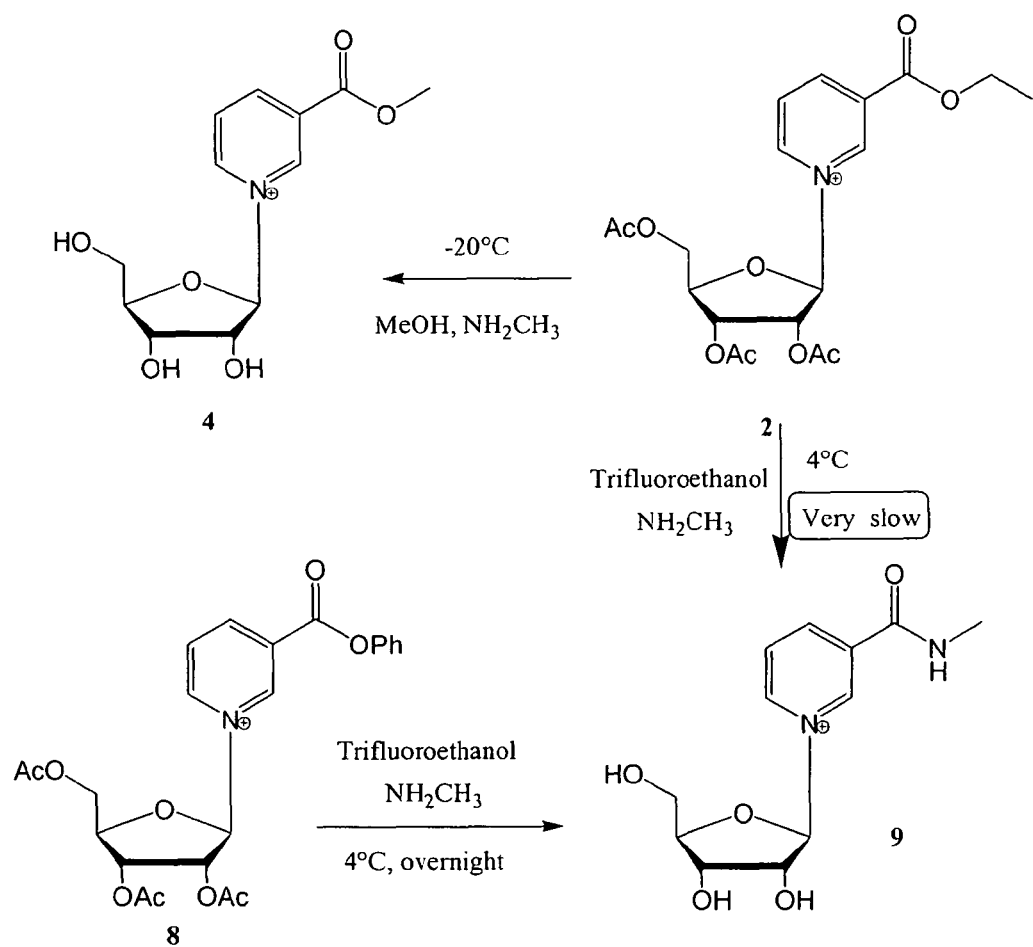
FIG. 6 illustrates kinetically (−20° C.) or thermodynamically (4° C.) controlled reactions of O-alkyl nicotinate ribosides with alkyl amines.

The preparation of N-alkyl β-NAR derivatives starts from, 2,3,5-tri-O-acetyl-β-phenyl nicotinate riboside (see FIG. 5) an activated phenyl ester. Incubation of nicotinic chloride with phenol in THF overnight at room temperature quantitatively produced pure phenyl nicotinate, which was then treated with 1,2,3,5-tetra-O-acetyl-β-D-ribofuranose in methylene chloride under the catalysis of TMSOTf to give 2,3,5-tri-O-acetyl-β-phenyl nicotinate riboside. 2,3,5-Tri-O-acetyl-β-phenyl nicotinate riboside could be transformed further to prepare multiple N-alkyl NR derivatives with addition of various primary or secondary amines. The ethyl ester intermediate was also considered to be used in building the N-alkyl NAR derivatives since in literature ester-amide exchange has been considered a versatile and simple way to make amides. However, our thermodynamic study (see FIG. 6) showed that the incubation of the ethyl ester intermediate with N-methyl amine in methanol at −20° C. formed the O-methyl nicotinate riboside as the product, instead of the expected N-methyl nicotinamide riboside. MALDI-MS of the product showed the molecular weight at 270 which is one mass more than the expected 269. The m/z peak at 138 rather than 137 was also detected which was due to the methyl nicotinate piece coming after the $C^{1'}$—$N^1$ bond of the methyl ester was broken. All the information suggests that a transesterification occurs rather than the ester-amide exchange. In the low temperature, both transesterification and ester-amide reactions were very slow so that the reaction selectivity was kinetically controlled. The transesterification was more kinetically favored than the ester-amide exchange because of the higher concentration of the solvent, methanol. Since amide is thermodynamically more stable than ester, we assume that the reaction selectivity at higher temperature would be thermodynamically controlled so as to form the more stable amide product. Therefore, the same reaction mixture was incubated at 4° C. However, after overnight, the riboside was totally decomposed, and N-methyl amine and free sugar were formed, which did not happened in the preparation of β-NAR with using NH$_3$/MeOH at all. Decomposition maybe due to the fact that N-alkyl amines are more basic/neutrophilic than free ammonia, which tend to attack the C-1' position of the riboside and cause to the breaking of the bond.

In order to avoid the decomposition, another reaction solvent, trifluoroethanol (TFE) has been tried. TFE has a pKa of 12.5, which makes it more acidic compared to solvent like methanol or ethanol. This acidity of the TFE decreases the neutrophilicity of N-alkyl amines, therefore helps stabilizing the $C^{1'}$—$N^1$ bond. The reaction of the ethyl ester was then performed in trifluoroethanol under 4° C. for days. It was found the acidity of trifluoroethanol also moderates the nucleophilicity/basicity of N-methyl amine so that the ester-amide exchange reaction takes weeks to complete. The ester-amide exchange from the phenol ester in trifluoroethanol at 4° C. could complete overnight. Interesting enough, we also found that 2'-, 3'- and 5'-O-acetyl groups on the sugar exhibit different deacetylation rates under the same basic condition. After the treatment with N-methyl amine at 4° C. overnight, MALDI-MS has shown the molecular weight of the isolated product as 311 instead of the expected 269. $^1$H-NMR also agreed that the 5'-O-acetyl group hasn't been taken off from the molecule. This selective deprotection method in fact brings up a convenient opportunity for a selective modification on the 5' position of the ribose. After 4N of $NH_3$/MeOH was added into the reaction mixture, the reaction was then complete after an overnight incubation at −20° C., and gave the expected deprotected product. All other N-alkyl nicotinamide riboside have also been prepared with the similar procedure.

Compositions for Administration

The compositions comprising the active compounds (nicotinamide riboside derivatives) include nutritional/dietary supplements and bulk-drug compositions useful in the manufacture of pharmaceutical compositions (e.g., impure or non-sterile compositions) and pharmaceutical compositions (i.e., compositions that are suitable for administration to a subject) that can be used in the preparation of unit dosage forms. Such compositions optionally comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of the active compound and another therapeutic or prophylactic agent, and a pharmaceutically acceptable carrier. These compositions may contain between 0.1-99% of the active ingredient In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents can be used. When administered to a subject, the pharmaceutically acceptable vehicles are preferably sterile. Water can be the vehicle when the active compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propyleneglycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155).

In a preferred embodiment, the active compound and optionally another therapeutic or prophylactic agent are formulated in accordance with routine procedures as pharmaceutical compositions adapted for intravenous administration to human beings. Typically, the active compound for intravenous administration are solutions in sterile isotonic aqueous buffer. Where necessary, the compositions can also include a solubilizing agent. Compositions for intravenous administration can optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the active compound is to be administered by infusion, it can be dispensed, for example, with an infusion bottle containing sterile pharmaceutical grade water or saline. Where the active compound is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for an orally administered of the active compound. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate can also be used. Oral compositions can include standard vehicles such as mannitol, lactose, starch, magnesium stearate, sodium saccharine, cellulose, magnesium carbonate, and the like. Such vehicles are preferably of pharmaceutical grade.

Further, the effect of the active compound can be delayed or prolonged by proper formulation. For example, a slowly soluble pellet of the active compound can be prepared and incorporated in a tablet or capsule. The technique can be improved by making pellets of several different dissolution rates and filling capsules with a mixture of the pellets. Tablets or capsules can be coated with a film that resists dissolution for a predictable period of time. Even the parenteral preparations can be made long-acting, by dissolving or suspending the compound in oily or emulsified vehicles which allow it to disperse only slowly in the serum.

Compositions for use in accordance with the present invention can be formulated in conventional manner using one or more physiologically acceptable carriers or excipients.

Thus, the compound and optionally another therapeutic or prophylactic agent and their physiologically acceptable salts and solvates can be formulated into pharmaceutical compositions for administration by inhalation or insufflation (either through the mouth or the nose) or oral, parenteral or mucosol (such as buccal, vaginal, rectal, sublingual) administration. In one embodiment, local or systemic parenteral administration is used.

For oral administration, the compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the compositions can take the form of tablets or lozenges formulated in conventional manner.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The compositions can be formulated for parenteral administration by injection, e.g., by bolus injection or continuous infusion. Formulations for injection can be presented in unit dosage form, e.g., in ampoules or in multi-dose containers, with an added preservative. The pharmaceutical compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The compositions can also be formulated in rectal compositions such as suppositories or retention enemas, e.g., containing conventional suppository bases such as cocoa butter or other glycerides.

In addition to the formulations described previously, the compositions can also be formulated as a depot preparation. Such long acting formulations can be administered by implantation (for example subcutaneously or intramuscularly) or by intramuscular injection. Thus, for example, the pharmaceutical compositions can be formulated with suitable polymeric or hydrophobic materials (for example as an emulsion in an acceptable oil) or ion exchange resins, or as sparingly soluble derivatives, for example, as a sparingly soluble salt.

In other embodiments of the invention, radiation therapy agents such as radioactive isotopes can be given orally as liquids in capsules or as a drink. Radioactive isotopes can also be formulated for intravenous injection. The skilled oncologist can determine the preferred formulation and route of administration.

The compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

In certain preferred embodiments, the pack or dispenser contains one or more unit dosage forms containing no more than the recommended dosage formulation as determined in the Physician's Desk Reference ($56^{th}$ ed. 2002, herein incorporated by reference in its entirety).

Methods of administering the active compound and optionally another therapeutic or prophylactic agent include, but are not limited to, parenteral administration (e.g., intradermal, intramuscular, intraperitoneal, intravenous and subcutaneous), epidural, and mucosal (e.g., intranasal, rectal, vaginal, sublingual, buccal or oral routes). In a specific embodiment, the active compound and optionally another prophylactic or therapeutic agents are administered intramuscularly, intravenously, or subcutaneously. The active compound and optionally another prophylactic or therapeutic agent can also be administered by infusion or bolus injection and can be administered together with other biologically active agents. Administration can be local or systemic. The active compound and optionally the prophylactic or therapeutic agent and their physiologically acceptable salts and solvates can also be administered by inhalation or insufflation (either through the mouth or the nose). In a preferred embodiment, local or systemic parenteral administration is used.

In specific embodiments, it can be desirable to administer the active compound locally to the area in need of treatment. This can be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers. In one embodiment, administration can be by direct injection at the site (or former site) of an atherosclerotic plaque tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the active compound can be formulated as a suppository, with traditional binders and vehicles such as triglycerides.

In another embodiment, the active compound can be delivered in a vesicle, in particular a liposome.

In yet another embodiment, the active compound can be delivered in a controlled release system. In one embodiment, a pump can be used. In another embodiment, polymeric materials can be used.

The amount of the active compound that is effective in the treatment or prevention of heart conditions can be determined by standard research techniques. For example, the dosage of the active compound which will be effective in the treatment or prevention of heart conditions can be determined by administering the active compound to an animal in a model such as, e.g., the animal models known to those skilled in the art. In addition, in vitro assays can optionally be employed to help identify optimal dosage ranges.

Selection of a particular effective dose can be determined (e.g., via clinical trials) by a skilled artisan based upon the consideration of several factors which will be known to one skilled in the art. Such factors include the disease to be treated or prevented, the symptoms involved, the subject's body mass, the subject's immune status and other factors known by the skilled artisan.

The precise dose to be employed in the formulation will also depend on the route of administration, and the seriousness of the disease-related wasting, and should be decided according to the judgment of the practitioner and each subject's circumstances. Effective doses can be extrapolated from dose-response curves derived from in vitro or animal model test systems.

The dose of the active compound to be administered to a subject, such as a human, is rather widely variable and can be subject to independent judgment. It is often practical to administer the daily dose of the active compound at various hours of the day. However, in any given case, the amount of the active compound administered will depend on such factors as the solubility of the active component, the formulation used, subject condition (such as weight), and/or the route of administration.

The general range of effective amounts of the active compound alone or in combination with another prophylactic or therapeutic agent(s) are from about 0.001 mg/day to about 1000 mg/day, more preferably from about 0.001 mg/day to 750 mg/day, more preferably from about 0.001 mg/day to 500 mg/day, more preferably from about 0.001 mg/day to 250 mg/day, more preferably from about 0.001 mg/day to 100 mg/day, more preferably from about 0.001 mg/day to 75 mg/day, more preferably from about 0.001 mg/day to 50 mg/day, more preferably from about 0.001 mg/day to 25 mg/day, more preferably from about 0.001 mg/day to 10 mg/day, more preferably from about 0.001 mg/day to 1 mg/day. Of course, it is often practical to administer the daily dose of compound in portions, at various hours of the day. However, in any given case, the amount of compound administered will depend on such factors as the solubility of the active component, the formulation used, subject condition (such as weight), and/or the route of administration.

A popular cancer drug is taxol. Typical dosage ranges of taxol include less than 10 mg to 100 mg or more. Particular doses of taxol include about 5 mg, 10 mg, 20 mg, 40 mg, 50 mg, 60 mg, 80 mg, 100 mg, 150 mg, 200 mg. Typically, these are daily dosages. Generally, higher dosages are less preferred because of potential gastric disturbances. Therapeutic dosages may range between 40 to 80 mg per day when tolerable by a subject.

The invention provides for any method of administrating lower doses of known agents (e.g., taxol) than previously thought to be useful for the prevention or treatment of cancer.

The invention provides a pharmaceutical pack or kit comprising one or more containers containing an active compound and optionally one or more other prophylactic or therapeutic agents useful for the prevention or treatment of cancer. The invention also provides a pharmaceutical pack or kit comprising one or more containers containing one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration; or instructions for the composition's use.

The present invention provides kits that can be used in the above methods. In one embodiment, a kit comprises the active compound, in one or more containers, and optionally one or more other prophylactic or therapeutic agents useful for the treatment of cancer, in one or more containers.

EXAMPLES

Example 1

Synthesis of 2',3',5'-Triacetyl ethyl nicotinate riboside (ethyl 1-[3,4-diacetyloxy-5-(acetyloxymethyl) oxolan-2-yl]-pyridine-3-carboxylate)

One equivalent of trimethylsilyl trifluoromethanesulfonate (TMSOTf) was slowly added into Ethyl nicotinate (0.9 mL, 6.6 moL) and 1,2,3,5-tetra-O-acetyl-β-D-ribofuranose (1.4 g, 4.4 mmol) in 50 mL anhydrous methylene chloride at room temperature. The mixture was then heated to reflux for 8 hour. TLC stained with $H_2SO_4$ in MeOH showed the disappearance of 1,2,3,5-tetra-O-acetyl-β-D-ribofuranose, and almost pure product. The product could be used directly for the next step after methylene chloride was evaporated.

Example 2

Synthesis of β-NAR (Nicotinamide Riboside)

2',3',5'-Triacetyl ethyl nicotinate riboside (180 mg, 0.44 mmol) was added into 4.7 mL of 4N $NH_3$/MeOH on ice. After mixed well, the reaction was stored at 4° C. overnight. After methanol was removed in vacuum, the residue was dissolved in water, and extracted with ethyl acetate three times to get rid of the non-polar impurity. The water layer was then concentrated and injected into reverse HPLC for purification (waters xTerra Prep RP 18® column, 2 mL/min, 20 mM ammonium acetate).

Example 3

O-alkyl β-nicotinate ribosides

2',3',5'-Triacetyl ethyl nicotinate riboside (25 mg, 0.61 μmol) was added into 0.9 mL of NaOMe/MeOH (255 mM) or NaOEt/EtOH (312 mM) on ice. After mixed well, the reaction was stored at −20° C. overnight. The reaction was quenched with addition of acetic acid to pH=7. After organic solvent was removed in vacuum, the residue was dissolved in water, and extracted with cyclohexane to get rid of the non-polar impurity. The water layer was then concentrated and injected into reverse HPLC for purification.

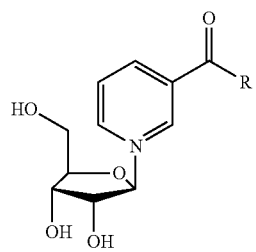

TABLE 1

| Entry (FIG. 1) | R | Temp. |
|---|---|---|
| 14 | —$OCH_3$ | −20° C. |
| 15 | —$OCH_2CH_3$ | −20° C. |
| 16 | —$OCH_2CH_2OH$ | −20° C. |

Example 4

N-alkyl β-nicotinamide ribosides

Nicotinic chloride (1.78 g, 10 mmoL) was added to phenol (1.29 g, 12 mmoL) in 10 mL of THF. Triethylamine (5 mL) and pyridine (5 mL) were then added to the mixture, which was then stirred at room temperature overnight. After THF was evaporated, the mixture was then washed with ethyl acetate in water for three times. The organic layer was then purified with silica column (Hexane:EtOAC=4:1) to give pure product. The riboside was prepared according to the procedure provided in Example 1. This phenol ester (25 mg, 0.61 μmol) was added to various amines (400 μM) in 0.9 mL of trifluoroethanol. After mixed well, the reaction was stored at 4° C. overnight. On the next day, 4N of $NH_3$/MeOH was added into the reaction mixture, and the reaction was stored at −20° C. overnight. After the reaction was quenched with addition of HCl to make pH<7, the organic solvent was removed in vacuum. The residue was dissolved in water and isolated with a Octadecyl-C18 disposable extraction.

TABLE 2

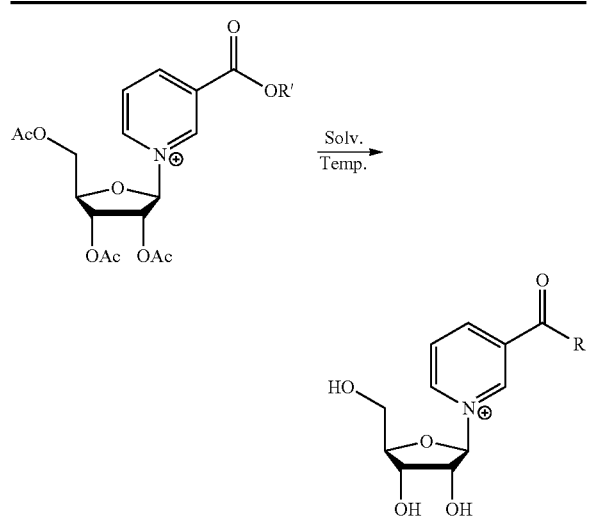

| Entry (FIG. 1) | Intermediate | Solvent Temp. | Product | Yield (%) |
|---|---|---|---|---|
| 3 | R' = $C_2H_5$ | MeOH 4° C. | R = $NH_2$ | 85 |
| 4 | R' = $C_2H_5$ | MeOH −20° C. | R = $OCH_3$ | 85 |
| 5 | R' = $C_2H_5$ | EtOH −20° C. | R = $OC_2H_5$ | 81 |
| 6 | R' = $C_2H_5$ | | R = OH | 80 |
| 9 | R' = $C_6H_5$ | TFE 4° C. | R = $NHCH_3$ | 80 |
| 10 | R' = $C_6H_5$ | TFE 4° C. | R = $NHC_2H_5$ | 80 |
| 11 | R' = $C_6H_5$ | TFE 4° C. | R = $NHCH_2CH=CH_2$ | 80 |
| 12 | R' = $C_6H_5$ | TFE 4° C. | R = $NHC_2H_4NH_2$ | 55 |
| 13 | R' = $C_6H_5$ | TFE 4° C. | R = $NH(CH_3)_2$ | 52 |

Example 5

Synthesis of β-Nicotinic acid riboside (1-[3,4-dihydroxy-5-(hydroxymethyl)oxolan-2-yl]pyridine-5-carboxylic acid)

Methyl 1-[3,4-diacetyloxy-5-(acetyloxymethyl)oxolan-2-yl]-pyridine-3-carboxylate was dissolved into phosphate buffer (150 mM, pH=7.0). 10 uL of esterase was added to the mixture, and mixed well. The reaction was run at 25° C. overnight. HPLC injection showed 98% pure product.

Example 6

Figure 3:
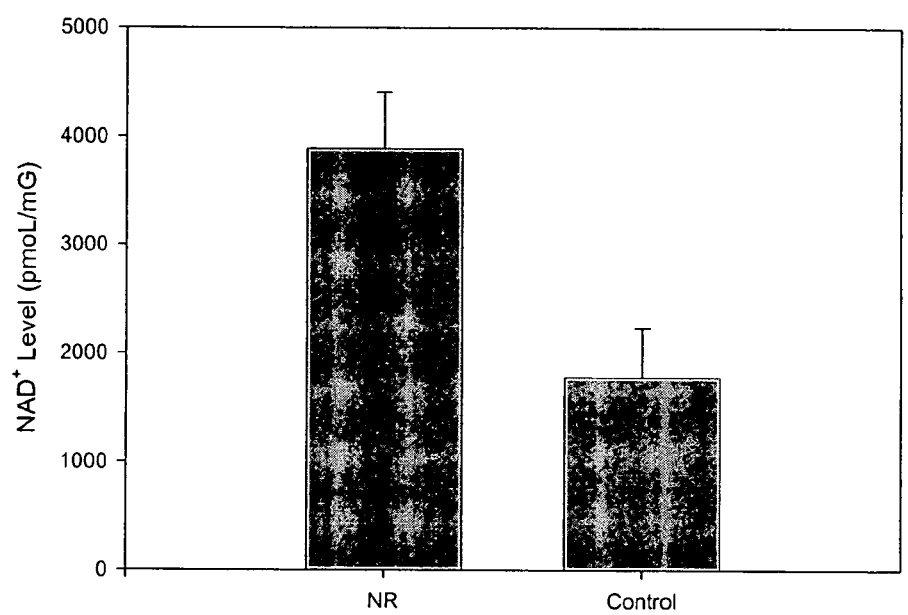
FIG. 3 shows data on the increase of intracellular levels of nicotinamide adenine dinucleotide (NAD+) when embryonic stem cells are exposed to a culture containing NAR as provided in example 6.

Increase of Cellular NAD+ Levels Grown on Nicotinamide Riboside (NAR) Enriched Medium Mouse embryonic stem cells were plated onto cell culture flasks (250 mL, 75 $cm^2$) and grown to 50% confluence in 48 hours after passage. At 48 hours 2 flasks were set aside as controls and 2 flasks were used to determine effect of NAR on NAD+ biosynthesis. Cells were treated with 1M $HClO_4$, and a specific amount of $^{18}$O-NAM (nicotinamide mononucleotide) and $^{18}$O-NAD+. Samples were fractionated by HPLC and the fractions containing NAM and NAD+ were analyzed by ESI-MS and MALDI-MS respectively. Peak ratio ($^{16}O/^{18}O$) was used to quantitate NAM and NAD+ amounts in each sample. It was found that NAR treated cells exhibit a higher concentration of NAD+ compared to the controls. According to our measurement, the NAD+ level in NAR treated cells is 3886.6 pmoL/mg cell protein and nucleic acid content, and the NAD+ in control cells is only 1782.2 pmoL/mg cell protein and nucleic acid content. Cell protein and nucleic acid content were measured separately (See FIG. 3).

Example 7

Effect of Nicotinamide Riboside (NAR) on mms Mediated Cell Death

Figure 2:
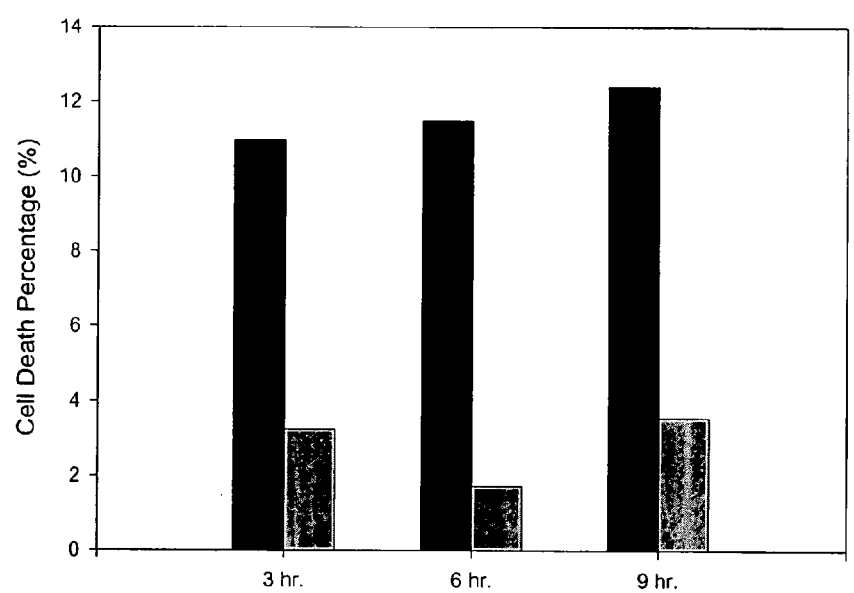
FIG. 2 shows data on the improvement of cell survival when grown on a media supplemented with nicotinamide riboside (NAR) as provided in example 7.

Mouse embryonic stem cells are passed into 7 flasks (250 mL, 75 $cm^2$) with 20 mL of media [For 500 mL: Dulbeccos modification of Eagles media 2 mM glutamine, 10% ES qualified Fetal Bovine Serum to 10%, Penicillin/streptomycin (5 mL 100×), Non-essential amino acids (5 mL 100×), Sodium pyruvate (5 mL 100×), 4 μL beta-mercapto-ethanol and leukemia inhibitory factor final conc. 1000 units/mL], named from #1 to #7. After 2 days incubation at 37° C. with 5% $CO_2$, NAR was added to flask #3, 5, 7 to make final concentration at 1 mM, and cells were incubated for another day. Mms (200 mM) was added to flask #2, 3, 4, 5, 6, 7 to make final concentration as 1 mM. Cell flask #1 is kept as a control, and used for passage. After 3 hrs incubation, fresh media was changed for flask #4, 5, 6, 7. And Cell #2, and 3 are harvested. After 6 hrs treatment of mms, Cell #4, 5 are harvested. And Cell #6, 7 are harvested at 9 hrs treatment of mms. The harvest cells (living ones) are counted for the percentage of death with trypan blue (See FIG. 2).

Example 8

Cell Survival

Figure 4:
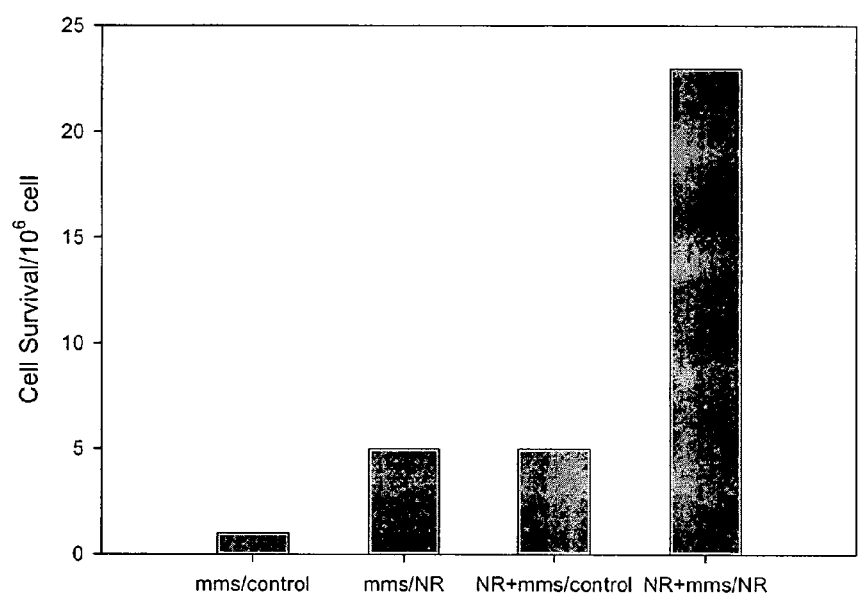
FIG. 4 shows data on effects of NAR on cell survival as provided in example 8.

Mouse embryonic stem cells are passed into 2 flasks (250 mL, 75 $cm^2$) with 20 mL of media, named #A and #B. After 2 days incubation at 37° C. with 5% $CO_2$, NAR was added to flask #A to make final concentration at 1 mM, and both cells were incubated for another day. Mms (200 mM) was added to both flask #A and #B to make final concentration as 1 mM. After 3 hrs incubation, each cell culture (with/without NR treated) is passed to two new flasks with/without 1 mM of NAR. After two days incubation, count the culture survival in each of these 4 new flasks: mms/control media, mms/NAR media; mms+NAR/control media; mms+NAR/NAR media. It was found after mms treatment, the cultured cells are seriously damaged and only have a very low survival after passage. However, compared to others, NAR treated cell culture provides the highest culture numbers. Cell counting by haemocytometry was used to determine survival versus cell number (See FIG. 4).

Example 9

Effects of Statins on Cell Viability and Mitigation of Toxicity by Nicotinamide Riboside Equal numbers of mouse embryonic stem cells are passed into two 6 well tissue culture plates (10 cm² each well) with 3 mL of media [For 500 mL: Dulbeccos modification of Eagles media 2 mM glutamine, 10% ES qualified Fetal Bovine Serum to 10%, Penicillin/streptomycin (5 mL 100×), Non-essential amino acids (5 mL 100×), Sodium pyruvate (5 mL 100×), 4 µL beta-mercapto-ethanol and leukemia inhibitory factor final conc. 1000 units/mL], named from #1 to #6. After 2 days incubation at 37° C. with 5% $CO_2$, different concentrations of lovastatin 0, 50, 250, 800, 2000 and 10000 nM was added to wells 1-6 on each plate respectively. The two plates were then renamed NR and no NR to represent treatment and lack of treatment with the compound nicotinamide riboside (NR). Each well in the NR plate was treated with 10 µL 150 mM NR to make a final concentration of NR in each well of 500 µM. At 2, 4 and 7 days cells were assayed by cell counting and by MTT assay after trypinizing cells to detach them from plates. At 2 and 4 days cells were reseeded from each individual well into new wells in new 6 well plates and treated immediately with the same concentration of NR and statin as the cells from the originating well. The seeded cells were identical in number of viable cells in each case as determined by cell counting an appropriate dilution of the cells trypsinized from each well.

Figure 8:
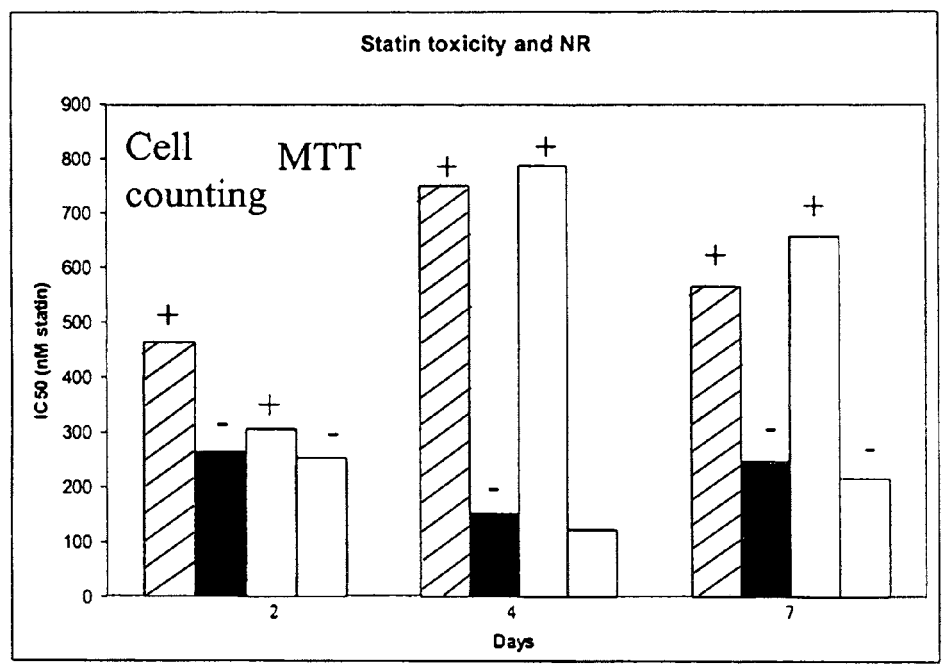
FIG. 8 demonstrates reduction of statin (lovastatin) toxicity for mouse embryonic stem cells treated with nicotinamide riboside (500 µM) for periods of 2, 4 and 7 days. Statin only treated controls are indicated by minus symbols. The bars represent the concentration of statin that leads to 50% decrease in cell number or MTT assay, which measures cell viability. The two far left columns in each day are measured by cell counting, the two far right columns are measured by MTT. As shown, NR treatment significantly reduces the toxicity of statin on cell viability as determined by an increase in the amount of statin required to kill cells.

The cell viability at each time point was plotted against statin concentration to determine the IC50 of the statin in the NR and the no NR plate where IC50 is defined as the concentration of statin that reduces cell viability by 50% under the experimental conditions. The statin typically reduces cell viability by 50% at a concentration between 130 nM-300 nM at each time point for cells not treated with NR (FIG. 8). In the presence of NR the IC50 of the statin increases moderately at 2 days treatment and two to three fold after 4 and 7 days treatment (FIG. 8). This shows that NR mitigates statin toxicity in a significant way with NR available in cell media.

The cell viability as measured by cell counting and MTT assay is significantly higher in the NR treated group versus no NR at virtually every statin concentration, resulting in a higher IC50 for statins in the presence of NR (566 nM, determined by cell counting; 656 nM determined by MTT assay) versus the absence of NR (248 nM, determined by cell counting; 216 nM determined by MTT assay). Notably at the highest statin concentration measured, 10 µM, significant percentages of viable cells remain in the NR treated group as measured by both cell counting and MTT assay, whereas the cell viability in the no NR group is almost completely non-viable. The data analysis used was analogous in the 2 and 4 day results shown graphically in FIG. 8.

Example 10

Evaluation of Different Nicotinate Riboside Derivatives as Bioavailable Forms of Niacin that Stimulate NAD+ Synthesis in Cells Hela cells were seeded on a 6-well plate at 37° C. with 5% $CO_2$ for 24 hrs. Synthesized compounds (NAR: Nicotinic acid riboside, O-ethyl-NR: ethyl-nicotinate riboside, Intermediate: TAENR, triacetyl-ethyl-nicotinate riboside, See FIG. 10) were added to the cells separately after 24 hours (no compound added for control). The cells were then incubated for another 24 hrs before harvest. Cells were trypsinized and an aliquot removed for counting. Cells were pelleted and then were dissolved into 100 uL of 7% perchloric acid, and 535.5 pmoL of $^{18}$O-NAD+ (95% isotopically enriched) was added to each sample. After mixing thoroughly, samples were pelleted and then neutralized with NaOH to make pH=7~8. Samples were then centrifuged for 3 minutes and the supernatant (100 uL) was injected onto a C-18 column (Hitachi HPLC L2130 pump L2450 diode array detector) and separated to isolate the peak containing NAD+. The elution was collected during the NAD+ peak and the solution frozen and lyophilized. The sample was assayed by MALDI-MS in positive ion detection mode to determine the NAD+ content (Table 3) by measuring the m/z=664 ($^{16}$O-NAD+ and 666 ($^{18}$O-NAD+) peaks.

Figure 9:
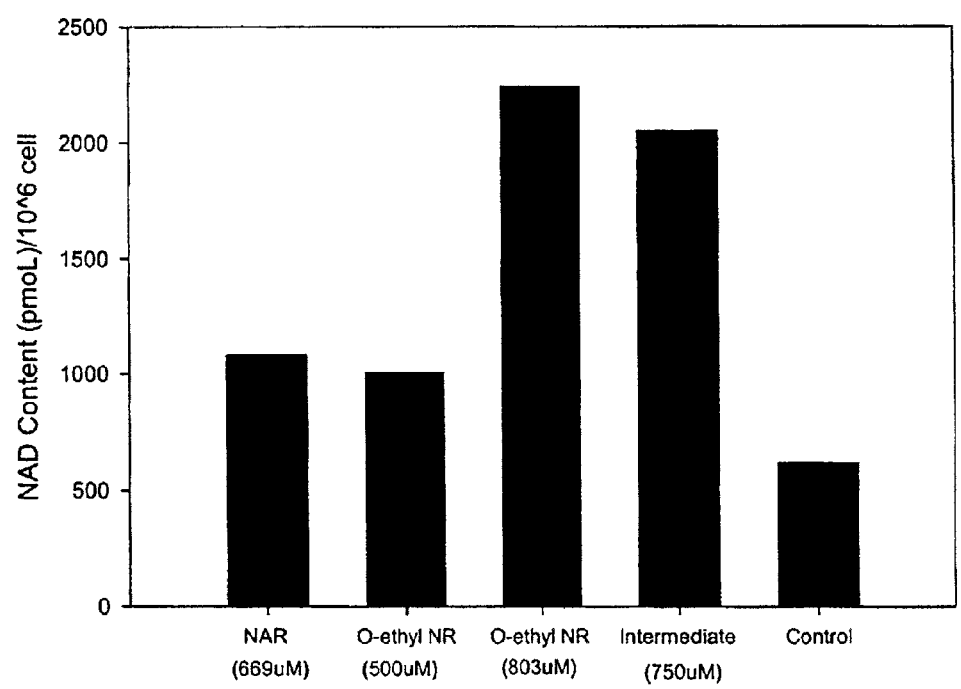
FIG. 9 shows a bar chart of NAD+ content (pmoL) in ES cells after treated with different compounds.

The experiment suggests that different forms of nicotinate ribosides are available as metabolizable sources of niacin and that these chemical forms of niacin of novel composition have the effect of substantially increasing NAD+ concentrations in cells as determined by a quantitative MS assay. Increases in NAD+ concentrations within cells can lead to clinical benefits. The minimal increase in NAD+ concentration in cells we observed was from 618 pmol per million cells (Table 3, and bar chart FIG. 9) in untreated cells to 1004 pmol per million cells in the case of treatment with 500 micromolar treatment of the compound O-ethyl nicotinate riboside. This represents a 62% increase over the control NAD+ content. Increasing the concentration of this compound to 800 micromolar led to an increase in NAD+ concentration of approximately three fold (Table 3). Similarly nicotinic acid riboside and the fully esterified compound tri-acetyl-ethylnicotinate riboside was able to increase NAD+ concentrations in cells by 60% and three fold respectively (Table 3). These data demonstrate that these derivatives are metabolized by cells and increase NAD+ concentrations in cells in a substantive manner (60-300%). These compounds increase intracellular NAD+.

TABLE 3

NAD+ content (pmoL) in ES cells after treated with different compounds

| Compounds | 664/666 | $^{16}$O-NAD+ (pmol) | $^{18}$O-NAD+ (pmol) | Cell number (*10^6) | [NAD+]/ 10^6 cell (pmoL) |
|---|---|---|---|---|---|
| NAR (669 uM) | 4.11 | 2201.2 | 535.5 | 2.04 | 1079 |
| O-ethyl NR (500 uM) | 2.02 | 1084.1 | 535.5 | 1.08 | 1004 |
| O-ethyl NR (803 uM) | 4.90 | 2622.7 | 535.5 | 1.17 | 2242 |
| TAENR (750 uM) | 8.28 | 4432.2 | 535.5 | 2.16 | 2052 |
| Control | 2.01 | 1075.5 | 535.5 | 1.74 | 618 |

NAR: Nicotinic acid riboside, O-ethyl-NR: ethyl-nicotinate riboside, TAENR, triacetyl-ethyl-nicotinate riboside Example 11

Reduction in Statin Toxicity

ES cells were growing on four 6-well plate at 37° C. with 5% $CO_2$ for 24 hrs. The cells were then treated with 0, 800 or 5000 nM lovastatin (final concentration) and also treated with one of 500 μM NAR, 1 mM OENR, 1 mM TAENR or no compound. After 48 hours cells media was removed and cells were harvested by trypsinizing. Cells were counted by haemocytometry and using propidium iodide staining to assess for viability. Cells were counted for no statin treatment and 800 nM and 5 μM statin treatment in each group. Cell death percentage was determined by the viable cells in each group divided by the cell numbers in the corresponding no statin treated group. Cell counts were similar in controls from each group (no statin) indicating low toxicity of the added nicotinate riboside compounds to the treated cells.

Figure 10:
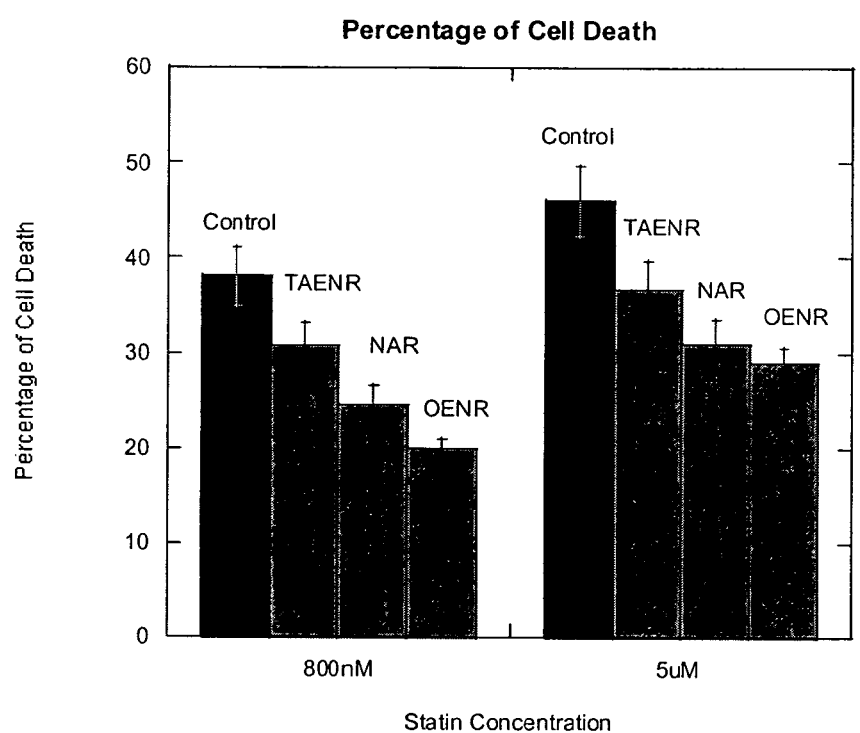
FIG. 10 shows the percentage of cell death after 48-hour treatment with lovastatin (800 nM and 5 µM). Mouse ES cells were treated in the presence of nicotinate riboside derivatives NAR (500 µM), OENR (1 mM), TAENR (1 mM). Abbreviations: NAR: Nicotinic acid riboside, OENR: O-ethyl nicotinamide riboside, TAENR: tri-O-acetyl O'-ethyl nicotinamide riboside. Control cells were not treated with a derivative. Cell death percentage is determined by the percentage of total viable cells in the statin treated wells versus the untreated (no statin) controls. The effect of each additive to cell death is computed similarly, by comparison to a no statin control in which the nicotinate riboside derivative is also present. Cell counts in untreated controls (no statin) for each experimental group were similar, indicative of a lack of toxicity of the compounds on cells.
Figure 11:
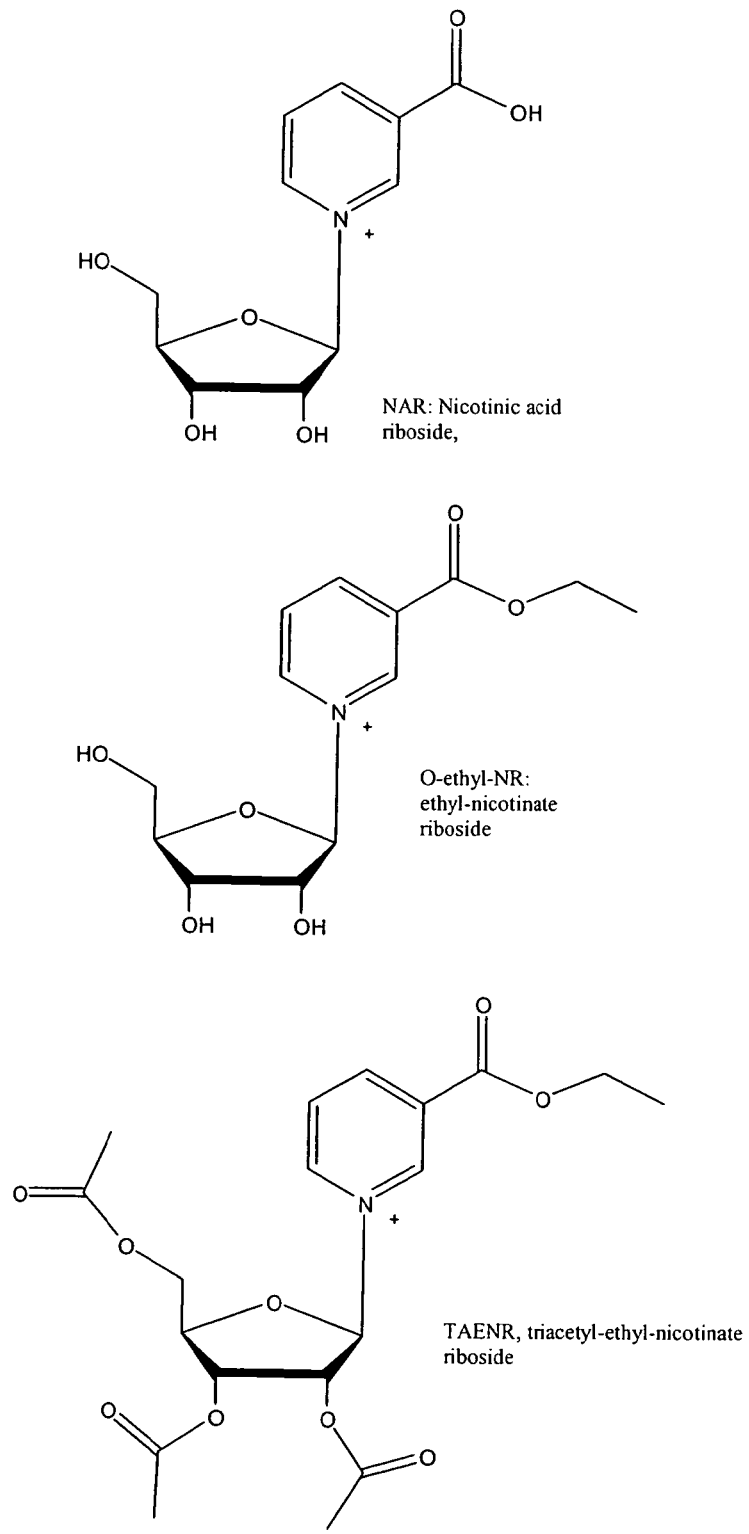
FIG. 11 shows the chemical structure of compounds tested in FIG. 10.

FIG. 10 shows data suggesting that statin toxicity can be mitigated by nicotinate riboside compounds. The lower cell death percentages show that nicotinate riboside compounds prevent cells from succumbing to toxic statin treatment. We envision that these compounds can enter NAD+ metabolism as demonstrated by our study of the potency of these molecules as NAD+ precursors and thereby protect cells from stress or toxicity. Thus, various degenerative disorders resulting from disease processes can be treated by using these compounds.

Example 12

Toxicity of Selected Nicotinamide Riboside Derivatives

Figure 12:
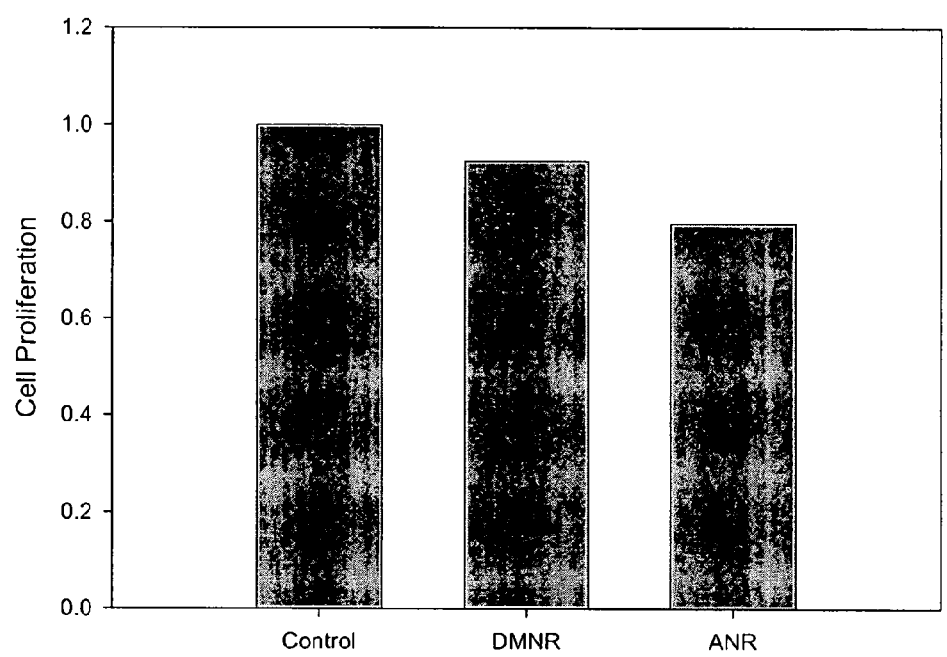
FIG. 12 illustrates data from cell proliferation assay with DMNR (1 mM) and ANR (1 mM) treatment. DMNR: N-dimethyl nicotinamide riboside, ANR: N-allyl nicotinamide riboside.
Figure 13:
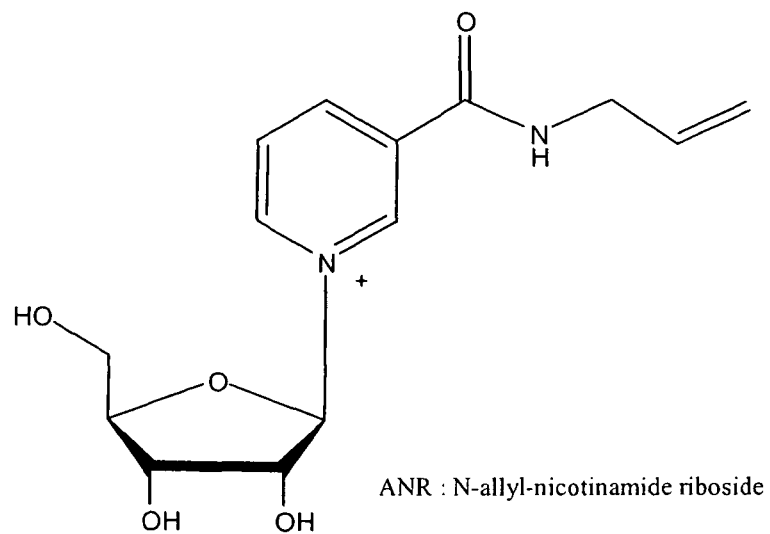
FIG. 13 shows chemical structures of compounds tested in FIG. 12.
Figure 13:
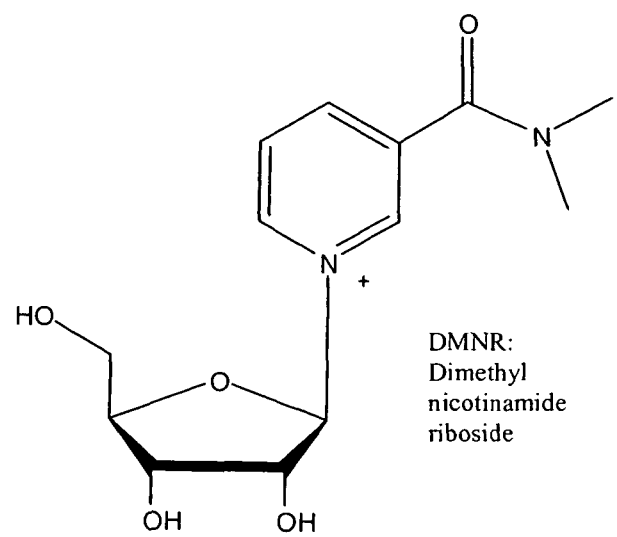
Figure 14:
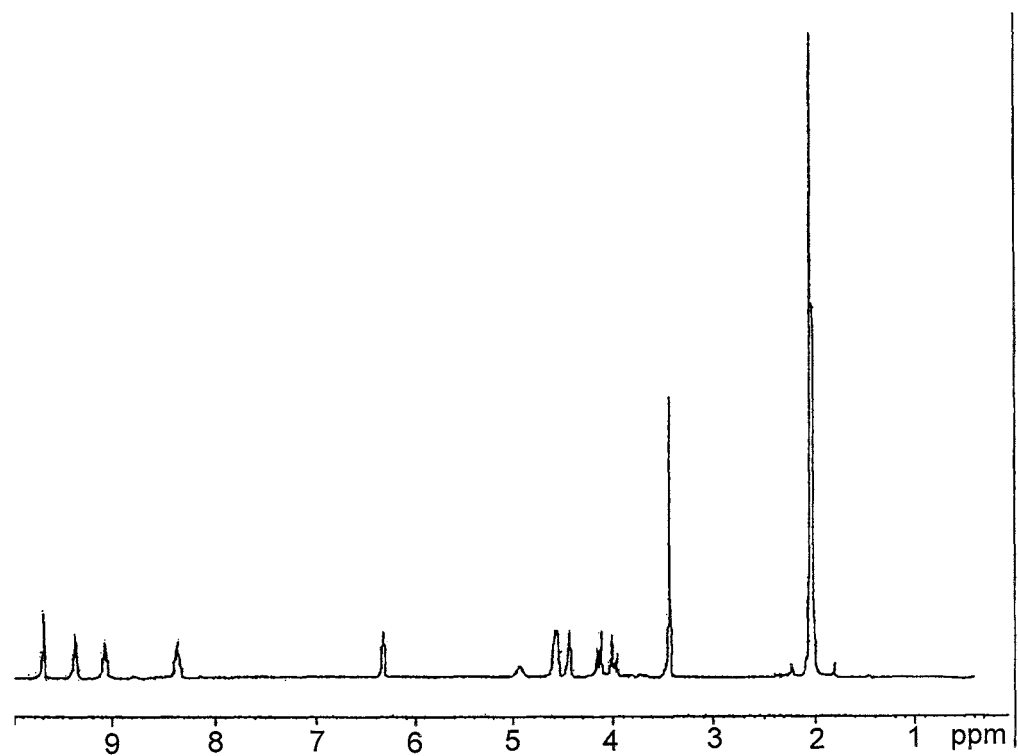
FIG. 14 shows $^1$H-NMR of nicotinamide riboside
Figure 15:
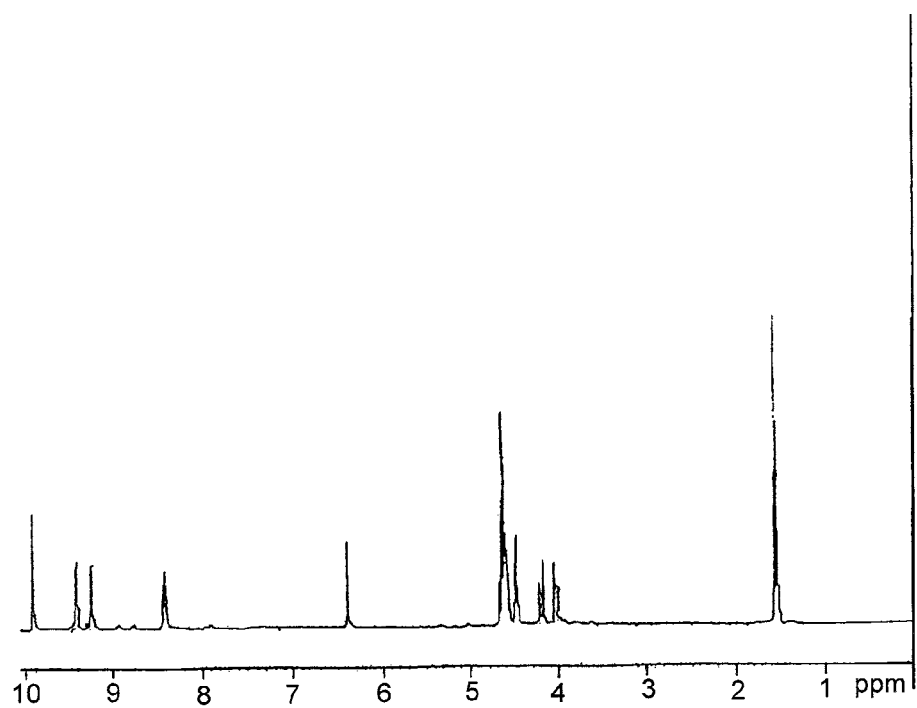
FIG. 15 shows $^1$H-NMR of O-ethyl nicotinate riboside.
Figure 16:
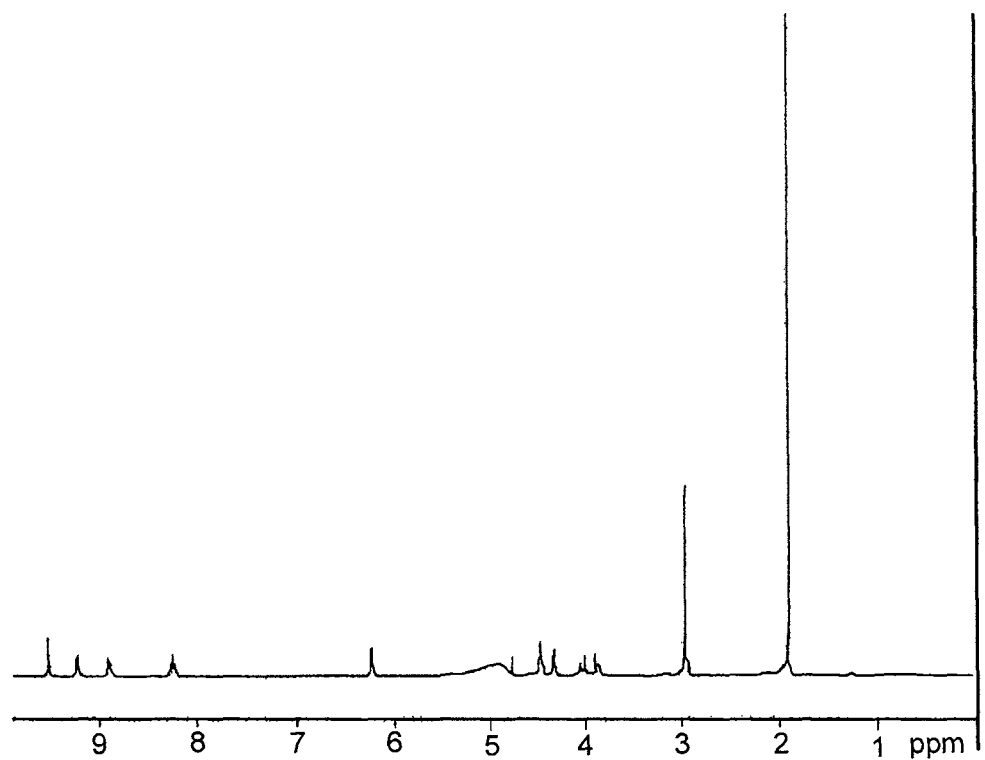
FIG. 16 shows $^1$H-NMR of N-methyl nicotinamide riboside.
Figure 17:
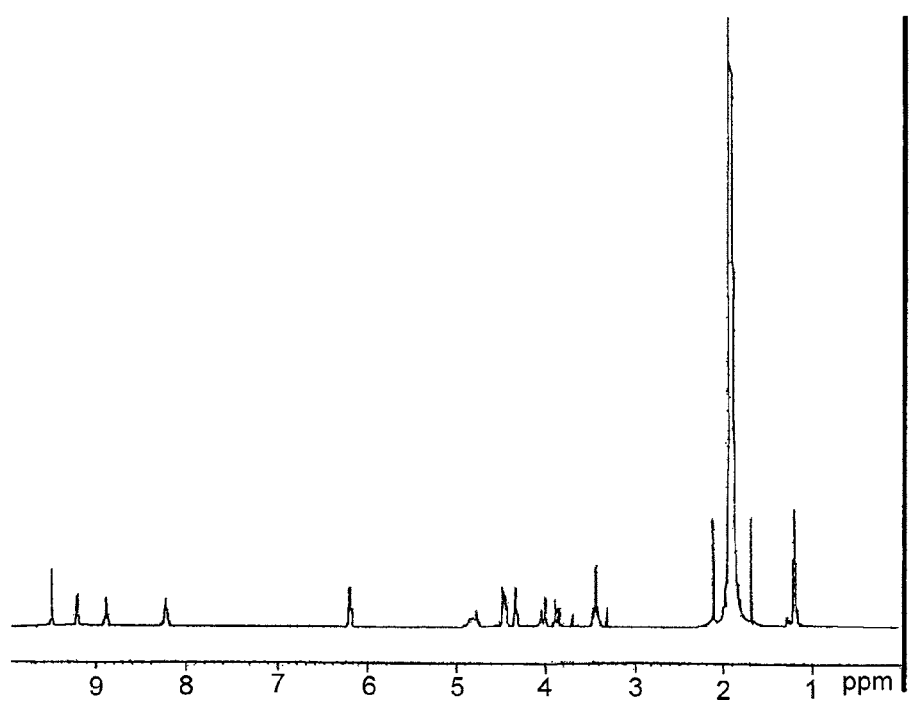
FIG. 17 shows $^1$H-NMR of N-ethyl nicotinamide riboside.
Figure 18:
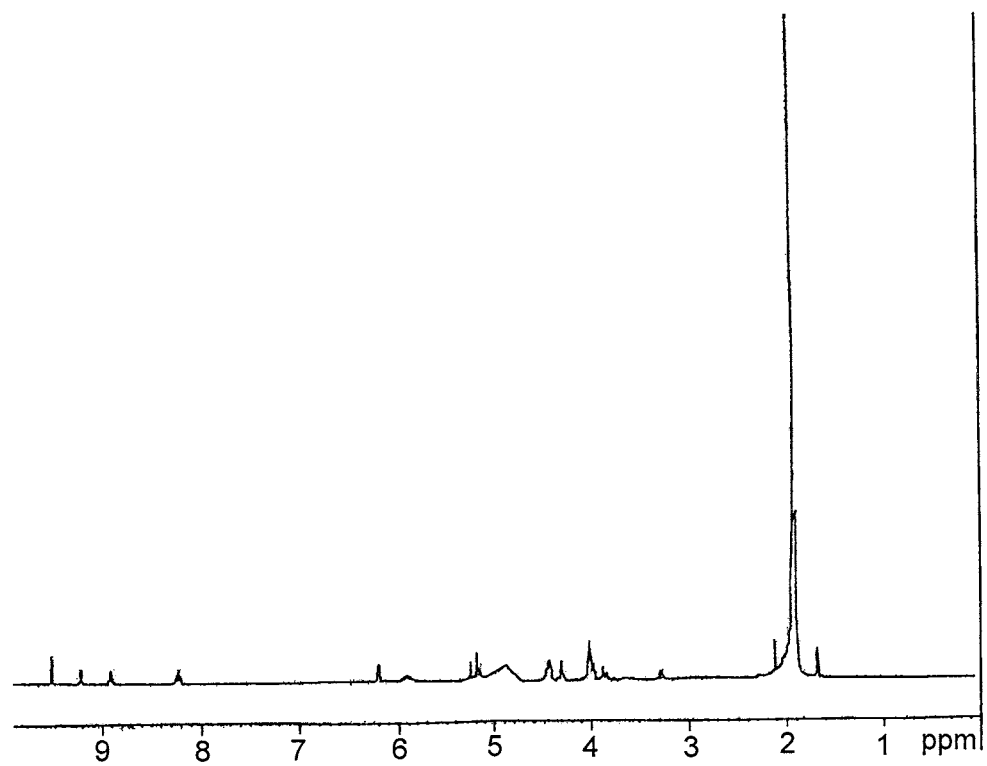
FIG. 18 shows $^1$H-NMR of N-allyl nicotinamide riboside.
Figure 19:
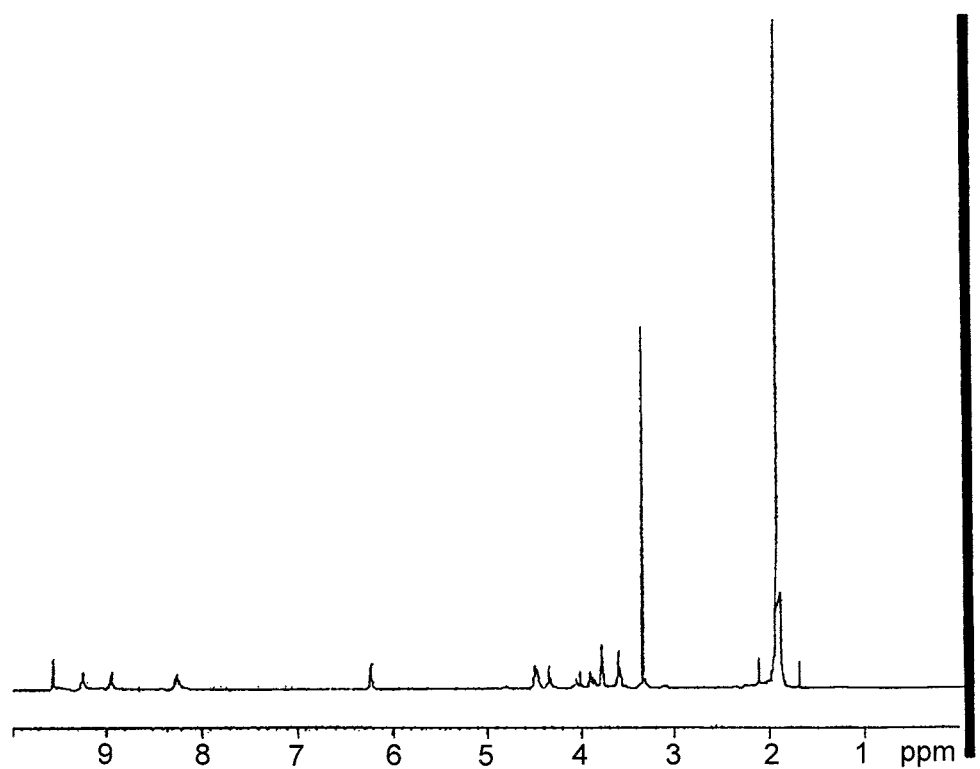
FIG. 19 shows $^1$H-NMR of N-ethanol nicotinamide riboside.
Figure 20:
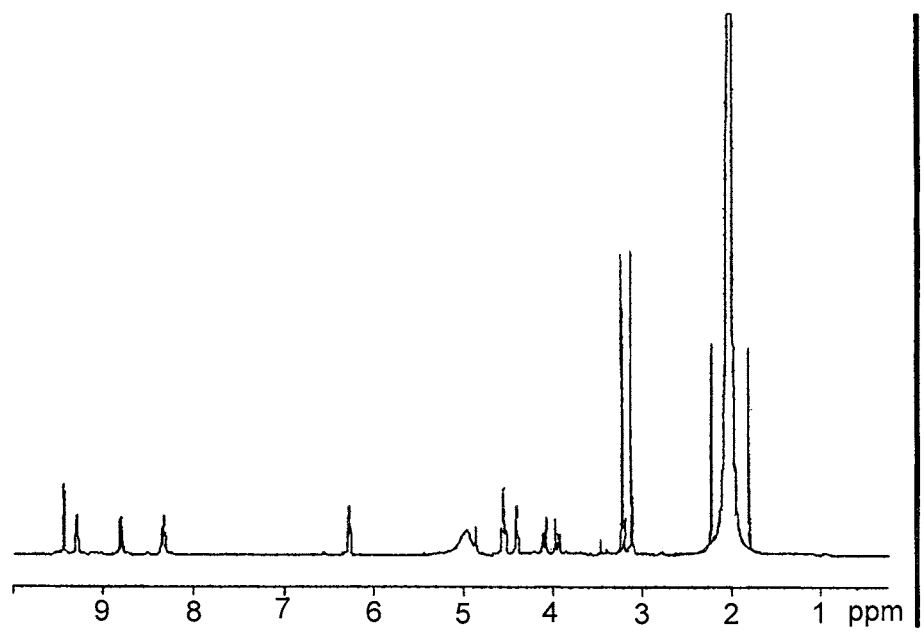
FIG. 20 shows $^1$H-NMR of dimethyl nicotinamide riboside.

To 96 well plates, mouse ES Cells were incubated in cell culture media for a 24 hour period with no compound (control) dimethyl nicotinamide riboside (1 mM) or N-allyl nicotinamide riboside (1 mM). After a 24 hour period cells were treated with MTT reagent and further incubated at 37 degrees centigrade for three additional hours. After this time, media was then removed by pipet and DMSO added to solubilize dye. Purple color was measured at 590 nm in a plate reader to assess cell viability. All samples were run in duplicate and the average MTT reading ratioed against the average reading versus control. N-allyl nicotinamide riboside is able to reduce cell proliferation in comparison with controls that are not treated with compound (FIG. 12).

Example 13

Chemical Synthesis and Characterization

All the organic solvents and reagents were purchased from Sigma-Aldrich Corporation and VWR Scientific and used without further purification. The HPLC system consists of a Hitachi EZChrom Elite HPLC system with a L2450 diode array as a detector. The purification system employed a mobile phase system involving 20 mM of ammonium acetate buffer with a flow rate of 2.0 mL/min and a Waters Delta PAK $C_{18}$ (15 μm, 300×7.8 mm) column. MALDI-mass spectra were obtained from Proteomics Resource center at Rockefeller University with using the PerSeptive Voyager DERP MALDI-TOF Mass Spectrometer. HRMS spectra were obtained from the Hunter College Mass Spectrometry Facility. $^1$H and $^{13}$C NMR spectra were recorded on Bruker NMR spectrometer operating at 400 MHz (DPX Avance), respectively. $^1$H and $^{13}$C chemical shifts are expressed in ppm with respect to the standard deuterium solvent peaks.

Phenyl Nicotinate

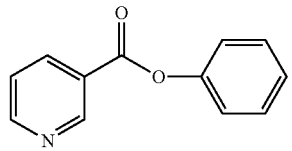 [SMILES: O=C(Oc1ccccc1)c1cccnc1]

Nicotinic chloride (1.78 g, 10 mmoL) was added to phenol (1.29 g, 12 mmoL) in 10 mL of tetrahydrofuran (THF). Triethylamine (5 mL) and pyridine (5 mL) were then added to the mixture, which was then stirred at room temperature overnight. After THF was evaporated, the mixture was washed with ethyl acetate in water for three times. The ethyl acetate (EtOAC) layer was then purified with silica column (Hexane: EtOAC=4:1) to give pure product. 1H NMR (400 MHz, CDCl$_3$): δ=9.40 (s, 1H), 8.86 (d, 1H), 8.46 (d, 1H), 7.45 (m, 3H), 7.32 (d, 1H), 7.24 (m, 2H).

2',3',5'-Triacetyl ethyl nicotinate riboside (2)

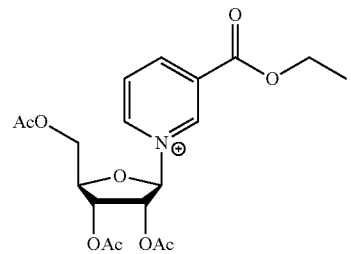

1 equiv. of trimethylsilyl trifluoromethanesulfonate (TM-SOTf) was slowly added into ethyl nicotinate (0.9 mL, 6.6 moL) and 1,2,3,5-tetra-O-acetyl-β-D-ribofuranose (1.4 g, 4.4 mmol) in 50 mL anhydrous methylene chloride at room temperature. The mixture was then heated to reflux for 8 hr. TLC (MeOH:MeOH:TEA=5:0.3:0.05) stained with 10% of H$_2$SO$_4$ in MeOH showed the disappearance of the ribofuranose, and an almost pure product. The product 2 was then used directly for the next step after methylene chloride was evaporated. MS: M/Z (%): 410.06 (14, [M]$^+$), 259.0 (100), 138.9 (22).

2',3',5'-Triacetyl phenyl nicotinate riboside (8)

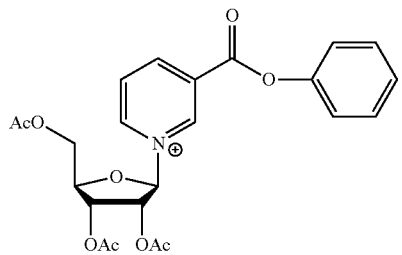

1 equiv. of trimethylsilyl trifluoromethanesulfonate (TM-SOTf) was slowly added into phenyl nicotinate (100 mg, 0.41 mmoL) and 1,2,3,5-tetra-O-acetyl-β-D-ribofuranose (159 mg, 0.5 mmol) in 15 mL anhydrous methylene chloride at room temperature. The mixture was then heated to reflux for 5 hr. TLC (MeOH:MeOH:TEA=5:0.3:0.05) stained with 10% of $H_2SO_4$ in MeOH showed the disappearance of 1, and almost pure product. The product could be used directly for the next step after methylene chloride was evaporated. MS: M/Z (%): 458.1 (12, $[M]^+$), 139.0 (64), 200.0 (76).

β-nicotinamide riboside (3)

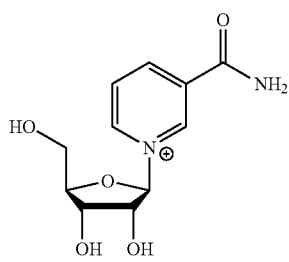

Compound 2 (180 mg, 0.44 mmol) was added into 4.7 mL of 4N of $NH_3$/MeOH on ice. After mixed well, the reaction was stored at 4° C. overnight. After methanol was removed in vacuum, the residue was dissolved in water, and extracted with ethyl acetate for three times to get rid of the non-polar impurity. The water layer was then concentrated and injected into reverse HPLC for purification. 1H NMR (400 MHz, $D_2O$): δ=9.60 (s, 1H), 9.31 (d, 1H), 8.92 (d, 1H), 8.16 (t, 1H), 6.06 (d, 1H), 4.31 (m, 2H), 4.19 (t, 1H), 3.90 (dd, 1H), 3.74 (dd, 1H). 13C NMR (300 MHz, $D_2O$): δ=146.0, 143.0, 141.3, 128.7, 100.2, 88.1, 77.7, 70.2, 60.6. MS: 255 (67, $[M]^+$), 133.0 (4), 123.0 (82). HRMS (ESI) m/z $[M]^+$ calcd for $C_{11}H_{15}N_2O$ 255.09755, found 255.09801.

O-alkyl β-nicotinic riboside (4, 5)

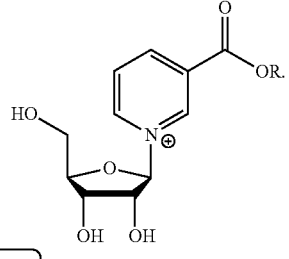

Compound 2 (25 mg, 0.61 μmol) was added into 0.9 mL of NaOMe/MeOH (255 mM, to form 4) or NaOEt/EtOH (312 mM, to form 5) on ice. After mixed well, the reaction was stored at −20° C. overnight. The reaction was quenched with addition of acetic acid to pH=7. After organic solvent was removed in vacuum, the residue was dissolved in water, and extracted with cyclohexane to get rid of the non-polar impurity. The water layer was then concentrated and injected into reverse HPLC for purification.

O-methyl β-nicotinic riboside (4): 1H NMR (400 MHz, $D_2O$): δ=9.74 (s, 1H), 9.24 (d, 1H), 9.05 (d, 1H), 8.23 (t, 1H), 6.21 (d, 1H), 4.42 (m, 2H), 4.29 (t, 1H), 3.99 (m, 4H), 3.84 (dd, 1H). 13C NMR (300 MHz, $D_2O$): δ=147.8, 144.0, 142.2, 129.0, 100.5, 87.9, 77.8, 69.9, 60.4, 54.4. MS: m/z (%): 270.1 (42, $[M]^+$), 152.1 (81), 138.0 (92). HRMS (ESI) m/z $[M]^+$ calcd for $C_{12}H_{16}NO_6$ 270.09721, found 270.09737.

O-ethyl β-nicotinic riboside (5): 1H NMR (400 MHz, $D_2O$): δ=9.86 (s, 1H), 9.37 (d, 1H), 9.20 (d, 1H), 8.37 (t, 1H), 6.35 (d, 1H), 4.55 (m, 4H), 4.44 (t, 1H), 4.15 (dd, 1H), 3.98 (dd, 1H), 1.49 (t, 3H). 13C NMR (300 MHz, $D_2O$): δ=148.9, 145.0, 143.5, 129.8, 101.7, 88.8, 79.0, 70.8, 65.7, 61.4, 15.0. MS: m/z (%): 284.1 (77, $[M]^+$), 256.0 (6), 212.0 (83), 133.0 (7), 124.0 (14). HRMS (ESI) m/z $[M]^+$ calcd for $C_{13}H_{18}NO_6$ 284.11286, found 284.11339.

β-Nicotinic Acid Riboside (6)

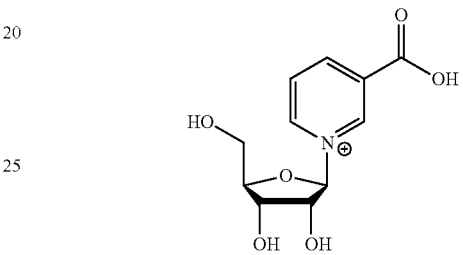

Compound 5 was dissolved into phosphate buffer (150 mM, pH=7.0). 10 uL of esterase was added to the mixture, and mixed well. The reaction was run at 25° C. overnight. HPLC injection showed the purity of product is above 98%. 1H NMR (400 MHz, $D_2O$): δ=; MS: m/z (%): 256.1 (3, $[M]^+$), 228.0 (80), 207.1 (42), 146.1 (17), 124.0 (23).

N-alkyl β-NAR Derivatives (9, 10, 11, 12, 13)

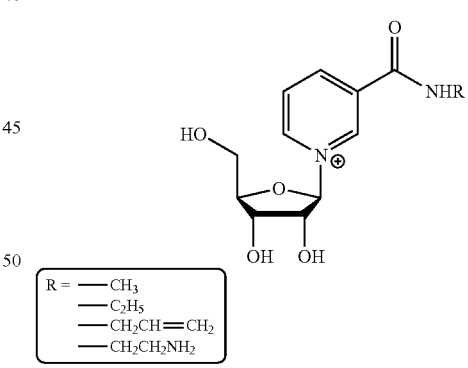

Compound 8 (25 mg, 0.61 μmol) was added to various amine (400 μM) in 0.9 mL of trifluoroethanol. After mixed well, the reaction was stored at 4° C. overnight. On the next day, 4N of $NH_3$/MeOH was added into the reaction mixture, and the reaction was stored at −20° C. overnight. After the reaction was quenched with addition of HCl to make pH<7, the organic solvent was removed in vacuum. The residue was dissolved in water and isolated with an Octadecyl-C18 disposable extraction column.

N-methyl β-nicotinamide riboside (9): 1H NMR (400 MHz, $D_2O$): δ=9.58 (s, 1H), 9.28 (d, 1H), 8.95 (d, 1H), 8.30 (t, 1H), 6.27 (d, 1H), 4.75 (1H), 4.53 (m, 1H), 4.39 (t, 1H), 4.08 (dd, 1H), 3.93 (dd, 1H), 3.00 (s, 3H). 13C NMR (300 MHz, D$_2$O): δ=145.3, 142.4, 140.0, 128.4, 100.0, 87.8, 77.5, 69.9, 60.2, 27.5. MS: m/z (%): 269.1 (13, [M]$^+$), 248.0, 212.0, 137.0 (100). HRMS (ESI) m/z [M]$^+$ calcd for C$_{12}$H$_{17}$N$_2$O$_5$ 269.11320, found 269.11378.

N-ethyl β-nicotinamide riboside (10): 1H NMR (400 MHz, D$_2$O): δ=9.57 (s, 1H), 9.27 (d, 1H), 8.95 (d, 1H), 8.29 (t, 1H), 6.27 (d, 1H), 4.52 (m, 2H), 4.38 (t, 1H), 4.07 (dd, 1H), 3.92 (dd, 1H), 3.49 (q, 2H), 1.26 (t, 3H). 13C NMR (300 MHz, D$_2$O): δ=145.8, 142.7, 140.3, 129.0, 100.5, 88.0, 77.8, 70.0, 60.6, 36.0, 13.4. MS: m/z (%): 283.1 (93, [M]$^+$), 227 (50), 207.1 (100), 151.1 (44).

N-allyl β-nicotinamide riboside (11): 1H NMR (400 MHz, D$_2$O): δ=9.59 (s, 1H), 9.28 (d, 1H), 8.98 (d, 1H), 8.30 (t, 1H), 6.27 (d, 1H), 5.99 (m, 1H), 5.27 (m, 1H), 4.52 (m, 2H), 4.38 (t, 1H), 4.08 (m, 3H), 3.92 (dd, 1H). 13C NMR (300 MHz, D$_2$O): δ=146.2, 143.5, 140.7, 133.7, 129.4, 117.3, 100.9, 88.4, 78.2, 70.8, 61.0, 43.5. MS: m/z (%): 295.1 (63, [M]$^+$), 163.1 (98), 133.1 (5), 123.1 (88).

N-ethanol β-nicotinamide riboside (12): 1H NMR (400 MHz, D$_2$O): δ=9.55 (s, 1H), 9.24 (d, 1H), 8.93 (d, 1H), 8.24 (t, 1H), 6.22 (d, 1H), 5.99 (m, 1H), 4.48 (m, 2H), 4.33 (t, 1H), 4.02 (dd, 1H), 3.87 (dd, 1H), 3.77 (t, 2H), 3.58 (t, 2H). 13C NMR (300 MHz, D$_2$O): δ=145.0, 142.7, 140.3, 128.2, 99.3, 88.0, 77.8, 69.6, 59.9, 48.5, 41.9. MS: m/z (%): 295.1 (63, [M]$^+$), 163.1 (98), 133.1 (5), 123.1 (88).

N-dimethyl β-NAR

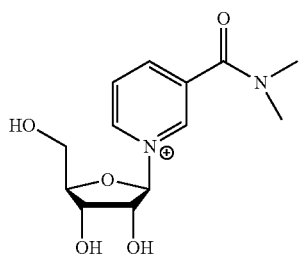

MS: m/z (%): 283.3 (13, [M]$^+$), 151.2 (100).

5'-O-acetyl N-alkyl β-NAR derivatives (9',10',11',12',13')

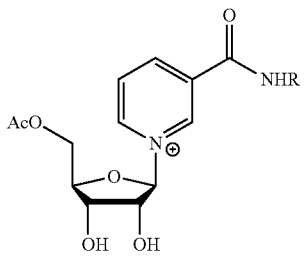

R = —CH$_3$
—C$_2$H$_5$
—CH$_2$CH=CH$_2$
—CH$_2$CH$_2$NH$_2$

Compound 8 (25 mg, 0.61 μmol) was added to various amine (400 μM) in 0.9 mL of trifluoroethanol. After mixed well, the reaction was stored at 4° C. overnight. After the reaction was quenched with addition of HCl to make pH<7, the organic solvent was removed in vacuum. The residue was dissolved in water and isolated with an Octadecyl-C18 disposable extraction column.

5'-O-acetyl N-methyl β-nicotinic riboside (9'): 1H NMR (400 MHz, D$_2$O) δ=9.42 (s, H$_2$, 1H), 9.23 (d, H$_6$, 1H), 8.98 (d, H$_4$, 1H), 8.33 (t, H$_5$, 1H), 6.30 (d, H$_1'$, 1H), 4.73 (t, H$_2'$, 1H), 4.55 (m, 3H), 4.40 (t, H$_3'$, 1H), 3.02 (s, 3H), 2.11 (s, 3H). MS: m/z (%): 311.1 (67, [M]$^+$), 269.1 (13), 221.1 (13), 137.1 (100).

5'-O-acetyl N-ethyl β-nicotinic riboside (10'): MS: m/z (%): 325.1 (12, [M]$^+$), 283.1 (7), 151.1 (77), 139.1 (22), 115.1 (68).

5'-O-acetyl N-allyl β-nicotinic riboside (11'): MS: m/z (%): 337.1 (18, [M]$^+$), 163.0 (71), 138.0 (100), 124.0 (18).

5'-O-ethylenediamine N-methyl β-nicotinic riboside (12'): MS: m/z (%): 340.2 (100, [M]$^+$), 298.1 (44), 166.1 (100), 124.0 (82).

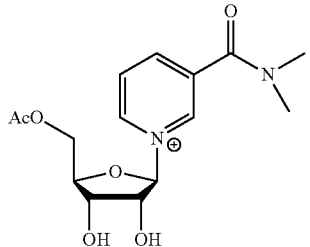

5'-O-acetyl N-dimethyl β-nicotinamide riboside (300 MHz, D$_2$O) δ=9.23 (s, H$_2$, 1H), 9.19 (d, H$_6$, 1H), 8.78 (d, H$_4$, 1H), 8.32 (t, H$_5$, 1H), 6.28 (d, H$_1'$, 1H), 4.72 (m, H$_4'$, 1H), 4.55 (t, H$_2'$, 1H), 4.52 (d, H$_5'$, 2H), 4.40 (t, H$_3'$, 1H), 3.17 (s, 3H), 3.08 (s, 3H), 2.10 (s, 3H). MS: m/z (%): 325.1 (92, [M]$^+$), 283.1 (2) 151.1 (100).

The invention claimed is:

1. A method of reducing toxicity induced by a HMGCoA reductase inhibitor in a mammal, which method comprises administering to the mammal a therapeutically effective amount of a compound of formula (I):

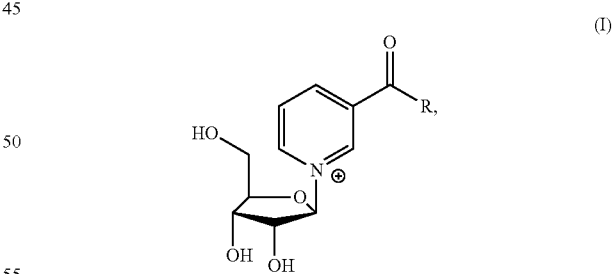

and salt complexes thereof, wherein R is selected from the group consisting of amino, alkylamino, substituted alkylamino, dialkylamino, substituted dialkylamino, alkyloxy, substituted alkyloxy, aryloxy, substituted aryloxy, hydroxylamino, substituted hydroxylamino, O-alkyloxyamino, substituted O-alkyloxyamino, aminooxy, substituted aminoxy, N-alkylaminooxy, substituted N-alkylaminoxy, hydrazino, substituted hydrazino, alkylhydrazino, and substituted alkylhydrazino, wherein the mammal has been administered the HMGCoA reductase inhibitor in an amount that produces toxicity in the mammal in the absence of the administration of the compound of formula (I), and wherein the administration of the compound of formula (I) reduces the toxicity in the mammal.

2. The method of claim 1, wherein the alkyloxy or substituted alkyloxy is selected from —OMe, —OEt, and —OCH₂CH₂OH.

3. The method of claim 1, wherein the aryloxy is —OPh.

4. The method of claim 1, wherein the alkylamino or substituted alkylamino is selected from —NHMe, —NHEt, —NHCH₂CH₂OH, —NHCH₂CH=CH₂, —NHCH(CH₃)₂, —NHCH₂CH₂NH₂, and —NHcyclopropyl.

5. The method of claim 1, wherein the dialkylamino is —N(CH₃)₂ or N-substituted pyrrolidinyl.

6. The method of claim 1, wherein the HMGCoA reductase inhibitor is a statin.

7. The method of claim 6, wherein the statin is selected from atorvastatin, cerivastatin, fluvastatin, lovastatin, mevastatin, pitavastatin, pravastatin, rosuvastatin, and simvastatin.

8. The method of claim 1, wherein the compound of formula (I) is administered to the mammal together with the HMGCoA reductase inhibitor.

9. A method of reducing toxicity induced by a HMGCoA reductase inhibitor in a mammal, which method comprises administering to the mammal a therapeutically effective amount of a compound of formula (I):

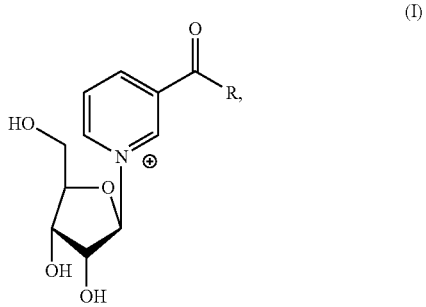

and salt complexes thereof, wherein R is selected from the group consisting of amino, alkylamino, substituted alkylamino, dialkylamino, substituted dialkylamino, alkyloxy, substituted alkyloxy, aryloxy, substituted aryloxy, hydroxylamino, substituted hydroxylamino, O-alkyloxyamino, substituted O-alkyloxyamino, aminooxy, substituted aminooxy, N-alkylaminooxy, substituted N-alkylaminoxy, hydrazino, substituted hydrazino, alkylhydrazino, and substituted alkylhydrazino, and then administering to the mammal the HMGCoA reductase inhibitor in an amount that produces toxicity in the mammal in the absence of the administration of the compound of formula (I), whereby toxicity that would have been induced by the HMGCoA reductase inhibitor is reduced in the mammal by the administration of the compound of formula (I).

10. The method of claim 1, wherein the compound of formula (I) is administered to the mammal following manifestation of toxicity by the mammal.

11. The method of claim 1, wherein the mammal is a human.

12. A pharmaceutical composition comprising
(a) a HMGCoA reductase inhibitor,
(b) a compound of formula (I):

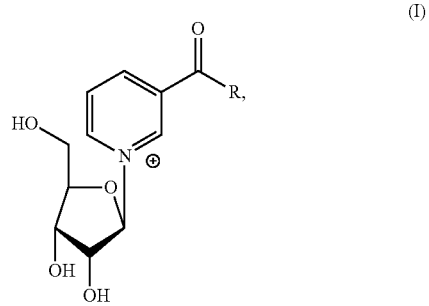

and salt complexes thereof, wherein R is selected from the group consisting of amino, alkylamino, substituted alkylamino, dialkylamino, substituted dialkylamino, alkyloxy, substituted alkyloxy, aryloxy, substituted aryloxy, hydroxylamino, substituted hydroxylamino, O-alkyloxyamino, substituted O-alkyloxyamino, aminooxy, substituted aminooxy, N-alkylaminooxy, substituted N-alkylaminoxy, hydrazino, substituted hydrazino, alkylhydrazino, and substituted alkylhydrazino, and (c) a pharmaceutically acceptable carrier.

13. A method of reducing toxicity induced by a HMGCoA reductase inhibitor in a mammal, which method comprises administering to the mammal a therapeutically effective amount of a compound of formula (I):

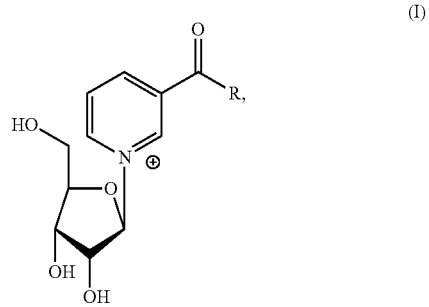

and salt complexes thereof, wherein R is selected from the group consisting of amino, alkylamino, substituted alkylamino, dialkylamino, substituted dialkylamino, alkyloxy, substituted alkyloxy, aryloxy, substituted aryloxy, hydroxylamino, substituted hydroxylamino, O-alkyloxyamino, substituted O-alkyloxyamino, aminooxy, substituted aminooxy, N-alkylaminooxy, substituted N-alkylaminoxy, hydrazino, substituted hydrazino, alkylhydrazino, and substituted alkylhydrazino, whereby toxicity induced by the HMGCoA inhibitor is reduced in the mammal, wherein the compound of formula (I) is administered to the mammal following manifestation of toxicity by the mammal.

14. The method of claim 13, wherein the alkyloxy or substituted alkyloxy is selected from —OMe, —OEt, and —OCH₂CH₂OH.

15. The method of claim 13, wherein the aryloxy is —OPh.

16. The method of claim 13, wherein the alkylamino or substituted alkylamino is selected from —NHMe, —NHEt, —NHCH$_2$CH$_2$OH, —NHCH$_2$CH=CH$_2$, —NHCH(CH$_3$)$_2$, —NHCH$_2$CH$_2$NH$_2$, and —NHcyclopropyl.

17. The method of claim 13, wherein the dialkylamino is —N(CH$_3$)$_2$ or N-substituted pyrrolidinyl.

18. The method of claim 13, wherein the HMGCoA reductase inhibitor is a statin.

19. The method of claim 18, wherein the statin is selected from atorvastatin, cerivastatin, fluvastatin, lovastatin, mevastatin, pitavastatin, pravastatin, rosuvastatin, and simvastatin.

20. The method of claim 13, wherein the method comprises administering the HMGCoA reductase inhibitor in a concentration that typically produces toxicity in the mammal and the compound of formula (I) is administered under conditions such that the toxicity is prevented.

21. The method of claim 13, wherein the mammal is a human.

* * * * *